United States Patent
Kondo et al.

(10) Patent No.: US 10,593,430 B2
(45) Date of Patent: Mar. 17, 2020

(54) METHOD AND RECORDING MEDIUM

(71) Applicant: Panasonic Intellectual Property Management Co., Ltd., Osaka (JP)

(72) Inventors: Kenji Kondo, Fukui (JP); Kazutoyo Takata, Fukui (JP); Kazuki Kozuka, Osaka (JP); Hirohiko Kimura, Fukui (JP); Toyohiko Sakai, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 553 days.

(21) Appl. No.: 15/266,344

(22) Filed: Sep. 15, 2016

(65) Prior Publication Data

US 2017/0091413 A1    Mar. 30, 2017

(30) Foreign Application Priority Data

Sep. 29, 2015   (JP) ................................. 2015-191313

(51) Int. Cl.
G06F 19/00 (2018.01)
G16H 50/20 (2018.01)
G16H 50/70 (2018.01)

(52) U.S. Cl.
CPC .......... G16H 50/70 (2018.01); G06F 19/321 (2013.01); G16H 50/20 (2018.01)

(58) Field of Classification Search
CPC combination set(s) only.
See application file for complete search history.

(56) References Cited

U.S. PATENT DOCUMENTS

| | | | |
|---|---|---|---|
| 2007/0064981 A1* | 3/2007 | Meijer | G06F 19/321 382/128 |
| 2008/0243395 A1 | 10/2008 | Oosawa et al. | |
| 2009/0080734 A1 | 3/2009 | Moriya et al. | |
| 2010/0228727 A1* | 9/2010 | Hisanaga | G06F 19/321 707/723 |
| 2010/0274776 A1 | 10/2010 | Iizuka | |
| 2011/0099032 A1 | 4/2011 | Miyasa et al. | |

(Continued)

FOREIGN PATENT DOCUMENTS

| | | |
|---|---|---|
| JP | 2008-257292 | 10/2008 |
| JP | 2010-017410 | 1/2010 |
| JP | 2010-079568 | 4/2010 |

(Continued)

OTHER PUBLICATIONS

Extended European Search Report dated Dec. 16, 2016 in corresponding European Application No. 16189409.2.

(Continued)

Primary Examiner — Kira Nguyen
(74) Attorney, Agent, or Firm — Wenderoth, Lind & Ponack, L.L.P.

(57) ABSTRACT

A method includes displaying, on a display of an information terminal, thumbnail images of similar cases received from a case search system and displaying, in a disease name list display area, a disease name list formed from a list of disease names of the similar cases and the number of cases. If a plurality of regions of interest are set by a user when a search is conducted, the disease name list enters a mode in which the name of a concomitant disease is displayable therein.

6 Claims, 62 Drawing Sheets

(56) References Cited

U.S. PATENT DOCUMENTS

2012/0283574 A1* 11/2012 Park .................. G06K 9/46
600/476
2016/0317369 A1* 11/2016 Hagler ................ A61G 5/10

FOREIGN PATENT DOCUMENTS

JP        2014-039852      3/2014
JP        2014-233611     12/2014

OTHER PUBLICATIONS

Alex M. Aisen et al., "Automated Storage and Retrieval of Thin-Section CT Images to Assist Diagnosis: System Description and Preliminary Assessment", Radiology, Radiological Society of North America, Inc, US, vol. 228, No. 1, Jul. 1, 2003, pp. 265-270, XP002514225.

* cited by examiner

NON-TUBERCULOUS
MYCOBACTERIOSIS          DISTANCE: 0.05
↖711                          ↖712

DISEASE NAME LIST          730

| | |
|---|---|
| MYCOSIS | 14 | — 731
| ASPERGILLOSIS | 8 | — 732
| CRYPTOCOCCOSIS | 6 | — 733
| NEOPLASTIC | 13 | — 734
| LUNG CANCER | 10 | — 735
| METASTATIC LUNG CANCER | 3 | — 736
| NONNEOPLASTIC | 6 | — 737
| LUNG ABSCESS | 4 | — 738
| SARCOIDOSIS | 1 | — 739
| SEPTIC EMBOLI | 1 | — 740
| MYCOBACTERIOSIS | 6 | — 741
| NONTUBERCULOUS MYCOBACTERIA | 4 | — 742
| TUBERCULOSIS | 2 | — 743
| OTHERS | 2 | — 744
| BRONCHIECTASIS | 1 | — 745
| ... | 1 |

| 1100 | PATIENT ID | 123456 |
|---|---|---|
| 1200 | NAME | TARO PANA |
| 1300 | AGE | 28 |
| 1400 | GENDER | MALE |
| 1500 | PERSONAL MEDICAL HISTORY | NONE |
| 1600 | FAMILY HISTORY | NONE |
| 1700 | MAJOR COMPLAINT | COUGHING |
| 1800 | TEST INFORMATION | (FIG. 12) |
| 1900 | DEFINITIVE DIAGNOSIS | MYCOPLASMA PNEUMONIA |

| 1810 | TEST ID | 13227895 |
|---|---|---|
| 1820 | TEST DATE AND TIME | 2/5/20XX 10:00 |
| 1830 | TEST TYPE | BLOOD TEST |
| 1840 | TEST RESULT | YYYY1 |

| TEST ID | 13227903 |
|---|---|
| TEST DATE AND TIME | 2/5/20XX 11:00 |
| TEST TYPE | PLAIN X-RAY (CHEST) |
| TEST RESULT | YYYY2 |

| TEST ID | 13227989 |
|---|---|
| TEST DATE AND TIME | 2/9/20XX 9:00 |
| TEST TYPE | CT (CHEST) |
| TEST RESULT | YYYY3 |

| TEST ID | 13227989 |
| FINDINGS | Multiple nodules of size 0.5 cm to 1 cm in right lung field.... |
| DIAGNOSIS | Inflamed nodule or lung phthisis is suspected. |

1810 — TEST ID
3100 — FINDINGS
3200 — DIAGNOSIS

FIG. 18

| PATIENT ID | PATIENT NAME | TEST DATE AND TIME | TEST ID | TEST TYPE |
|---|---|---|---|---|
| 443982 | ICHIRO YAMADA | 12/1/20XX | 23982874 | MR (HEAD) |
| 123456 | TARO PANA | 5/8/20XX | 13227989 | CT (CHEST) |
| 345455 | ... | ... | ... | ... |
| 235982 | ... | ... | ... | ... |

~800

| SERIES ID | DEFINITION | IMAGE |
|---|---|---|
|  |  |  |
|  |  |  |
|  |  |  |

~810

FIG. 19
| PATIENT ID | PATIENT NAME | TEST DATE AND TIME | TEST ID | TEST TYPE |
|---|---|---|---|---|
| 443982 | ICHIRO YAMADA | 12/1/20XX | 23982874 | MR (HEAD) |
| 123456 | TARO PANA | 5/8/20XX | 13227989 | CT (CHEST) |
| 345455 | ... | ... | ... | ... |
| 235982 | ... | ... | ... | ... |
~800
| SERIES ID | DEFINITION | IMAGE |
|---|---|---|
| CT152729 | LUNG WINDOW SETTINGS SLICE THICKNESS: 5 mm |  |
| CT152730 | LUNG WINDOW SETTINGS SLICE THICKNESS: 1 mm |  |
| CT152731 | MEDIASTINAL WINDOW SETTINGS SLICE THICKNESS: 5 mm |  |
~810

FIG. 23
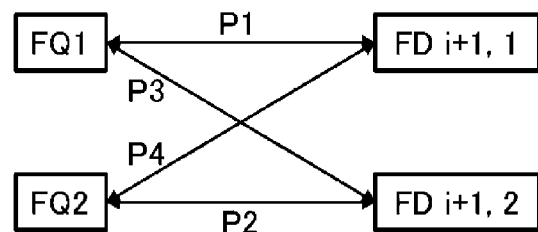
FIG. 24
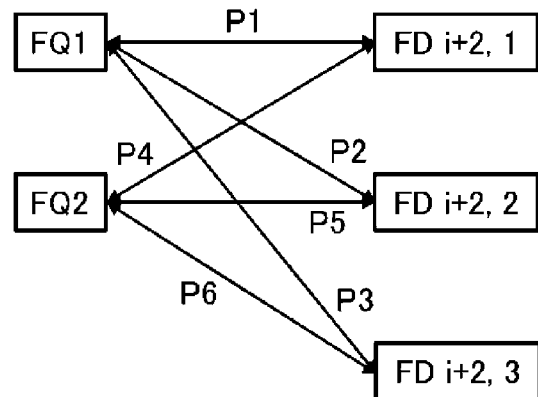

| DISEASE ID | LARGE CATEGORY DISEASE NAME | SMALL CATEGORY DISEASE NAME | NUMBER OF CASES | SIMILAR CASE ID |
|---|---|---|---|---|
| DIS002_001 | NEOPLASTIC | LUNG CANCER | 10 | SIM1592, SIM2205, SIM8137, ... |
| DIS011_002 | MYCOSIS | ASPERGILLOSIS | 8 | SIM2205, SIM6089, SIM8137, ... |
| DIS011_003 | MYCOSIS | CRYPTOCOCCOSIS | 6 | SIM4172, ... |
| DIS004_012 | NONNEOPLASTIC | LUNG ABSCESS | 4 | ... |
| DIS003_002 | MYCOBACTERIOSIS | NON-TUBERCULOUS MYCOBACTERIOSIS | 4 | SIM6089, ... |
| DIS002_004 | NEOPLASTIC | METASTATIC LUNG CANCER | 3 | SIM0157, ... |
| DIS003_001 | MYCOBACTERIOSIS | LUNG PHTHISIS | 2 | ... |
| DIS004_008 | NONNEOPLASTIC | INFLAMED NODULE | 1 | ... |
| DIS004_016 | NONNEOPLASTIC | SEPTIC EMBOLUS | 1 | ... |
| DIS099_004 | OTHERS | BRONCHIAL ECTASIA | 1 | ... |

| DISEASE ID | LARGE CATEGORY DISEASE NAME | NUMBER OF CASES | SIMILAR CASE ID |
|---|---|---|---|
| DIS011 | MYCOSIS | 14 | SIM2205, SIM4172, SIM6089, ... |
| DIS002 | NEOPLASTIC | 13 | SIM0157, SIM1592, SIM2205, ... |
| DIS004 | NONNEOPLASTIC | 6 | ... |
| DIS003 | MYCOBACTERIOSIS | 6 | SIM6089, ... |
| DIS099 | OTHERS | 2 | ... |

| DISEASE ID | LARGE CATEGORY DISEASE NAME | SMALL CATEGORY DISEASE NAME | NUMBER OF CASES | SIMILAR CASE ID |
|---|---|---|---|---|
| DIS011 | MYCOSIS | — | 14 | SIM2205, SIM4172, SIM6089, ... |
| DIS011_002 | MYCOSIS | ASPERGILLOSIS | 8 | SIM2205, SIM6089, SIM8137, ... |
| DIS011_003 | MYCOSIS | CRYPTOCOCCOSIS | 6 | SIM4172, ... |
| DIS002 | NEOPLASTIC | — | 13 | SIM0157, SIM1592, SIM2205, ... |
| DIS002_001 | NEOPLASTIC | LUNG CANCER | 10 | SIM1592, SIM2205, SIM8137, ... |
| DIS002_004 | NEOPLASTIC | METASTATIC LUNG CANCER | 3 | SIM0157, ... |
| DIS004 | NONNEOPLASTIC | — | 6 | ... |
| DIS004_012 | NONNEOPLASTIC | LUNG ABSCESS | 4 | ... |
| DIS004_008 | NONNEOPLASTIC | SARCOIDOSIS | 1 | ... |
| DIS004_016 | NONNEOPLASTIC | SEPTIC EMBOLUS | 1 | ... |
| DIS003 | MYCOBACTERIOSIS | — | 6 | SIM6089, ... |
| DIS003_002 | MYCOBACTERIOSIS | NON-TUBERCULOUS MYCOBACTERIOSIS | 4 | SIM6089, ... |
| DIS003_001 | MYCOBACTERIOSIS | LUNG PHTHISIS | 2 | ... |
| DIS099 | OTHERS | — | 2 | ... |
| DIS099_004 | OTHERS | BRONCHIAL ECTASIA | 1 | ... |

| DISEASE ID | CONCOMITANT DISEASE ID | NUMBER OF CASES | SIMILAR CASE ID |
|---|---|---|---|
| DIS011_002 | DIS002_001 | 2 | SIM2205, SIM8137 |
| DIS011_002 | DIS003_002 | 1 | SIM6089 |
| DIS002_001 | DIS011_002 | 2 | SIM2205, SIM8137 |
| DIS002_001 | DIS007_004 | 3 | SIM0003, SIM1991, SIM2931 |
| ... | ... | ... | ... |

FIG. 31

DISEASE NAME LIST           730

| LUNG CANCER | 10 |
| ASPERGILLOSIS | 8 |
| CRYPTOCOCCOSIS | 6 |
| LUNG ABSCESS | 4 |
| NON-TUBERCULOUS MYCOBACTERIOSIS | 4 |
| METASTATIC LUNG CANCER | 3 |
| LUNG PHTHISIS | 2 |
| INFLAMED NODULE | 1 |
| SEPTIC EMBOLUS | 1 |
| BRONCHIAL ECTASIA | 1 |
| UNCERTAIN | 1 |

FIG. 32

DISEASE NAME LIST           730

| MYCOSIS | 14 |
| NEOPLASTIC | 13 |
| NONNEOPLASTIC | 6 |
| MYCOBACTERIOSIS | 6 |
| OTHERS | 2 |

FIG. 33

| DISEASE NAME LIST | | 730 |
|---|---|---|
| MYCOSIS | 14 | 7301 |
|    ASPERGILLOSIS | 8 | 7302 |
|    CRYPTOCOCCOSIS | 6 | |
| NEOPLASTIC | 13 | |
|    LUNG CANCER | 10 | |
|    METASTATIC LUNG CANCER | 3 | |
| NONNEOPLASTIC | 6 | |
|    LUNG ABSCESS | 4 | |
|    SARCOIDOSIS | 1 | |
|    SEPTIC EMBOLUS | 1 | |
| MYCOBACTERIOSIS | 6 | |
|    NON-TUBERCULOUS MYCOBACTERIOSIS | 4 | |
|    LUNG PHTHISIS | 2 | |
| OTHERS | 2 | |
|    BRONCHIAL ECTASIA | 1 | |
|    ... | 1 | |

| DISEASE ID | LARGE CATEGORY DISEASE NAME | SMALL CATEGORY DISEASE NAME |
|---|---|---|
| ... | | |
| DIS011 | MYCOSIS | — |
| DIS011_002 | MYCOSIS | ASPERGILLOSIS |
| DIS011_003 | MYCOSIS | CRYPTOCOCCOSIS |
| ... | | |

FIG. 41

| DISEASE NAME LIST | 730 | |
|---|---|---|
| MYCOSIS | 14 | |
| ASPERGILLOSIS | 8 | ⇦ MOUSE OVER |
| CRYPTOCOCCOSIS | 6 | |
| NEOPLASTIC | 13 | |
| LUNG CANCER | 10 | |
| METASTATIC LUNG CANCER | 3 | |
| NONNEOPLASTIC | 6 | |
| LUNG ABSCESS | 4 | |
| SARCOIDOSIS | 1 | |
| SEPTIC EMBOLUS | 1 | |
| MYCOBACTERIOSIS | 6 | |
| NON-TUBERCULOUS MYCOBACTERIOSIS | 4 | |
| LUNG PHTHISIS | 2 | |
| OTHERS | 2 | |
| BRONCHIAL ECTASIA | 1 | |
| ... | | |

⇧

| DISEASE NAME LIST | 730 | |
|---|---|---|
| MYCOSIS | 14 | |
| ASPERGILLOSIS | 8 | |
| <CONCOMITANT DISEASE> | | |
| LUNG CANCER | 2 | |
| NON-TUBERCULOUS MYCOBACTERIOSIS | 1 | 750 |
| CRYPTOCOCCOSIS | 6 | |
| NEOPLASTIC | 13 | |
| LUNG CANCER | 10 | |
| METASTATIC LUNG CANCER | 3 | |
| NONNEOPLASTIC | 6 | |
| LUNG ABSCESS | 4 | |
| SARCOIDOSIS | 1 | |
| SEPTIC EMBOLUS | 1 | |
| MYCOBACTERIOSIS | 6 | |
| NON-TUBERCULOUS MYCOBACTERIOSIS | 4 | |
| LUNG PHTHISIS | 2 | |
| OTHERS | 2 | |
| BRONCHIAL ECTASIA | 1 | |
| ... | | |

DIFFERENT SLICE IMAGES FOR SAME CASE

| | |
|---|---|
| SIMILAR CASE ID | SIM5232 |
| REGION-OF-INTEREST COUNT | 2 |
| THUMBNAIL IMAGE DATA | (I0, 0, I0, 1, ···, Iw−1, h−1) |
| DEFINITIVE DIAGNOSIS COUNT | 2 |
| DISEASE ID | DIS012_007, DIS015_019 |

- 4100 — SIMILAR CASE ID
- 4200 — REGION-OF-INTEREST COUNT
- 4300 — THUMBNAIL IMAGE DATA
- 4400 — DEFINITIVE DIAGNOSIS COUNT
- 4500 — DISEASE ID

| | |
|---|---|
| REGION-OF-INTEREST ID | SIM5232_0 |
| SLICE ID | CT149391025 |
| REGION-OF-INTEREST COORDINATES | xSIM5232_0,l, ySIM5232_0,t, xSIM5232_0,r, ySIM5232_0,b |
| IMAGE FEATURE DATA | fSIM5232_0,0, fSIM5232_0,1, fSIM5232_0,2, ..., fSIM5232_0,N |
| IMAGING FINDINGS ID | CAT3, CAT7 |

| | |
|---|---|
| REGION-OF-INTEREST ID | SIM5232_1 |
| SLICE ID | CT149391029 |
| REGION-OF-INTEREST COORDINATES | xSIM5232_1,l, ySIM5232_1,t, xSIM5232_1,r, ySIM5232_1,b |
| IMAGE FEATURE DATA | fSIM5232_1,0, fSIM5232_1,1, fSIM5232_1,2, ..., fSIM5232_1,N |
| IMAGING FINDINGS ID | CAT3 |

- 4600 — REGION-OF-INTEREST ID
- 4700 — SLICE ID
- 4800 — REGION-OF-INTEREST COORDINATES
- 4900 — IMAGE FEATURE DATA
- 4950 — IMAGING FINDINGS ID

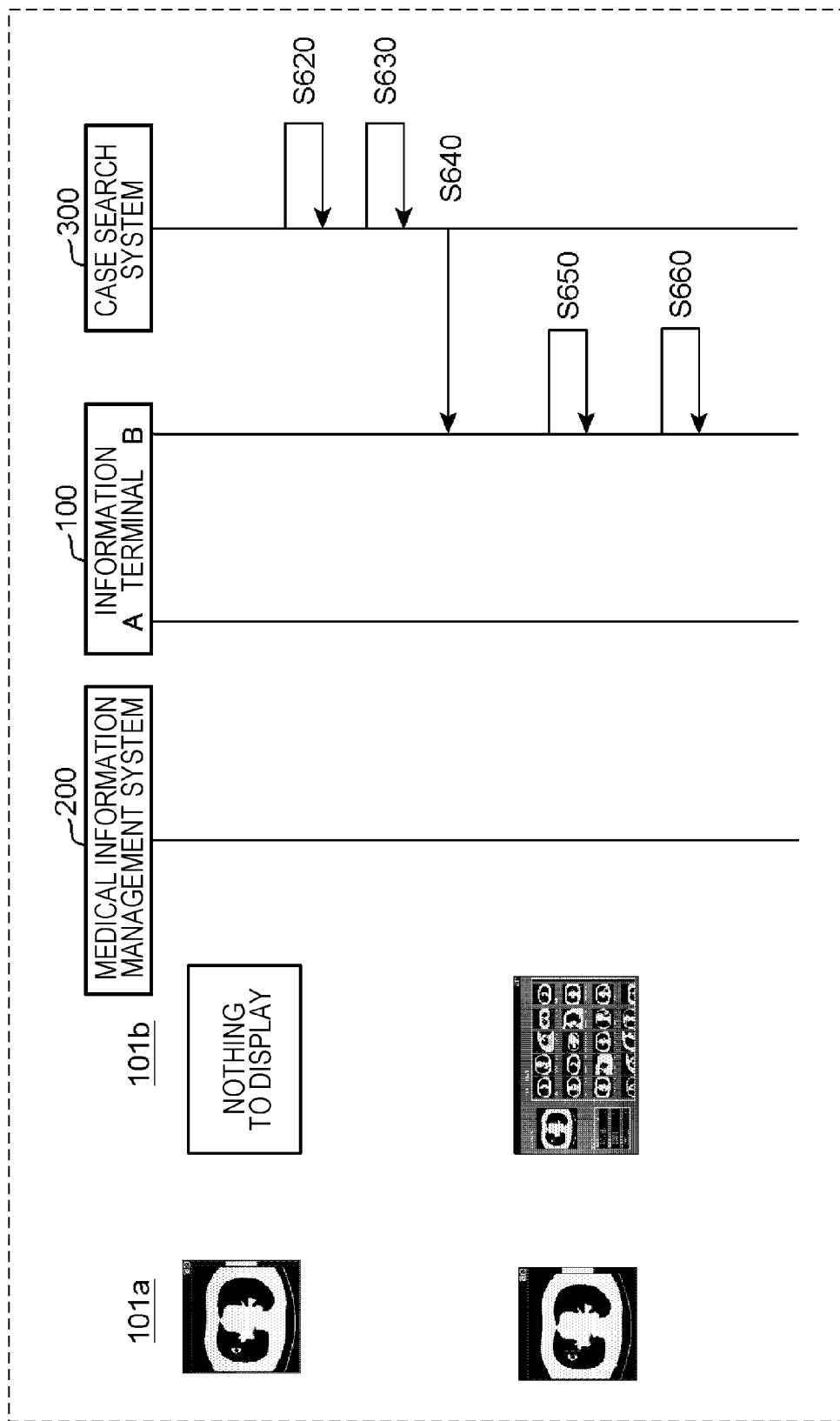

METHOD AND RECORDING MEDIUM

BACKGROUND

1. Technical Field

The present disclosure relates to a method for controlling an information terminal used to search for a medical image similar to a medical image to be interpreted and a recording medium.

2. Description of the Related Art

In recent years, medical imaging devices, such as computed tomography (CT) and magnetic resonance imaging (MRI) scanners, have been developed and have been widely used. Such CT and MRI allow digital, high-definition, and high-capacity medical images to be obtained. In addition, the medical images that has been interpreted by medical doctors have been gradually accumulated in Picture Archiving and Communication Systems (PACS) together with image interpretation reports. In addition, as described in, for example, Japanese Unexamined Patent Application Publication No. 2008-257292, development of a technology for searching past cases accumulated in PACS to find the best match between a new medical image to be interpreted and individual past medical images has been just started.

SUMMARY

One non-limiting and exemplary embodiment provides a medical imaging apparatus achieved by improving existing medical imaging apparatuses.

In one general aspect, the techniques disclosed here feature a method for controlling an information terminal including a display by connecting the information terminal to a case search system. The case search system searches a medical image database having medical images registered therein. The method includes causing a computer of the information terminal to detect designation information indicating at least one region of interest set in a medical image to be interpreted, causing the computer to receive, from the case search system, a plurality of similar medical images each having a predetermined similarity to a feature of the region of interest indicated by the designation information, where each of the similar medical images has information indicating at least one disease name, and causing the computer to display, on the display, a display screen including a first display area that presents the similar medical images and a second display area that is used to select a disease name. If the designation information indicates one region of interest, a list based on the information indicating at least one disease name is displayed in the second display area. If the designation information indicates two or more regions of interest, a concomitant disease name combination list based on the information indicating at least one disease name is displayed in the second display area.

It should be noted that general or specific embodiments may be implemented as a system, a method, an integrated circuit, a computer program, a computer-readable recording medium, or any selective combination thereof. Examples of the computer-readable recording medium includes a non-volatile recording medium, such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 11 illustrates the data structure of patient information;

FIG. 12 illustrates the data structure of test information registered in the patient information illustrated in FIG. 11;

FIG. 14 illustrates the data structure of a diagnosis report;

FIG. 18 illustrates the screen of a test list;

FIG. 19 illustrates the screen of a test list after the test is selected;

FIG. 23 illustrates a method for comparing image feature sets when each of the number of regions of interest (the number of image feature sets) of the search query image and the number of regions of interest (the number of image feature sets) in the similar case to be compared is equal to 2;

FIG. 24 illustrates a method for comparing the image feature sets when the number of regions of interest (the number of image feature sets) of the search query image is equal to 2 and the number of regions of interest (the number of image feature sets) in the similar case to be compared is equal to 3;

FIG. 27 illustrates an example of disease name list information;

FIG. 28 illustrates an example of the disease name list information;

FIG. 29 illustrates an example of the disease name list information;

FIG. 30 illustrates an example of concomitant disease name list information;

FIG. 31 illustrates a first display example of a disease name list display area;

FIG. 32 illustrates a second display example of the disease name list display area;

FIG. 33 illustrates a third display example of the disease name list display area;

FIG. 36 illustrates the data structure of a disease classification system stored in a disease classification system definition unit;

FIG. 41 illustrates a fifth example of the concomitant disease name list;

FIG. 62 illustrates the data structure of similar case data according to the second exemplary embodiment;

FIG. 70 is a sequence diagram illustrating a process performed after the case search system receives a request for a similar case search until the case search system returns the result of the similar case search to the information terminal.

DETAILED DESCRIPTION

Underlying Knowledge Forming Basis of the Present Disclosure

How the inventors conceptualized the aspects of the present disclosure below is described first.

In the following description, the lung is used as an organ, and CT is used as image modality. However, the organ and the image modality of the present disclosure are not limited thereto. The present disclosure is applicable to other organs and other image modalities.

By using image modality, organic lesion is observable. There is a relationship between the form (the appearance) of lesion and a disease. Accordingly, a radiologist carefully observes and examines the captured image and, thereafter, identifies the name of a disease affecting a patient. At that time, if a plurality of types of lesion are observed, the radiologist needs to determine whether the lesion is caused by a single disease or a plurality of different diseases.

Japanese Unexamined Patent Application Publication No. 2008-257292 describes an image diagnosis support system that presents case images useful for identifying a disease when image diagnosis is performed on the basis of an image to be diagnosed or the statistical information regarding the disease. The screen of the image diagnosis support system that displays the search result includes the image to be interpreted and the information regarding a typical case for each of the diseases. More specifically, the screen that displays the search result includes i) the images of typical cases of top three possible diseases A, D, and G, ii) the similarity of the image to be interpreted to each of the images for the diseases, the number of the registered cases and the number of typical cases, iii) the number of hit cases (the number of hit diseases), and iv) soft button "Next Page" for displaying the information regarding another disease which is unable to be displayed in the current screen (refer to Paragraphs [0062] and [0063] and FIG. 6(E)).

Figures 7, 8:
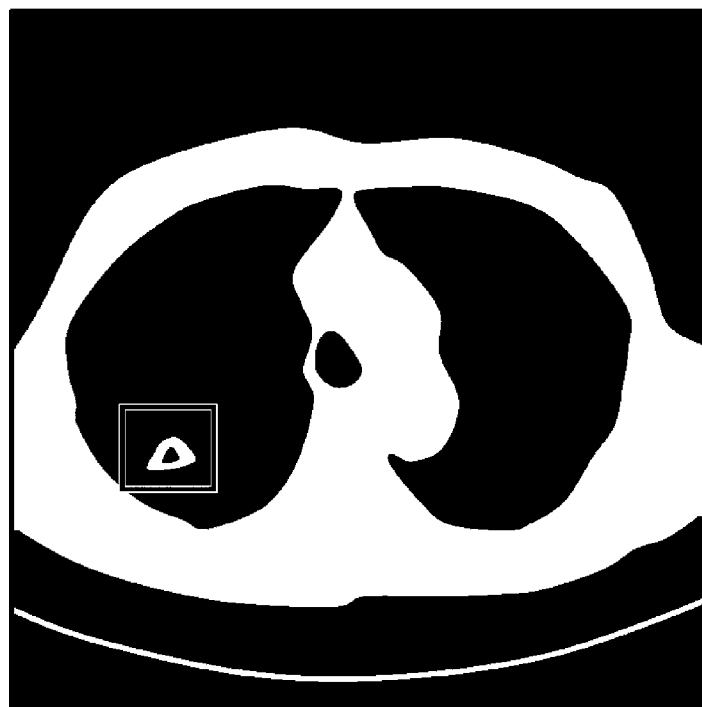
FIG. 7 illustrates the display area of selected one of similar cases displayed in a case display area.
FIG. 8 is an enlarged view of a disease name list display area.

Japanese Unexamined Patent Application Publication No. 2010-79568 describes a data search system that classifies case data stored in a case database into a plurality of diagnosis groups on the basis of the definite diagnosis information and searches each of the diagnosis groups for the case data. More specifically, the screen that displays the result of search includes i) the image serving as the search result in each of diagnosis groups G3, G4, and G6 and ii) Tips (e.g., notes for the diagnosis) for each of the diagnosis groups (FIG. 7).

Japanese Unexamined Patent Application Publication No. 2014-39852 describes an information processing apparatus that determines a display format of similar case data on the basis of the level of difficulty of the course of medical treatment for the similar case to be searched for. For example, when the diagnosis is easy for a patient on their first visit, the number of similar cases to be displayed is decreased. In addition, medical reference information is displayed in the free display area generated by the decrease. In contrast, if the diagnosis is easy and there are past images, the number of images of similar cases is decreased, and the past images are displayed in the free display area generated by the decrease. More specifically, the search result screen displays i) cases [1] to [3] together with the similarity ranking and the name of disease in descending order of the similarity ranking (refer to FIG. 5).

Japanese Unexamined Patent Application Publication No. 2010-17410 describes a technique for referring to a statistical information database and searching for the statistical information related to the patient information or the medical state information attached to the image to be searched for or the similar case image. For example, the database contains the statistical information (the information related to the statistical information and the statistical information) regarding a disease A and frequent concomitant diseases (based on the number per 10 thousand patients) (refer to Paragraphs [0046] and [0047] and FIG. 3). At that time, the statistical information regarding a disease that is highly likely to accompany the disease A of the similar case image is determined to be the related statistical information and, thus, is extracted from the statistical information database.

Japanese Unexamined Patent Application Publication No. 2014-233611 describes a treatment decision support system that recognizes the state of progress of a disease to be diagnosed and develops the treatment plan using the medical image of the similar case search result. In particular, if the information regarding a concomitant disease is contained in the information regarding the similar case image, the information regarding the concomitant disease is displayed at the same time (refer to Paragraph [0075]).

In each of Japanese Unexamined Patent Application Publication Nos. 2008-257292, 2010-79568, and 2014-39852, the information regarding a pair consisting of the case image for each of the diseases and the name of the disease is displayed. By comparing the image to be interpreted with each of the similar case images, the determination as to whether the case to be diagnosed is likely to correspond to the disease can be facilitated. However, the determination of a concomitant disease is not sufficiently supported.

In Japanese Unexamined Patent Application Publication No. 2010-17410, the system can provide an alert indicating whether the case to be diagnosed is related to a plurality of diseases by using the name of the disease of a similar case and the statistical information database. However, a lesion image pattern obtained when a patient has only one disease differs from that when the patient has a plurality of diseases including the disease. Accordingly, instead of providing the statistical information regarding a single disease, it is desirable that concomitant disease information corresponding to the image to be interpreted be additionally provided.

In Japanese Unexamined Patent Application Publication No. 2014-233611, the system can provide an alert indicating whether the case to be diagnosed is related to a plurality of diseases by referring to the name of the concomitant disease attached to a similar case. However, since the name of the concomitant disease is attached to an individual similar case, it is difficult to obtain the trend of the concomitant diseases across a plurality of search results.

Through the above-described study, the present inventors conceived the idea of the following aspects of the present disclosure.

According to an aspect of the present disclosure, a method for controlling an information terminal including a display by connecting the information terminal to a case search system is provided. The case search system searches the medical image database having medical images registered therein. The method includes causing a computer of the information terminal to detect designation information indicating at least one region of interest set in a medical image to be interpreted, causing the computer to receive, from the case search system, a plurality of similar medical images each having a predetermined similarity to a feature of the region of interest indicated by the designation information, where each of the similar medical images has information indicating at least one disease name, and causing the computer to display, on the display, a display screen including a first display area that presents the similar medical images and a second display area that is used to select a disease name.

If the designation information indicates one region of interest, a list based on the information indicating at least one disease name is displayed in the second display area.

If the designation information indicates two or more regions of interest, a concomitant disease name combination list based on the information indicating at least one disease name is displayed in the second display area.

According to the aspect, if the designation information indicates two or more regions of interest, a concomitant disease name combination list based on the information indicating at least one disease name is displayed. In this manner, when the medical image to be interpreted is highly likely to suggest that a plurality of diseases occur, the radiologist can easily find concomitant diseases in the past cases that are similar to the image to be interpreted.

In addition, according to the aspect, if the designation information indicates one region of interest, a list based on the information indicating at least one disease name is displayed. That is, according to the aspect, only when the designation information indicates a plurality of regions of interest, a concomitant disease name combination list is displayed. Thus, according to the aspect, the physician can focus on diagnosis of a single disease.

The concomitant disease name combination list may be inserted into the list.

The information indicating at least one disease name may include a similar medical image included in similar case data that includes information for identifying one disease name and that does not include information for identifying a plurality of disease names and a similar medical image included in similar case data that includes information for identifying the plurality of disease names.

If the designation information indicates one region of interest, a list may be displayed based on the similar medical image included in the similar case data that includes information for identifying the one disease name and that does not include information for identifying a plurality of disease names. If the designation information indicates two or more regions of interest, a concomitant disease name combination list may be displayed based on similar medical images included in the similar case data including the information for identifying a plurality of disease names.

In addition, according to the above-described aspect, a condition to display the disease name combination list in the second display area may be that the designation information indicates two or more regions of interest and that two or more types of imaging finding are included in the two or more regions of interest.

According to the present aspect, even when the designation information indicates two or more regions of interest, the combination list is not displayed if the imaging findings of the same type are included in the two or more regions of interest. Thus, the physician can focus on diagnosis of a single disease.

According to another aspect of the present disclosure, a method for controlling an information terminal including a display by connecting the information terminal to a case search system is provided. The case search system searches a medical image database having medical images registered therein. The method includes causing a computer of the information terminal to detect designation information indicating a region of interest set in a medical image to be interpreted, causing the computer to detect designation information indicating at least one imaging finding in the medical image to be interpreted, causing the computer to receive, from the case search system in accordance with a region of interest indicated by the designation information and the imaging finding indicated by the designation information, a plurality of similar medical images each having a predetermined similarity to a feature of the region of interest, where each of the similar medical images has information indicating at least one disease name, and causing the computer to display, on the display, a display screen including a first display area that presents the similar medical images and a second display area that is used to select a disease name.

If the designation information indicates one imaging finding, a list based on the information indicating at least one disease name is displayed in the second display area.

If the designation information indicates two or more imaging findings, a concomitant disease name combination list based on the information indicating at least one disease name is displayed in the second display area.

According to the present aspect, if search is conducted by specifying the plurality of imaging findings, the concomitant disease name combination list is displayed regardless of the number of regions of interest. Accordingly, the present disclosure can be applied to the case in which a plurality of imaging findings are specified for one region of interest.

In addition, according to the present aspect, if search is conducted by specifying one imaging finding, a list based on the information indicating at least one disease name is displayed. Thus, the present aspect allows a physician to focus on diagnosis of a single disease.

The information indicating at least one disease name may include a similar medical image included in similar case data that includes information for identifying one disease name and that does not include information for identifying a plurality of disease names and a similar medical image included in similar case data that includes the information for identifying a plurality of disease names.

If the designation information indicates one region of interest, a list may be displayed based on the similar medical image included in the similar case data that includes information for identifying one disease name and that does not include information for identifying a plurality of disease names. If the designation information indicates two or more regions of interest, a concomitant disease name combination list may be displayed based on similar medical images included in the similar case data including the information for identifying a plurality of disease names.

According to still another aspect of the present disclosure, a method for controlling an information terminal including a display by connecting the information terminal to a case search system is provided. The case search system searches a medical image database having medical images registered therein. The method includes causing a computer of the information terminal to detect designation information indicating a region of interest set in a medical image to be interpreted, causing the computer to receive, from the case search system in accordance with the region of interest indicated by the designation information, a plurality of similar medical images each having a predetermined similarity to a feature of the region of interest, where each of the similar medical images has information indicating at least one disease name, and causing the computer to display, on the display, a display screen including a first display area that presents the similar medical images, a second display area that is used to select a disease name, and a third display area used to select an imaging finding.

If one imaging finding is selected in the third display area, a list based on the information indicating at least one disease name is displayed in the second display area.

If two or more imaging findings are selected in the third display area, a concomitant disease name combination list based on the information indicating at least one disease name is displayed in the second display area.

According to the present aspect, if a plurality of imaging findings are specified as the narrowing condition, the concomitant disease name combination list is displayed regardless of the number of pieces of the designation information indicating a region of interest. Accordingly, the present disclosure can be applied to the case in which a plurality of imaging findings are specified for one region of interest.

In addition, according to the present aspect, when one imaging finding is specified as the narrowing condition, a list based on the information indicating at least one disease name is displayed. Accordingly, the preset aspect allows the physician to focus on diagnosis of a single disease.

The information indicating at least one disease name may include a similar medical image included in similar case data that includes information for identifying one disease name and that does not include information for identifying a plurality of disease names and a similar medical image included in similar case data that includes the information for identifying a plurality of disease names.

If the designation information indicates one region of interest, a list may be displayed based on the similar medical image included in the similar case data that includes information for identifying one disease name and that does not include information for identifying a plurality of disease names. If the designation information indicates two or more regions of interest, a concomitant disease name combination list may be displayed based on similar medical images included in the similar case data including the information for identifying a plurality of disease names.

In addition, according to the present aspect, the list in the second display area may present a plurality of disease names on the basis of the information for identifying one disease name and the information for identifying a plurality of disease names. If one of the presented disease names is selected, the similar medical image corresponding to the information for identifying the disease name corresponding to the selected disease name may be selected from among the plurality of similar medical images displayed in the first display area and may be displayed.

The information for identifying a plurality of disease names may include first information, and the first information may include second information for identifying a first disease name and third information for identifying a second disease name. The second disease name may be a first concomitant disease name, and the first concomitant disease name may be a name of a disease that occurs together with a disease identified by the first disease name.

When the first concomitant disease name is selected from the concomitant disease name combination list, the similar medical image included in the similar case data including the first information may be selected from among the similar medical images displayed in the first display area and may be displayed.

According to the present aspect, if a disease name in the combination list is selected, at least a similar medical image including a combination of the selected disease name is selected from among the similar medical images displayed in the first display area and is displayed. In this manner, selection and display of the similar case of a combination of diseases are facilitated. Thus, diagnosis as to whether a plurality of diseases occur in the case to be diagnosed can be facilitated.

The information for identifying a plurality of disease names may include first information, and the first information may include second information for identifying a first disease name and third information for identifying a second disease name. The second disease name may be a first concomitant disease name, and the first concomitant disease name may be a name of a disease that occurs together with a disease identified by the first disease name, and the number of the similar case data including the first information may be displayed.

Since the number of the similar medical images is displayed together with the disease name in the disease name list, it can be recognized, in the standalone disease name list, how many of what kind of diseases are acquired in the similar cases of the image to be interpreted. In the concomitant disease name list, it can be recognized how many of what kind of concomitant diseases are acquired, since the number of the similar medical images is displayed together with a pair of disease names.

The concomitant disease name combination list may display information indicating that there is a case in which no disease is concomitant with the disease identified by the first disease name.

By displaying the name of a disease occurring alone in the combination list, one of a set of at least one similar medical image corresponding to a disease occurring alone and a set of at least one similar medical image corresponding to a particular concomitant disease can be easily selected and displayed. Thus, it can be easily determined whether the case to be diagnosed is affected by a single disease or a plurality of diseases.

The concomitant disease name combination list may display the number of similar case data having no disease concomitant with the disease identified by the first disease name.

In addition, according to the above-described aspect, the computer of the information terminal may be caused to detect designation information indicating a region of interest set in a medical image to be interpreted, be caused to send information indicating a feature of the region of interest to the case search system, and be caused to receive, from the case search system, a similar medical image having the predetermined similarity to the feature of the region of interest.

Furthermore, according to the above-described aspect, the computer of the information terminal may be caused to detect designation information indicating a region of interest set in a medical image to be interpreted, be caused to send the medical image to be interpreted and the designation information to the case search system, and be caused to receive, from the case search system, a similar medical image having the predetermined similarity to the feature of the region of interest obtained from the medical image to be interpreted and the designation information.

Another aspect of the present disclosure is a method for an apparatus including a processor to execute a process, the process including: receiving information indicating two or more interested areas in a medical image; receiving similar case data items including one or more first similar case data items, one or more second similar case data items, and one or more third similar case data items, the similar case data items each including one or more similar medical case IDs indicating one or more similar medical images obtained through one medical examination, characteristic values of the two or more interested areas and one or more characteristic values of one or more portions included in the one or more similar medical images having predetermined relationship each of the one or more first similar case data items including first disease name ID indicating first disease name and not including second disease name ID indicating second disease name, the first disease name ID being different from the second disease name ID, the first disease name being different from the second disease name, each of the one or more second similar case data items including the second disease name ID and not including the first disease name ID, and each of the one or more third similar case data items including the first disease name ID and the second disease name ID, before the processor receives an instruction, displaying a first number with the first disease name and without the second disease name on a display, the first number being a sum of a total number of the one or more first similar case data items and a total number of the one or more third similar case data items; and after the processor receives an instruction, displaying, on the display, a second number with the second disease name and information indicating a disease by indicating the second disease name is concomitant disease to a disease by indicating the first disease name, the second number being the total number of the one or more third similar case data items, and still displaying the first number with the first disease name on the display, wherein the processor does not receive one or more similar case data items including the first disease name ID except the one or more first similar case data items and the one or more third similar case data items.

First Exemplary Embodiment

An exemplary embodiment of the present disclosure is described below with reference to the accompanying drawings. Note that the same reference numerals are used throughout the accompanying drawings and descriptions to refer to the same or similar constituent elements.

Figure 1:
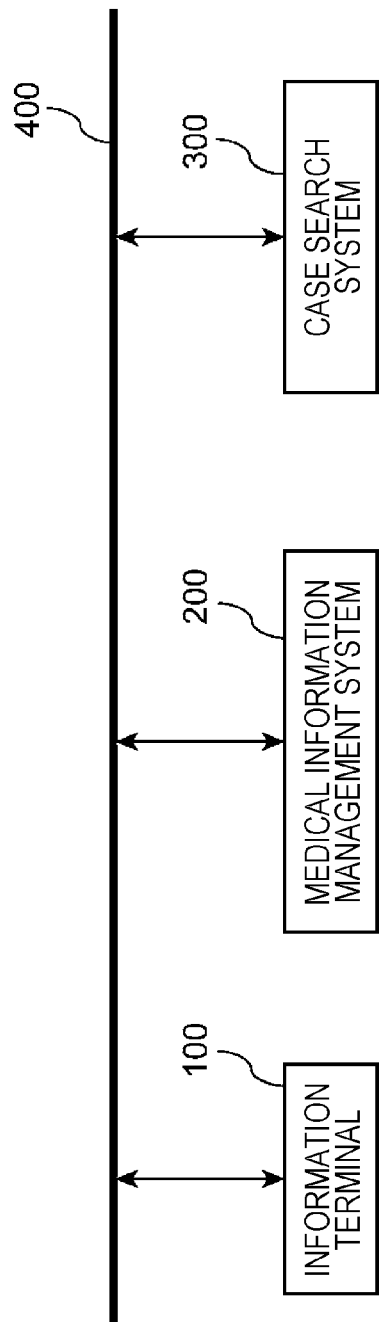
FIG. 1 is an overall configuration diagram of a hospital information system including an information terminal according to a first exemplary embodiment.

FIG. 1 is an overall configuration diagram of a hospital information system including an information terminal according to a first exemplary embodiment. As illustrated in FIG. 1, the hospital information system includes an information terminal 100, a medical information management system 200, and a case search system 300.

The information terminal 100, the medical information management system 200, and the case search system 300 are connected to one another via a network 400 for communication.

Note that the medical information management system 200 and the case search system 300 are not necessarily installed in a hospital. The medical information management system 200 and the case search system 300 may be software running in, for example, a data center, a private cloud server, or a public cloud server installed outside the hospital. If the medical information management system 200 and the case search system 300 are installed inside a hospital, a local area network can be used as the network 400. Examples of the network 400 include a wired LAN based on IEEE 802.3 standard, a wireless LAN based on IEEE 802.11 standard, and a network based on both the standards. If the medical information management system 200 and the case search system 300 are provided using a server located outside a hospital, the Internet is used as the network 400.

An information terminal, such as a personal computer or a tablet computer, can be used as the information terminal 100. Picture Archiving and Communication Systems (PACS) or an electronic health record system, for example, is used as the medical information management system 200.

Figure 2:
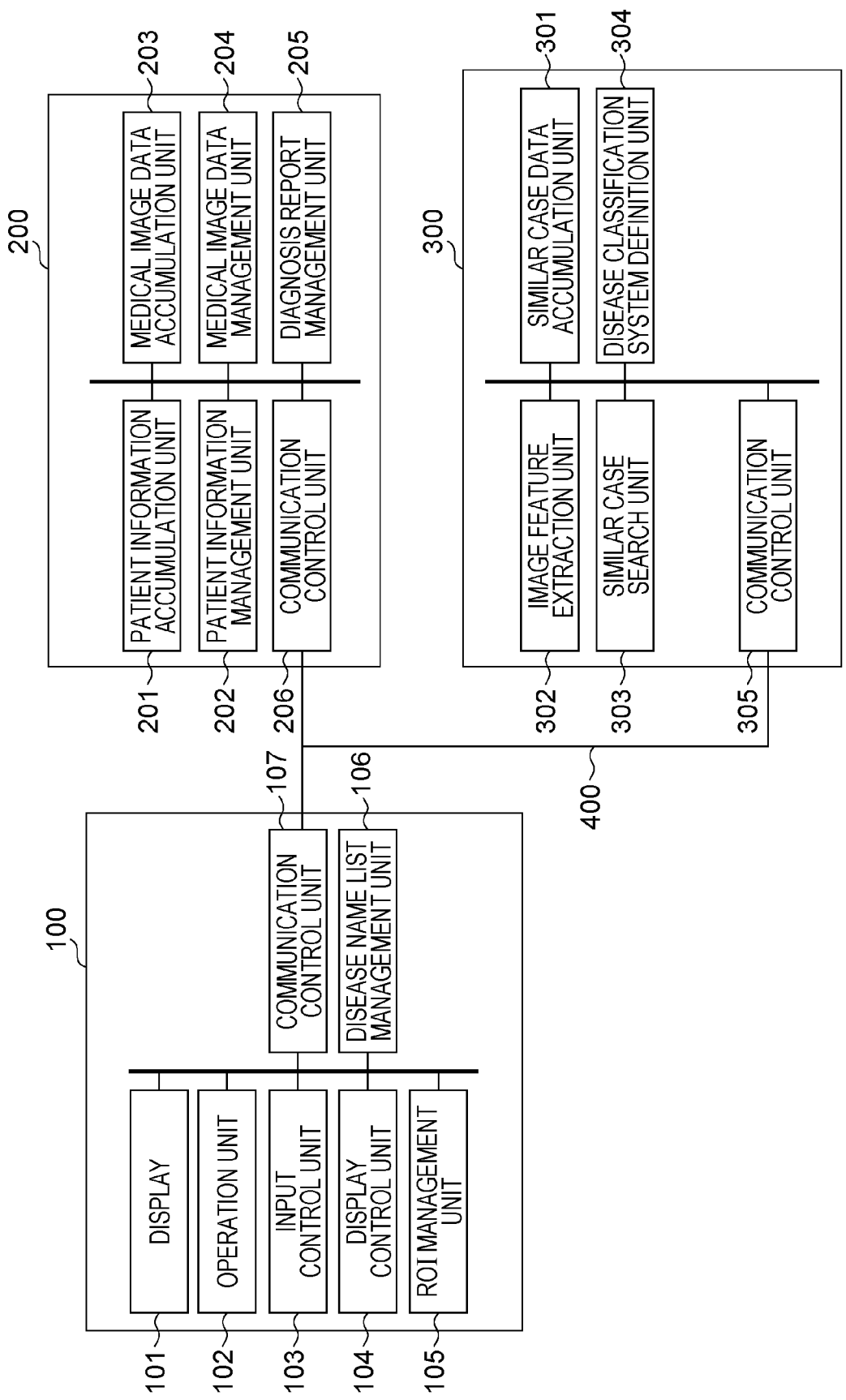
FIG. 2 is a block diagram illustrating the configurations of the information terminal, a medical information management system, and a case search system.

FIG. 2 is a block diagram illustrating the configurations of the information terminal 100, the medical information management system 200, and the case search system 300. As illustrated in FIG. 2, the information terminal 100 includes a display 101, an operation unit 102, an input control unit 103, a display control unit 104, an ROI management unit 105, a disease name list management unit 106, and a communication control unit 107.

The display 101 is formed from, for example, a liquid crystal monitor. The display 101 displays a medical image to be diagnosed and a medical record image. In addition, the display 101 displays a report input image used to input the result of a diagnosis. At least one display 101 is necessary. In general, two or three displays 101 are used for diagnostic imaging. According to the present exemplary embodiment, two displays 101 are used. One of the two displays 101 is referred to as a display 101a, and the other is referred to as a display 101b (refer to FIG. 3).

Figure 3:
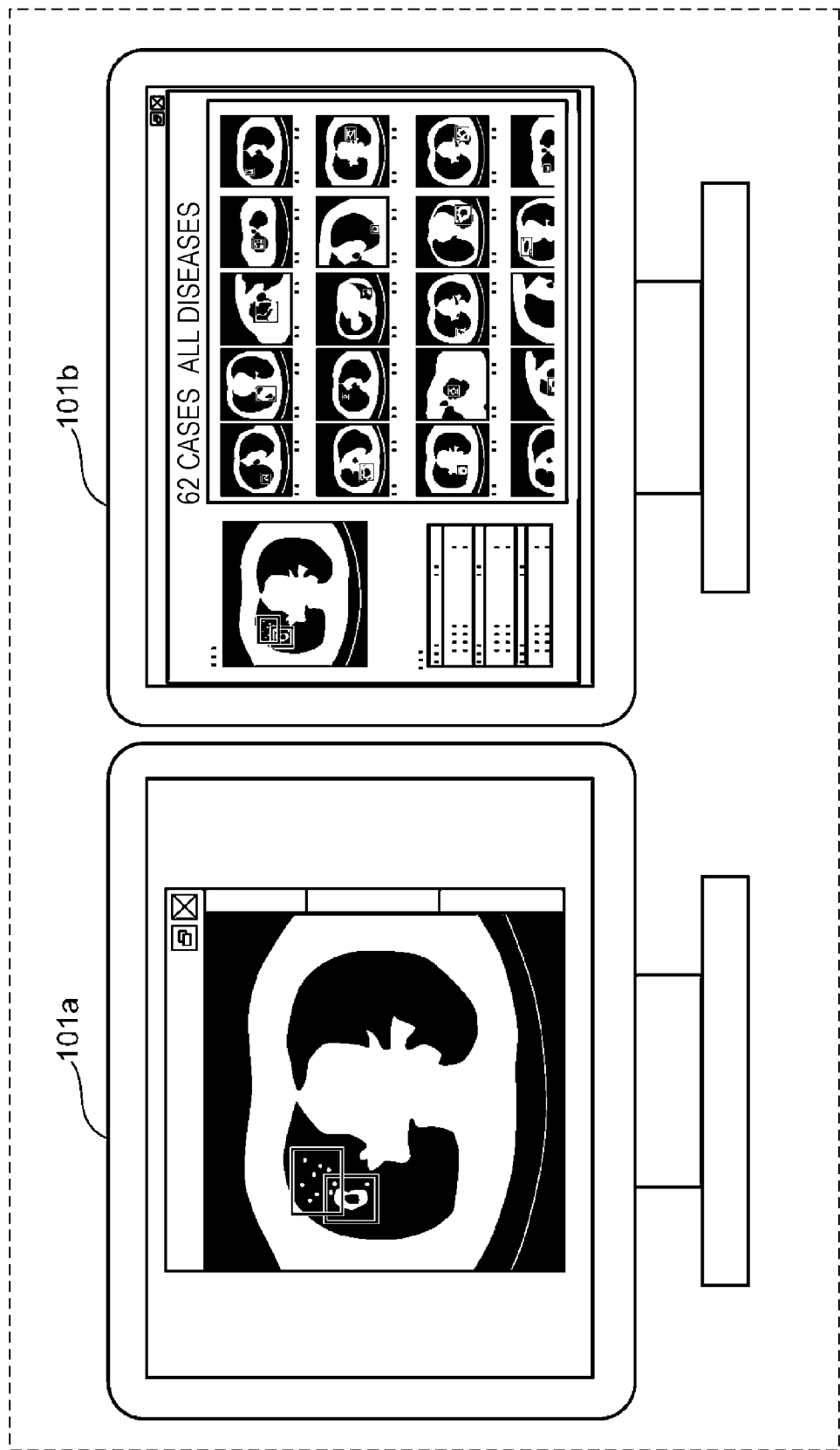
FIG. 3 is an external view of two displays.

FIG. 3 is an external view of the displays 101a and 101b. On the display 101a, an image of the case to be diagnosed acquired from the medical information management system 200 by the information terminal 100 is displayed in a medical image viewer. On the display 101b, the screen of the case search system 300 is displayed. Note that if only one display 101 is used, the two screens are displayed in two regions of the display screen of the display 101.

The operation unit 102 includes, for example, a keyboard and a mouse. The display 101 receives a variety of operations input to the information terminal 100 by a user. For example, the operation unit 102 receives operations performed by the user on a medical image and a medical record image displayed on the display 101 and operations performed by the user to input the result of a diagnosis to a report input screen.

Upon detecting an operation performed by the user on the operation unit 102, the input control unit 103 interprets the operation and sends the information about the operation to the other constituent elements. For example, the input control unit 103 detects the position of a mouse pointer on the display 101 from the coordinate data output from the mouse serving as the operation unit 102. Thereafter, the input control unit 103 displays the mouse pointer on the display 101. Subsequently, if, upon detecting a mouse click, a graphical user interface (GUI) component (e.g., a GUI button) generated by the display control unit 104 is displayed at the position at which the mouse pointer is displayed, the input control unit 103 determines that the user selects the GUI component. Thus, the input control unit 103 sends, to the other constituent elements, a message indicating that the GUI component is selected by the user.

The display control unit 104 generates a GUI of the information terminal 100 and instructs the display 101 to display the GUI.

Upon searching for similar cases, the ROI management unit 105 generates region-of-interest information indicating at least one region of interest set in a search query image (described in more detail below) and stores the region-of-interest information in a memory. In this manner, the ROI management unit 105 manages the region-of-interest information.

The disease name list management unit 106 stores, in the memory, disease name list information 6000 generated to display a disease name list display area 730 (refer to FIGS. 27, 28, and 29). In this manner, the disease name list management unit 106 manages the disease name list information 6000. The format of the disease name list and a technique for generating the disease name list are described below.

The communication control unit 107 includes a communication device that connects the information terminal 100 to the network 400. The communication control unit 107 controls communication between the information terminal 100 and the medical information management system 200 and between the information terminal 100 and the case search system 300. In addition, the communication control unit 107 receives a variety of data transmission requests from other blocks and transmits the data to the medical information management system 200 or the case search system 300. Furthermore, the communication control unit 107 receives data transmitted from the medical information management system 200 or the case search system 300 and delivers the data to a corresponding block.

As illustrated in FIG. 2, the medical information management system 200 includes a patient information accumulation unit 201, a patient information management unit 202, a medical image data accumulation unit 203, a medical image data management unit 204, a diagnosis report management unit 205, and a communication control unit 206.

The patient information accumulation unit 201 accumulates patient information 1000 (refer to FIG. 11). The patient information 1000 includes patient personal information, such as the gender and the age, clinical information, such as a past medical history, and test information, such as blood test information.

The patient information management unit 202 update the patient information 1000 (refer to FIG. 11) accumulated in the patient information accumulation unit 201 by registering data input by the user in the patient information 1000. In addition, the patient information management unit 202 outputs the patient information 1000 to the display control unit 104. In this manner, the patient information management unit 202 manages the patient information 1000. The medical image data accumulation unit 203 accumulates medical image data, that is, images of a patient for image diagnosis.

The medical image data management unit 204 accumulates medical image data in the medical image data accumulation unit 203 and manages the medical image data.

The diagnosis report management unit 205 manages a diagnosis report 3000 (refer to FIG. 14) indicating a medical diagnosis given to each of tests for a patient by a physician.

The communication control unit 206 includes, for example, a communication device that connects the medical information management system 200 to the network 400. The communication control unit 206 receives a variety of data transmission requests from other blocks and transmits the data to the information terminal 100 or the case search system 300. In addition, the communication control unit 206 receives data transmitted from the information terminal 100 or the case search system 300 and delivers the data to a corresponding block.

As illustrated in FIG. 2, the case search system 300 includes a similar case data accumulation unit 301, an image feature extraction unit 302, a similar case search unit 303, a disease classification system definition unit 304, and a communication control unit 305.

The similar case data accumulation unit 301 accumulates similar case data 4000 (refer to FIG. 15) in advance. The similar case data 4000 include the image features extracted from a plurality of similar cases selected as target data for similar case search among the similar cases managed by the medical information management system 200 and generated thumbnail images.

The image feature extraction unit 302 extracts the image feature from a region of interest indicated by the region-of-interest information regarding a search query image transmitted from the communication control unit 107 of the information terminal 100. Note that the region-of-interest information is an example of designation information indicating one or more regions of interest. The image feature extraction unit 302 extracts the image feature from each of all of the regions of interest designated by the region-of-interest information.

The similar case search unit 303 compares the image feature extracted by the image feature extraction unit 302 with the image feature of each of the similar cases accumulated in the similar case data accumulation unit 301 and generates a similar case search result. Note that the number of the image features extracted by the image feature extraction unit 302 is not necessarily the same as the number of the image features of the case accumulated in the similar case data accumulation unit 301, since the number of the regions of interest set for each of the cases may differ from each other. A search method used when the numbers of the image features are not the same is described below.

The disease classification system definition unit 304 defines a disease classification system 5000 (refer to FIG. 36). The term "disease classification system" refers to a classification system for disease IDs 4500 accumulated in the similar case data 4000 (refer to FIG. 15). More specifically, as illustrated in FIG. 36, the disease classification system 5000 stores a disease ID, a large category disease name, and small category disease name associated with one another. The disease ID begins with alphabetical characters "DIS" and is followed by a three-digit ID indicating the large category and a three-digit ID indicating the small category. By using such a format for the disease ID, the disease ID can clearly indicate a parent and child relationship between the large category disease name and the small category disease name and a brotherly relationship among the small category name entries of the disease IDs. That is, by using the disease ID, a disease classification system can be defined.

Figure 15:
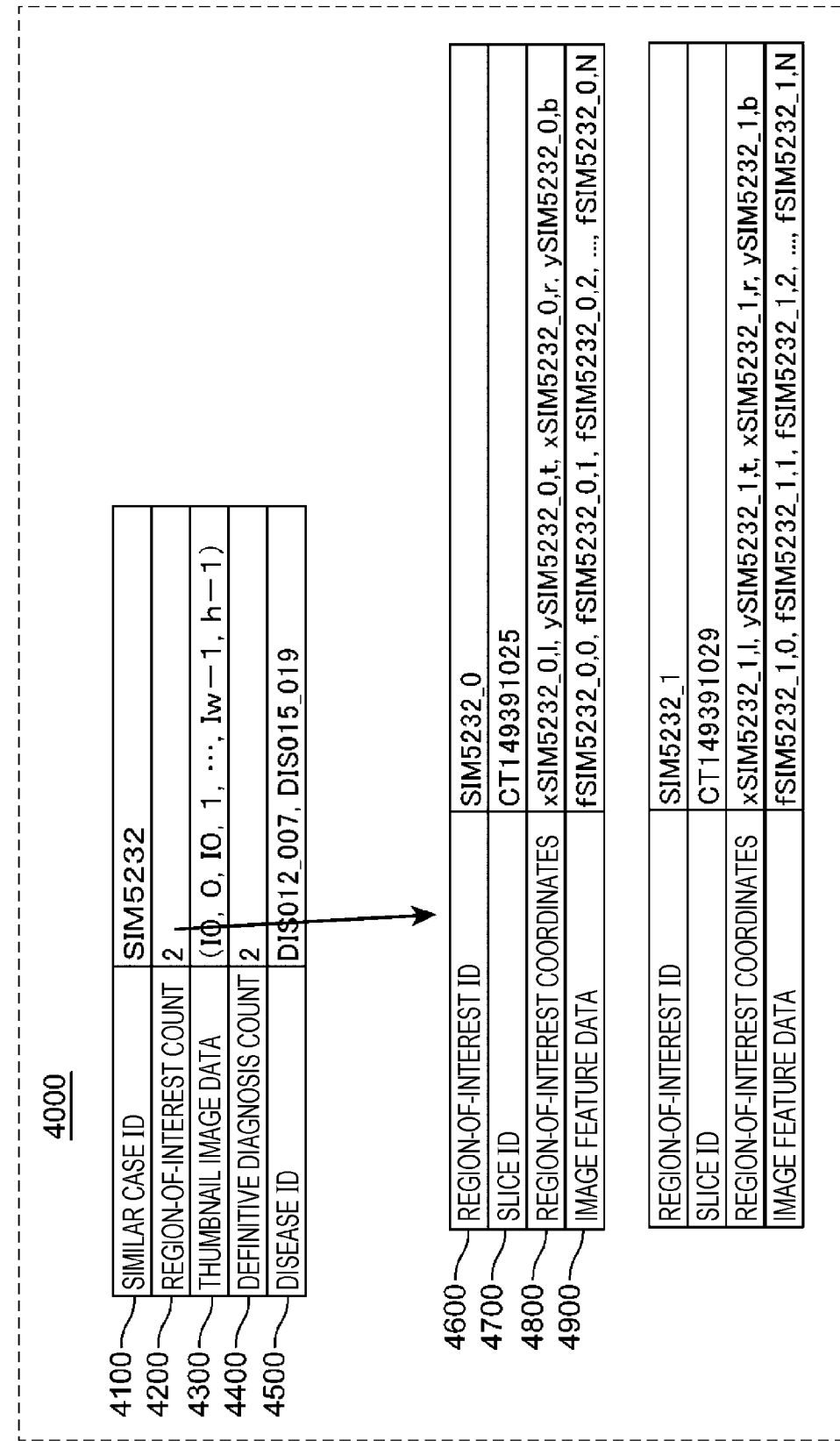
FIG. 15 illustrates the data structure of similar case data.

A disease ID is given to each of the cases on the basis of the patient information 1000 (refer to FIG. 11). More specifically, after a slice ID 4700 of a slice image set for a region of interest in the similar case data 4000 illustrated in FIG. 15 is acquired, a series ID 2100 is identified using a slice ID 2200 in a medical image database 2000 illustrated in FIG. 13. Thereafter, a test ID 1810 in test information 1800 (refer to FIG. 12) is identified using the identified series ID 2100. Subsequently, the patient information 1000 (refer to FIG. 11) is identified using the test ID 1810. Subsequently, a definite diagnosis 1900 for the patient is identified using the identified patient information 1000. The disease ID in the disease classification system 5000 (refer to FIG. 36) is identified using the definite diagnosis 1900 illustrated in FIG. 11. Thereafter, the identified disease ID is given as the disease ID 4500 in the similar case data 4000.

In this example, the disease classification system 5000 is used for similar case search.

The disease classification system 5000 is used to display, in the disease name list display area 730 (refer to FIG. 6), the list of definitively diagnosed disease names that were given to the plurality of similar case. In addition, the disease classification system 5000 is used to narrow down a search of a plurality of the similar cases by specifying a large category disease name or a small category disease names.

Note that the IDs of a large category disease name and a small category disease name defined by the disease classification system 5000 may be used to, for example, write a disease name to an electronic health record in addition to the similar case search.

The communication control unit 305 is formed from, for example, a communication device that connects the case search system 300 to the network 400. The communication control unit 305 receives a variety of data transmission requests from other blocks and transmits the data to the information terminal 100 or the medical information management system 200. In addition, the communication control unit 305 receives data transmitted from the information terminal 100 or the medical information management system 200 and delivers the data to a corresponding block.

Figure 4:
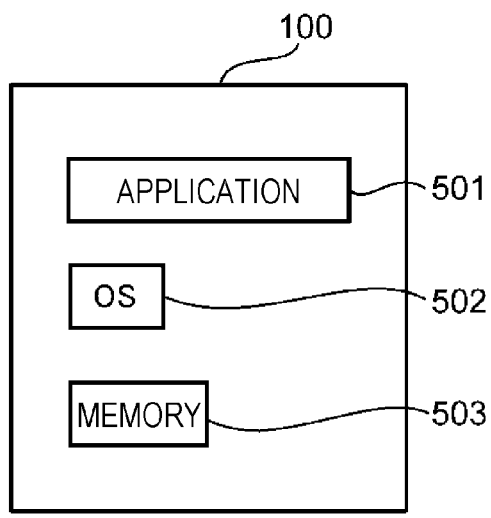
FIG. 4 illustrates an example of the configuration of the information terminal according to an exemplary embodiment.

FIG. 4 illustrates an example of the configuration of the information terminal 100 according to the present exemplary embodiment. As illustrated in FIG. 4, the information terminal 100 includes an application 501, an operating system (OS) 502, a memory 503, and other hardware (not illustrated).

The application 501 is application software for causing a personal computer or a tablet computer to function as the information terminal 100. The application 501 is executed by a processor of the information terminal 100. The information terminal 100 may read the application 501 from a computer-readable recording medium and install the application 501 therein. Alternatively, the information terminal 100 may install the application 501 by downloading the application 501 through a network.

The application 501 includes a medical information management application and a similar case search application. The medical information management application is an application that allows the information terminal 100 to cooperate with the medical information management system 200. The similar case search application is an application that allows the information terminal 100 to cooperate with the case search system 300. The two applications communicate data with each other to integrate services provided by the medical information management system 200 and the case search system 300 in the information terminal 100.

The OS 502 is basic software of the information terminal 100. The OS 502 is executed by the processor of the information terminal 100. The memory 503 is formed from storage units, such as a random access memory (RAM) and a read only memory (ROM), provided in the information terminal 100. The memory 503 stores data group contained in the application 501.

The processor of the information terminal 100 executes the application 501 to provide the functions of the input control unit 103, the display control unit 104, the ROI management unit 105, the disease name list management unit 106, and the communication control unit 107 illustrated in FIG. 2.

Note that the information terminal 100 may have only the application 501 installed or may have the application 501 and the OS 502 installed. Alternatively, the information terminal 100 may have the application 501, the OS 502, and the memory 503 installed or may have the application 501, the OS 502, the memory 503, and other hardware (not illustrated). Any one of the installation forms can achieve the information terminal 100 according to the present exemplary embodiment.

Figure 5:
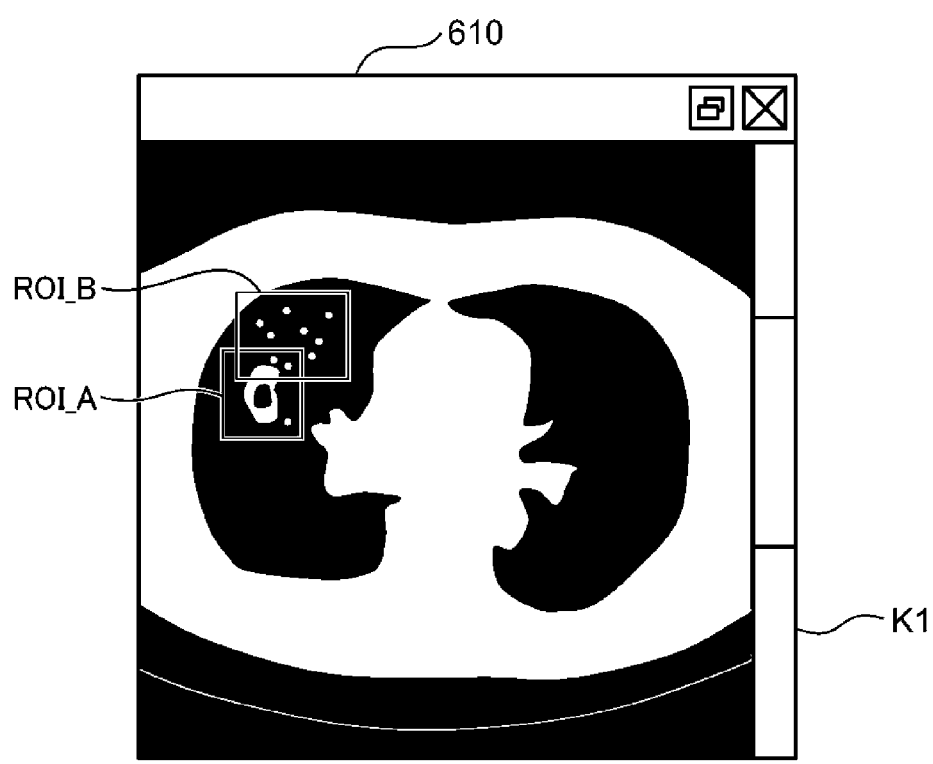
FIG. 5 illustrates an example of a basic screen displayed on the display of the information terminal immediately after a similar case search application is started in the information terminal.

FIG. 5 illustrates an example of a basic screen displayed on the display 101a of the information terminal 100. A basic screen K1 illustrated in FIG. 5 is formed from a medical image viewer 610. In general, a medical image is recorded in a Digital Imaging and Communication in Medicine (DICOM) format. The medical image viewer 610 is a viewer that can handle the DICOM format. According to the present exemplary embodiment, a medical image is a chest CT image formed from a plurality of tomographic images (hereinafter referred to as "slice images") in the DICOM format. However, the chest CT image is only illustrative, and the CT image may be an image obtained by capturing the image of another part of the body (e.g., the head, abdomen, leg, or arm).

Slice images of the chest CT image displayed by the medical image viewer 610 can be changed to other slice images by an operation using a mouse or keyboard. Note that the slice images that constitute the chest CT image are arranged in the order from the closest to the heart to the closest to abdomen, for example.

For example, the mouse pointer is positioned in the medical image viewer 610. Thereafter, the input control unit 103 detects rotation of a mouse wheel, the display control unit 104 changes the slice image displayed in the medical image viewer 610 to a new one in accordance with the detected amount of rotation. At that time, for example, when the mouse pointer is located in the medical image viewer 610 and if the mouse wheel is rotated rearward by one click, the display control unit 104 changes the currently displayed slice image to a slice image at the next slice position. In contrast, if the mouse wheel is rotated forward by one click, the display control unit 104 changes the currently displayed slice image to a slice image at the immediately previous slice position in the medical image viewer 610. Thus, the user (e.g., a physician) can appropriately change the slice image displayed in the medical image viewer 610 by rotating the mouse wheel forward or rearward to search for a desired slice image.

Note that the medical image may be a magnetic resonance imaging (MRI) chest image or a plain X-ray chest image instead of a chest CT image. In addition, while the example illustrated in FIG. 5 has been described with reference to one medical image viewer, the number of the medical image viewers is limited thereto. For example, two or three medical image viewers may be employed. If a plurality of the medical image viewers are being run simultaneously, other images captured in the test of the diagnosis target (e.g., an angiographic image or an image of another modality), an image under another display condition (a lung window setting or a mediastinal window setting), or the clinical images of the patient captured in past medical examinations can be simultaneously displayed. The number of images that can be simultaneously compared with one another increases with increasing number of the medical image viewer. However, the display area per image decreases. Accordingly, the number of medical image viewers can be appropriately determined in accordance with the display size of the display 101a. According to the present exemplary embodiment, the number of medical image viewers can be set to any number by the user or the administrator.

Before the similar case search application is started, the display 101a displays a slice image of the chest CT image of a given patient. At that time, a user, such as a reader, sets at least one region of interest (ROI) with which similar case search is to be performed. Subsequently, the similar case search application is started. Note that the display control unit 104 may display the region of interest with which similar case search is to be performed on the search query image in a superimposed manner. The search query image is an example of a medical image to be interpreted.

Figure 6:
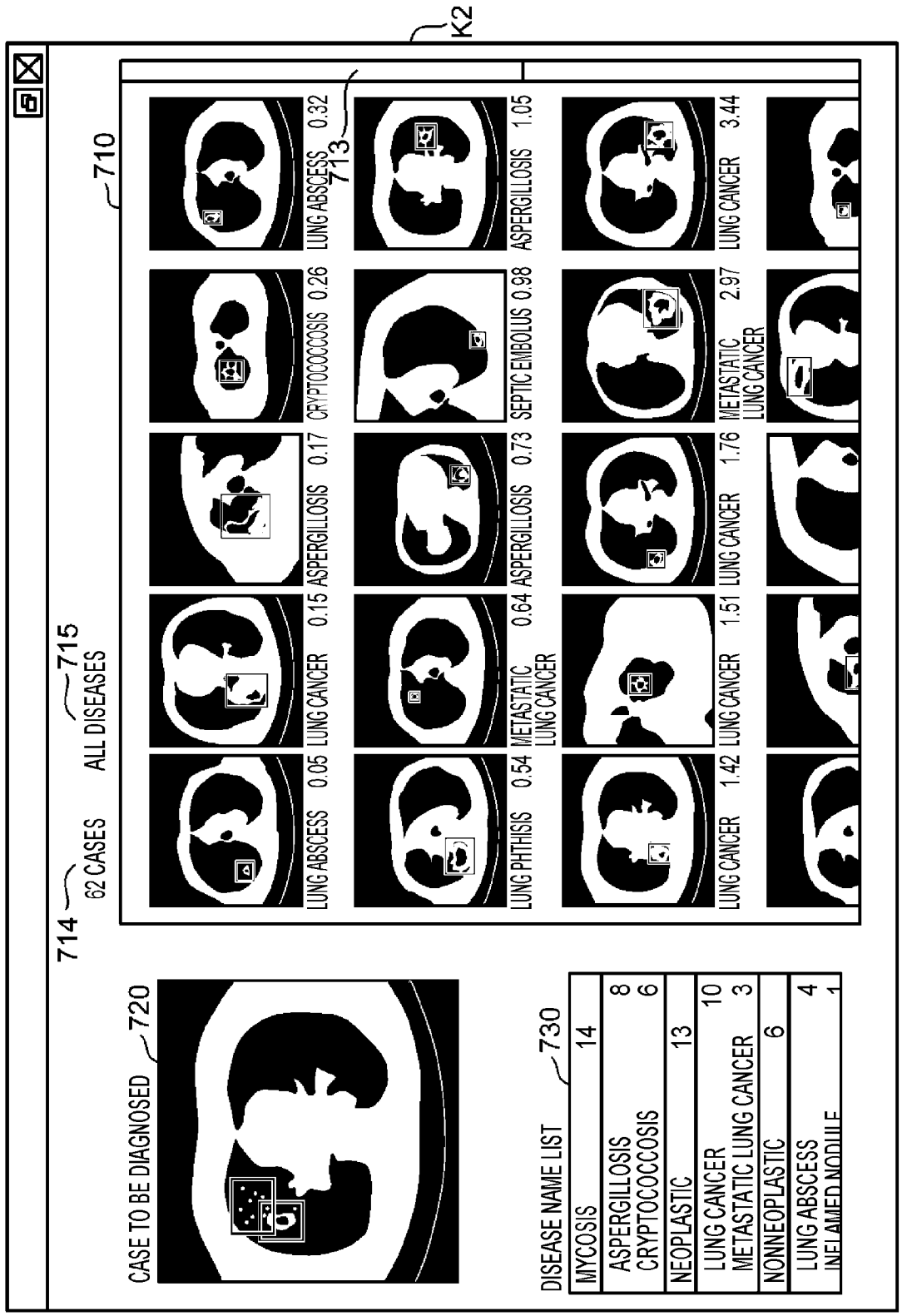
FIG. 6 illustrates an example of the basic screen displayed on the display immediately after the similar case search application is started in the information terminal.

FIG. 6 illustrates an example of a basic screen K2 displayed on the display 101b immediately after the similar case search application is started in the information terminal 100. The basic screen K2 illustrated in FIG. 6 includes a case display area 710, a case count display area 714, a disease condition display area 715, a diagnosis target image display area 720, and a disease name list display area 730. Note that the case display area 710 is an example of a first display area, and the disease name list display area 730 is an example of a second display area.

The case display area 710 is used to display thumbnail images of the similar cases that are similar to the search query image in the order from the highest to lowest similarity. Note that the thumbnail image of a similar case is an example of a similar medical image.

A plurality of similar cases are displayed in the case display area 710. Accordingly, if the resolution and the pixel values are converted at the display time, it takes a long time for processing. Thus, the thumbnail images are generated from the original slice images and are stored in the case search system 300 in advance.

The conversion of the resolution and pixel value is briefly described below. The original slice image has a resolution of 512×512 pixels. Since the thumbnail image has a resolution lower than that of the original slice image, conversion of the resolution is required. Accordingly, a low resolution process and a grayscale conversion process are performed on the original slice image to generate the thumbnail image.

For example, the grayscale conversion process is performed as follows. That is, a slice image obtained through CT has 2000 levels of grayscale (each of the pixel value (the CT value) is in the range from −1000 to +1000 HU (Hounsfield Unit)), which is difficult to be displayed on widely used 8-bit grayscale displays. Even when the slice image can be displayed on a display, it is difficult to distinguish among emphysema region (CT value: −1000 HU), a normal tissue in the lung field (CT value: about −900 HU), a field exhibiting ground glass opacity (CT value: −800 HU), a soft tissue (CT value: −100 to −50 HU), water (CT value: 0 HU), and the bone (CT value: 1000 HU) by the human eyes, since the slice images have only 2000 levels of grayscale.

Accordingly, in general, the window level and the window width are set for each of the pixel values of a slice image, and the slice image is re-configured with an 8-bit pixel value. Thereafter, the slice image is displayed. As used herein, the term "window level" refers to the CT value of the midpoint of the window, and the term "window width" refers to the minimum to maximum width at the center of which there is the window level.

For example, when a DICOM image is re-configured with the lung window settings, the window level is set to −550 to −800, and the window width is set to 1000 to 1600. Accordingly, the thumbnail image is generated from the original slice image through the above-described process so that the pixel values are in an 8-bit range.

Note that the thumbnail image displayed in the case display area 710 indicates a similar case having a distance from the feature vector of the case to be diagnosed that is less than or equal to a predetermined threshold value.

According to the present exemplary embodiment, Euclidean distance is used as the distance, for example. However, another distance scale, such as a city block distance, may be employed as the distance. Two images to be compared are more similar to each other with decreasing distance. In addition, the feature vector is not obtained from the thumbnail image but is obtained from the slice image, which is the original image.

The case count display area 714 is used to display the number of the cases displayed in the case display area 710. The disease condition display area 715 is used to display the disease names of the cases displayed in the case display area 710.

FIG. 7 illustrates the display area of selected one of the similar cases displayed in the case display area 710. The display area of the similar case contains the thumbnail image. In addition, the display area of the similar case contains a definitively diagnosed disease name display area 711 and a distance display area 712 under the thumbnail image. The definitively diagnosed disease name of the target similar case is displayed in the definitively diagnosed disease name display area 711. As used herein, the term "definitively diagnosed disease name" refers to the name of a disease of the target similar case that was definitively diagnosed. The distance display area 712 displays the distance between the feature vector of the slice image of the target similar case and the feature vector of the search query image. In the example illustrated in FIG. 7, the text "non-tuberculous mycobacteriosis" is displayed in the definitively diagnosed disease name display area 711. Accordingly, this thumbnail image is the thumbnail image of a similar case in which a definitive diagnosis of non-tuberculous mycobacteriosis was made. In addition, since the distance display area 712 displays "0.05", the distance between the slice image of the similar case and the slice image is 0.05.

Referring back to FIG. 6, the case count display area 714 is located, for example, above the case display area 710 in the basic screen K2. The case count display area 714 displays the number of the similar cases that are acquired from the case search system 300 as a result of the search process and that are similar to the case to be diagnosed.

Note that if the number of the similar case is huge, all the similar cases cannot be displayed in the case display area 710. Accordingly, for example, a scroll bar 713 that extends vertically is provided on the right of the case display area 710. The display control unit 104 vertically scrolls the thumbnail images displayed in the case display area 710 in accordance with the movement of the scroll bar 713. In this manner, the user can display, in the case display area 710, the similar cases that were hidden and, thus, can observe the similar cases.

Note that the scroll bar 713 may extend horizontally. In such a case, the display control unit 104 can horizontally scroll the thumbnail images displayed in the case display area 710 in accordance with the movement of the scroll bar 713. Alternatively, if an arrow key on the keyboard is depressed with the mouse pointer positioned in the case display area 710, the display control unit 104 may scroll the thumbnail images displayed in the case display area 710 in a direction of the arrow while the arrow key is being depressed.

Note that while the above description has been made with reference to the information terminal 100 that acquires, from the case search system 300, the thumbnail images each having a distance from the search query image that is less than or equal to a predetermined threshold value, such a technique is only illustrative. For example, the information terminal 100 may acquire, from the case search system 300, a certain number of high-similarity thumbnail images at all times. Alternatively, the information terminal 100 may acquire the thumbnail images from the case search system 300 so that a certain number of the thumbnail images for some definitively diagnosed disease name are included at all times.

Note that for example, to display the thumbnail images in the case display area 710, the thumbnail image having a minimum distance from the search query image can be displayed in the top row at the leftmost position. The other thumbnail images are arranged from the right position so that the distances thereof increase toward the right. If the row is full, the next thumbnail is placed in the second row at the leftmost position, and the other thumbnail images are arranged in the second row in the same manner. That is, the thumbnail images can be arranged in the case display area 710 from the upper left to the lower right in a meandering fashion in the order of ascending distance.

Note that according to the present exemplary embodiment, another technique for displaying the thumbnail images may be employed. For example, the thumbnail image having a minimum distance may be displayed in a first column at the uppermost position. The other thumbnail images are arranged from the next position in the column so that the distances thereof increase downward. If the column is full, the next thumbnail is placed in the second column at the uppermost position, and the other thumbnail images are arranged in the second column in the same manner. Alternatively, a configuration that allows the user to select one of the above-described two techniques for displaying the thumbnail images may be provided.

While the above-described example has been described with reference to a distance serving as the similarity, any index that indicates the similarity between images (e.g., the cosine similarity) may be employed. If the cosine similarity is employed, the similarity between two images to be compared is higher as the value of cosine similarity is closer to 1.

Note that the user can narrow down a search of the similar cases displayed in the case display area 710 by using the disease name displayed in the disease name list display area 730. The narrowing condition currently set for the similar cases is displayed in the disease condition display area 715. In the example illustrated in FIG. 6, the case display area 710 immediately after similar case search is performed is displayed. Since any narrowed search has not been conducted, "All diseases" is displayed in the disease condition display area 715.

As illustrated in FIG. 5, when the search query image is displayed in the medical image viewer 610, the thumbnail image of the search query image is displayed in the diagnosis target image display area 720 as an initial image.

The disease name list display area 730 with a title of "Disease Name List" is disposed in the lower left section of the basic screen K2 illustrated in FIG. 6. The disease name list display area 730 displays all the definitively diagnosed disease names of the similar cases acquired as the result of the similar case search. After a diagnosis is made and the definitively diagnosed disease name is given to the case to be diagnosed, the case to be diagnosed is accumulated in the case search system 300 as a similar case. Accordingly, each of the similar cases has a definitively diagnosed disease name associated therewith in advance.

FIG. 8 is an enlarged view of the disease name list display area 730. The basic operation and function of the disease name list display area 730 is described below. The operation and function of a concomitant disease name list which characterizes the present disclosure are described below. In FIG. 8, each of the definitively diagnosed disease names is displayed as either a large category disease name (731, 734, 737, 741, 744) or a small category disease name (732, 733, 735, 736, 738, 739, 740, 742, 743, 745). In the example illustrated in FIG. 8, the displayed large category disease names include mycosis 731, neoplastic 734, nonneoplastic 737, mycobacteriosis 741, and others 744.

In addition, in the example illustrated in FIG. 8, aspergillosis 732 and cryptococcosis 733 are displayed as the small category disease names of mycosis 731. In addition, lung cancer 735 and metastatic lung cancer 736 are displayed as the small category names of neoplastic 734. In addition, lung abscess 738, sarcoidosis 739, and septic emboli 740 are displayed as the small category disease names of nonneoplastic 737. In addition, nontuberculous mycobacteria (NTM) 742 and tuberculosis 743 are displayed as the small category disease names of mycobacteriosis 741. Furthermore, bronchiectasis 745 is displayed as the displayed small category disease names of others 744.

Figure 9:
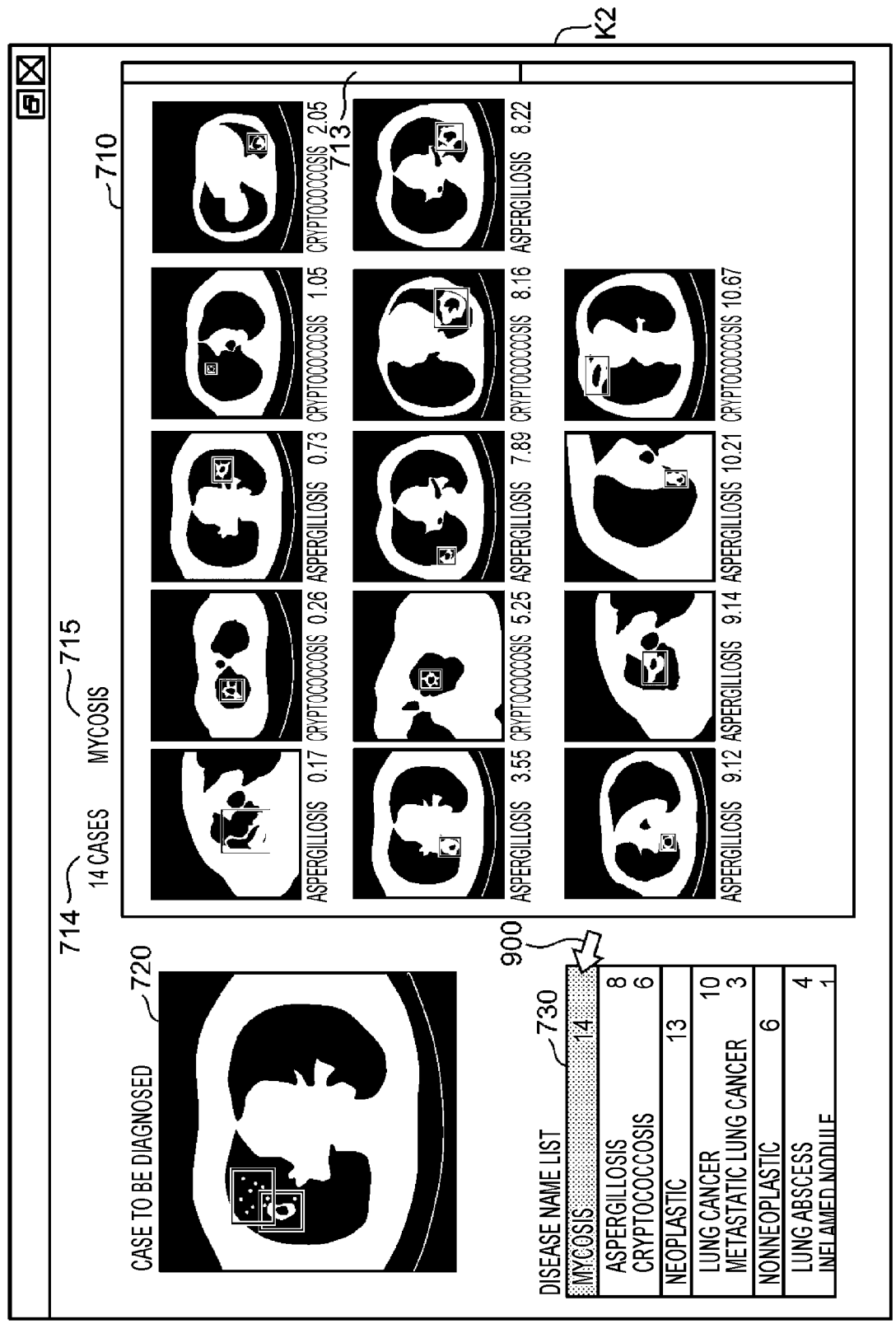
FIG. 9 illustrates the basic screen displayed after a narrowed search is conducted on the similar cases using "mycosis"
Figure 10:
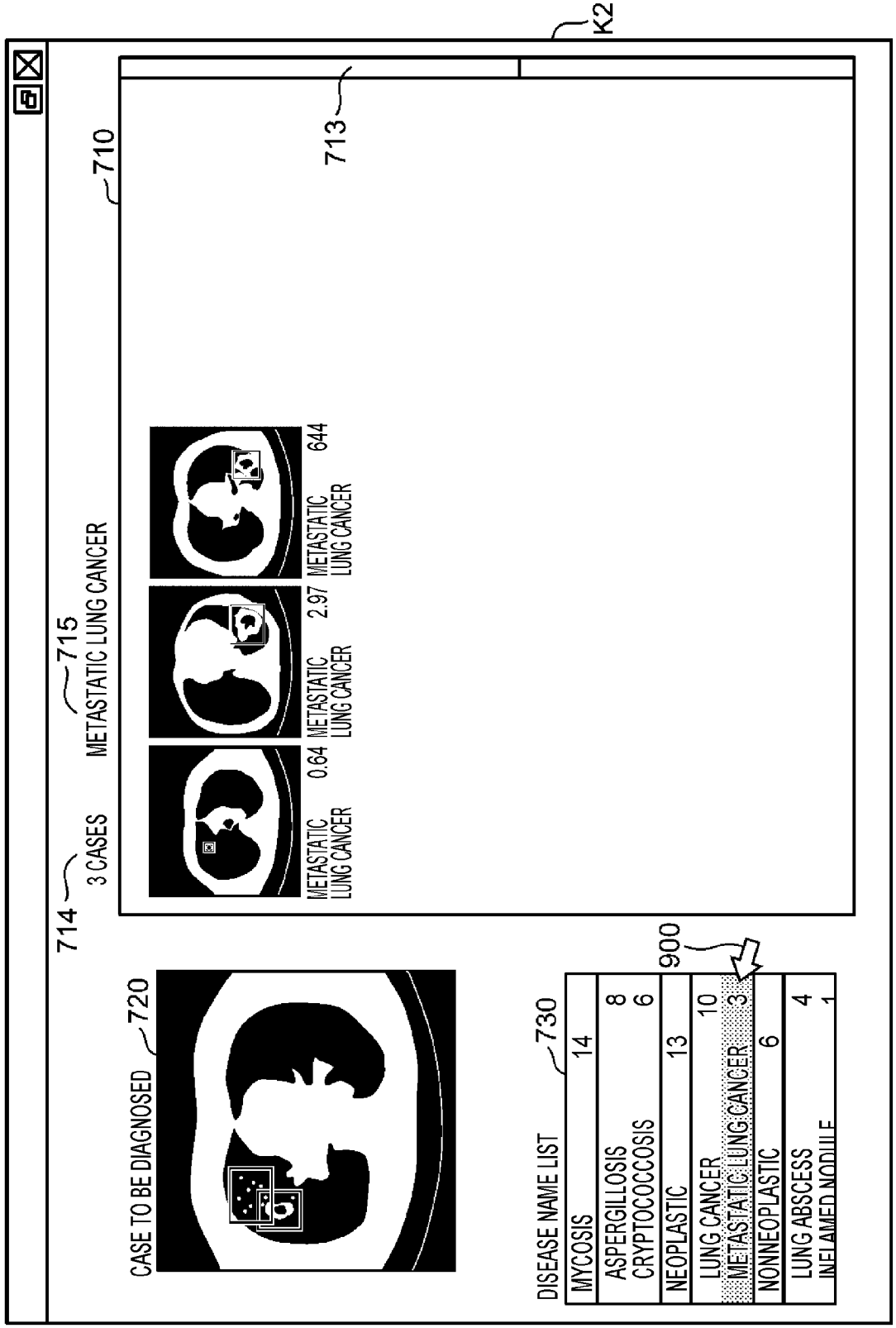
FIG. 10 illustrates the basic screen displayed after a narrowed search is conducted on the similar cases using "metastatic lung cancer"

In addition, the number of the cases for the disease name is displayed next to each of the large category disease names and small category disease names. The user can narrow a search of the similar cases displayed in the case display area 710 by selecting a desired row of the large category disease name or the small category disease name displayed in the disease name list display area 730. As illustrated in FIG. 6, immediately after a similar case search is conducted, 62 similar cases including a variety of diseases are displayed. If the row of mycosis 731 illustrated in FIG. 8 is clicked by the mouse, the display control unit 104 displays only the similar cases of mycosis in the case display area 710, as illustrated in FIG. 9. Alternatively, if the row of metastatic lung cancer 736 illustrated in FIG. 8 is clicked by the mouse, the display control unit 104 displays only the similar cases of metastatic lung cancer in the case display area 710, as illustrated in FIG. 10.

At that time, the display control unit 104 displays, in the disease condition display area 715, the disease name selected as the narrowing condition so that the user can recognize what narrowing condition leads to the similar cases currently displayed in the case display area 710. FIG. 9 illustrates the basic screen K2 displayed after a narrowed search is conducted on the similar cases using "mycosis". FIG. 10 illustrates the basic screen K2 displayed after a narrowed search is conducted on the similar cases using "metastatic lung cancer".

In the example illustrated in FIG. 9, since a narrowed search is conducted on the similar cases using "mycosis" (900), the word "mycosis" is displayed in the disease condition display area 715. In the example illustrated in FIG. 10, since a narrowed search is conducted on the similar cases using "metastatic lung cancer" (900), the word "metastatic lung cancer" is displayed in the disease condition display area 715.

In addition, at that time, the display control unit 104 displays the number of the similar cases in the case count display area 714 so that the user can recognize the number of the similar cases displayed in the case display area 710. In the example illustrated in FIG. 9, since the number of the similar cases of "mycosis" is equal to 14, the text "14 cases"

is displayed in the case count display area 714. In the example illustrated in FIG. 10, since the number of the similar cases of "metastatic lung cancer" is equal to 3, the text "3 cases" is displayed in the case count display area 714.

According to the function, the similar cases of only the disease that the physician selects as the target of the diagnostic imaging are displayed in the case display area 710. Thus, the physician can easily determine whether the case to be diagnosed matches the suspected disease.

FIG. 11 illustrates the data structure of the patient information 1000. The patient information 1000 is accumulated in the patient information accumulation unit 201 for each of patients by the patient information management unit 202 of the medical information management system 200. The patient information 1000 includes personal information of the patient, such as the gender and age, the clinical information, such as a personal medical history, and the test information, such as blood test information. As illustrated in FIG. 11, the patient information 1000 includes a patient ID 1100, a name 1200, an age 1300, a gender 1400, a personal medical history 1500, a family history 1600, major complaint 1700, test information 1800, and a definitive diagnosis 1900.

The patient ID 1100 is an identifier unique to the patient. The name 1200, the age 1300, the gender 1400, the personal medical history 1500, the family history 1600, and the major complaint 1700 are the name, the age, the gender, the personal medical history, the family history, and the major complaint of the patient having the patient ID 1100, respectively. As illustrated in FIG. 12, the test information 1800 includes information regarding one or more tests which the patient had taken.

FIG. 12 illustrates the data structure of the test information 1800 registered in the patient information 1000 illustrated in FIG. 11. The test information 1800 is generated for each of the tests which the patient had taken. The test information 1800 includes a test ID 1810, a test date and time 1820, a test type 1830, and a test result 1840. The test ID 1810 is an identifier unique to the test. The test date and time 1820 indicates the date and time on which the test is conducted. The test type 1830 indicates the type of test. Examples of the type of test include a blood test, a respiratory function test, an endoscopic test, plain X-ray imaging, and CT imaging.

In the case of a blood test, the test result 1840 indicates a variety of index values, such as a white count, LDH, and GPT. The test result 1840 also indicates the decision which the physician made on the basis of the variety of index values. In addition, in the case of an imaging test, such as the plain X-ray imaging or CT imaging, the test result 1840 includes the pointer information to the captured image and the pointer information to the report of the result of diagnostic imaging. Note that the image captured in the test is stored in the medical image data accumulation unit 203 of the medical information management system 200 in the DICOM format.

In addition, if the test type 1830 indicates one of, for example, plain X-ray, a CT, MRI, and PET imaging tests, the medical image data is accumulated in the medical image database 2000 stored in the medical image data accumulation unit 203 of the medical information management system 200.

Figure 13:
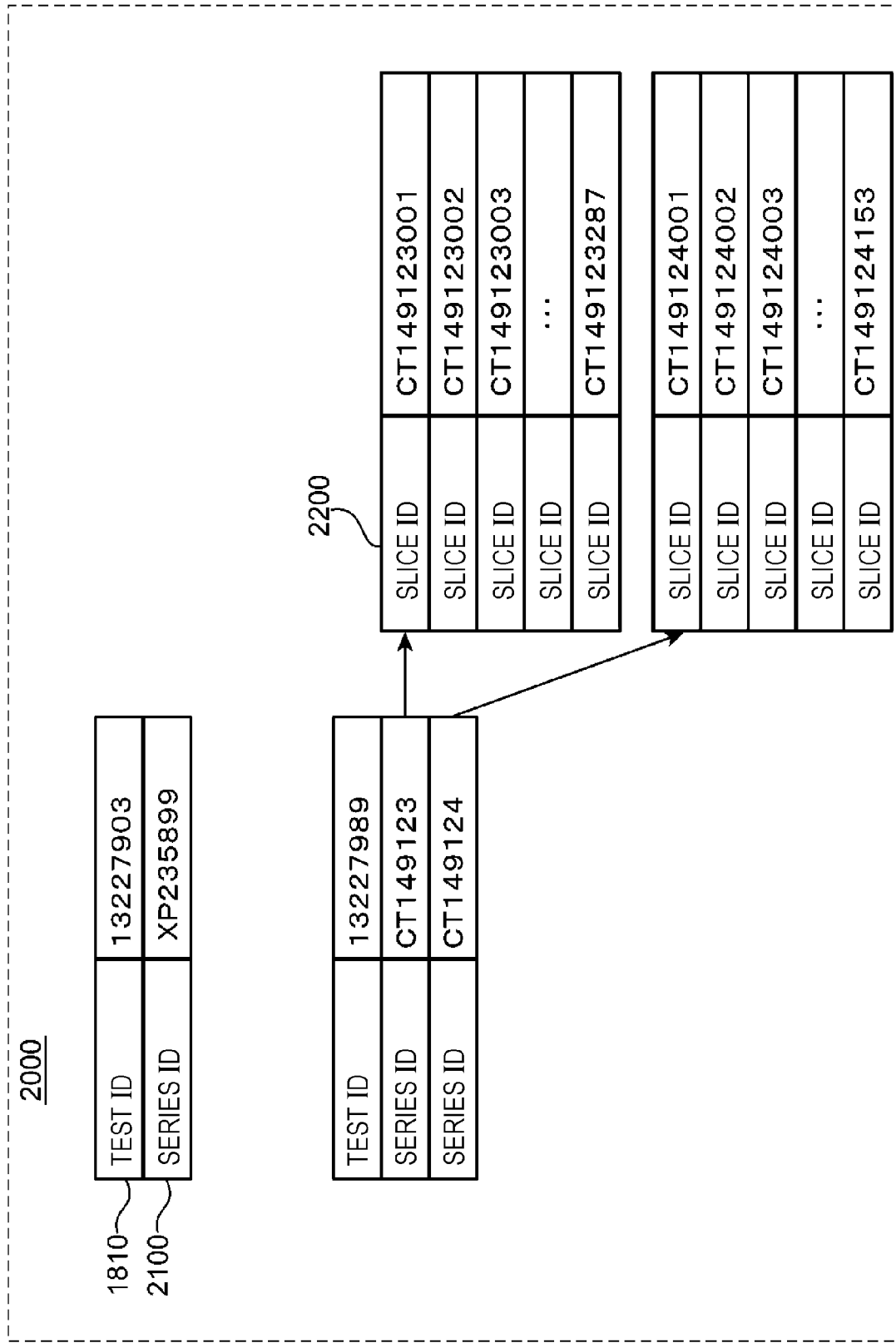
FIG. 13 illustrates the data structure of a medical image database.

FIG. 13 illustrates the data structure of the medical image database 2000. The medical image database 2000 includes a test ID 1810 and a series ID 2100. A plurality of types of imaging (e.g., plain CT and contrast enhanced CT) may be conducted in one test. Accordingly, a plurality of series IDs 2100 may be associated with the test ID 1810. That is, the series equal in number to the types of imaging can be obtained.

In addition to each of the types of imaging, the series can be obtained for each of the conditions of reconfiguration of the captured image. For example, if the captured image is reconfigured using the lung window settings and the mediastinal window settings, a series can be obtained for each of the window settings. Note that in the image reconfigured using the lung window settings, the blood vessels, the bronchus, and the alveolus in the lung image are displayed with contrast enhancement. In addition, in the image reconfigured using the mediastinal window settings, the mediastinum, such as the blood vessels and lymph nodes, is displayed with contrast enhancement. The lung window and the mediastinal window can be obtained by reconfiguring an image captured once. Thus, when two image capturing operations are performed, that is, one for plain CT and the other for contrast enhanced CT and if the two images are reconfigured using the lung window settings and the mediastinal window settings, two series of the lung window settings can be obtained, and two series of the mediastinal window settings are obtained.

In the case of a CT or MRI imaging test, a plurality of slice images are acquired in one image capturing operation. Accordingly, a plurality of slice IDs 2200 are associated with one series ID 2100. In FIG. 13, two series IDs ("CT149123" and "CT149124") are associated with the test ID "13227989". Thus, it can be seen that two series of CT images are acquired from the test. In addition, it can be seen that a plurality of slice IDs 2200 are associated with each of the series IDs "CT149123" and "CT149124".

If the test type 1830 indicates one of a plain CT imaging test, an MRI imaging test, and a PET imaging test, the diagnosis report 3000 illustrated in FIG. 14 is accumulated in the diagnosis report management unit 205 of the medical information management system 200. The diagnosis report 3000 includes the diagnosis made by a physician who conducted each of the tests. FIG. 14 illustrates the data structure of the diagnosis report 3000.

The diagnosis report 3000 includes the test ID 1810, findings 3100, and a diagnosis 3200. The test ID 1810 is the same as the test ID 1810 illustrated in FIG. 12. In this manner, the diagnosis report 3000 is associated with the test information 1800. The findings 3100 include a comment of the physician representing the findings in test results. The diagnosis 3200 includes a comment of the physician representing the diagnosis made by the physician via the test.

FIG. 15 illustrates the data structure of the similar case data 4000. The similar case data 4000 is referenced to search for similar cases each similar to the case to be diagnosed. The similar case data 4000 is generated for each of the similar cases. Note that the similar case data 4000 is an example of additive information to a similar medical image. In the similar case data accumulation unit 301 of the case search system 300, the similar case data 4000 is accumulated for each of the similar cases. As illustrated in FIG. 15, the similar case data 4000 includes a similar case ID 4100, a region-of-interest count 4200, thumbnail image data 4300, a definitive diagnosis count 4400, and disease IDs 4500 equal in number to the count indicated by the definitive diagnosis count 4400. The additive information corresponds to information indicating at least one disease name. That is, the additive information is information used to identify the name of a disease.

The similar case ID 4100 is an identifier of the similar case data 4000. In the example illustrated in FIG. 15, the similar case ID 4100 is formed from a symbol string that starts with "SIM" followed by a number.

Figure 16:
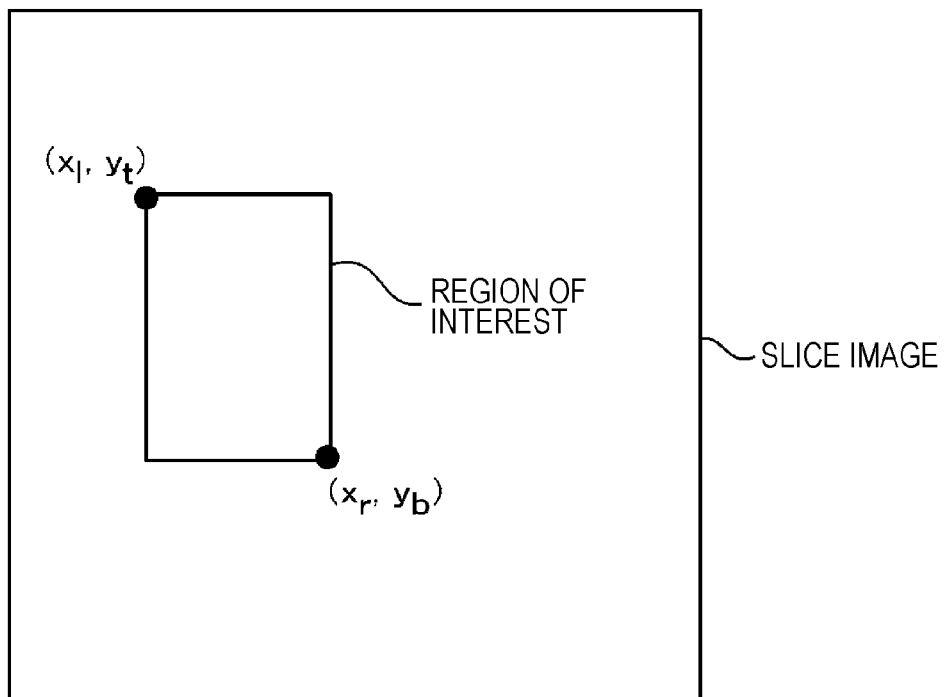
FIG. 16 is a schematic illustration of a region of interest set in a slice image.

The region-of-interest count 4200 represents the number of regions of interest preset for the case indicated by the similar case ID. Note that the similar case data 4000 has region-of-interest IDs 4600, the slice IDs 4700, region-of-interest coordinates 4800, and image feature data 4900 each equal in number to the count indicated by the region-of-interest count 4200. The region-of-interest ID 4600 represents the ID of a region of interest given to the similar case indicated by the similar case ID 4100. Accordingly, the region-of-interest ID 4600 has a format formed from the symbol string indicated by the similar case ID 4100 followed by a sequential number. The slice ID 4700 represents an identifier of a slice image having a region of interest set therein. The slice ID 4700 is the same as the slice ID 2200 illustrated in FIG. 13. The region-of-interest coordinates 4800 is information indicating the position of the region of interest set in the slice image. FIG. 16 is a schematic illustration of a region of interest set in a slice image. In the example illustrated in FIG. 16, the region of interest is rectangular in shape. Accordingly, the region-of-interest coordinates 4800 includes four values, that is, the coordinates (xl, yt) of the upper left vertex and the coordinates (xr, yb) of the lower right vertex of the region of interest. Note that the region of interest may have any shape in addition to a rectangle. In such a case, parameters that can uniquely define the region are employed as the region-of-interest coordinates 4800. For example, if the region of interest is circular in shape, the coordinates of the center and the radius of the circle are employed as the region-of-interest coordinates 4800. The image feature data 4900 represents the feature value of any order (N-order in the present exemplary embodiment) extracted from the region of interest defined by the region-of-interest coordinates 4800.

The thumbnail image data 4300 represents the image data of a thumbnail image that is generated on the basis of the DICOM-format slice image identified by the slice ID so as to be displayed in the case display area 710. According to the present disclosure, a plurality of regions of interest can be set across different slice images. Thus, a plurality of candidates of a thumbnail images are present for the similar case ID 4100. However, according to the present exemplary embodiment, one of the slice images that describes the feature of the similar case indicated by the similar case ID 4100 best is selected as the thumbnail image data 4300 in advance. Note that a thumbnail image may be generated and stored for each of the slice images having a region of interest set therein.

In this example, the thumbnail image data 4300 has the pixel values of a thumbnail image arranged, for example, in the raster scanning sequence starting from the upper left vertex to the lower right vertex of the thumbnail image. As mentioned above, a DICOM image acquired in a CT test is a 11-bit image of 512×512 pixels (pixel value: −1000 to +1000). Thus, according to the present exemplary embodiment, to increase the speed of displaying the thumbnail images, a low resolution process and a grayscale conversion process are performed on a DICOM image that is a source of the thumbnail image to generate the thumbnail image having 8-bit pixel values, and the thumbnail image is stored in the similar case data 4000 in advance. Note that at that time, for example, the medical information management system 200 may generate the thumbnail image and send the thumbnail image to the case search system 300. Alternatively, the case search system 300 may acquire the DICOM image from the medical information management system 200 and generate the thumbnail image.

The definitive diagnosis count 4400 represents the number of disease names given as definitive diagnosis. In this example, since two disease names are given to the case indicated by the similar case ID 4100, "2" is registered in the definitive diagnosis count 4400.

The disease ID 4500 stores disease IDs, which are defined by the disease classification system 5000 (refer to FIG. 36) and are equal in number to the count in the definitive diagnosis count 4400. In this example, since the disease name indicated by the disease ID "DIS012_007" and the disease name indicated by the disease ID "DIS015_019" are given to the case indicated by the similar case ID, "DIS012_007" and "DIS015_019" are registered in the disease ID 4500. The stored one or more disease IDs (e.g., DIS012_007 and DIS015_019) may have one-to-one correspondence with the regions-of-interest IDs (SIM5232_0 and SIM5232_1). That is, SIM5232_0 may correspond to DIS012_007, and SIM5232_1 may correspond to DIS015_019.

The flow of the processes performed by 100 in cooperation with the medical information management system 200 and the case search system 300 from start of interpretation until start of the similar case search is described below.

Figure 17:
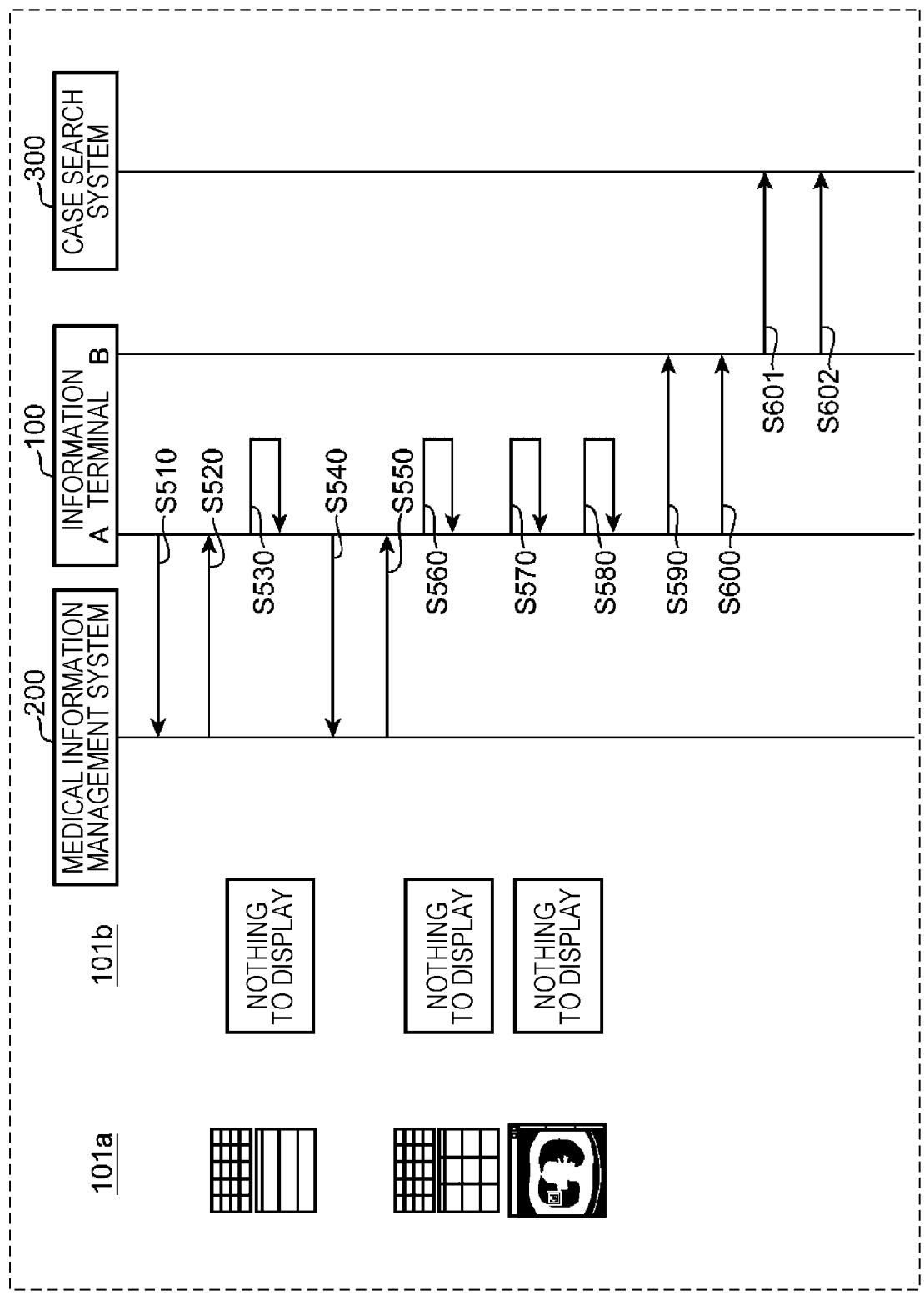
FIG. 17 is a sequence diagram illustrating the processes performed after the information terminal acquires, from the medical information management system, a case to be diagnosed and sends, to the case search system, a request for a similar case search until the case search system receives the request for a similar case search.

FIG. 17 is a sequence diagram illustrating the processes performed after the information terminal 100 acquires, from the medical information management system 200, a case to be diagnosed and sends, to the case search system 300, a request for the similar case search until the case search system 300 receives the request for the similar case search. Note that in FIG. 17, the boxes located to the left of the sequence diagram and arranged in two columns represent the screens displayed on the displays 101*a* and 101*b*. In addition, in FIG. 17, "A" in the information terminal represents the medical information management application, and "B" represents the similar case search application. Before the sequence starts, the medical information management application is started in advance.

The information terminal 100 receives, via the operation unit 102, a display request for displaying a test list to be interpreted by a user (a physician who interprets a medical image). Thereafter, the information terminal 100 sends a display request for displaying the test list to the communication control unit 206 of the medical information management system 200 via the input control unit 103 and the communication control unit 107 first (S510).

Subsequently, the patient information management unit 202 of the medical information management system 200 makes a list of the tests for which interpretation has not been completed after the imaging test has been conducted. Thereafter, the patient information management unit 202 sends the generated test list to the communication control unit 107 of the information terminal 100 via the communication control unit 206 (S520). Note that the test list includes the patient information 1000 and the test information 1800 regarding the target patient.

The display control unit 104 of the information terminal 100 displays, on the display 101, the test list received by the communication control unit 107 (S530).

In this case, the test list is displayed on the display 101*a*, and nothing is displayed on the display 101*b*.

FIG. 18 illustrates the screen of the test list. The test list includes an area 800 that displays the tests for which interpretation has not been completed and an area 810 that displays the information regarding the series contained in the test. The area 800 includes the following fields: "patient ID", "patient name", "test date and time", "test ID", and "test type". The patient ID 1100 and the name 1200 registered in the patient information 1000 are displayed in the patient ID field and the patient name field, respectively. The test date and time 1820, the test ID 1810, and the test type 1830 registered in the test information 1800 are displayed in the test date and time field, the test ID field, and the test type field, respectively. The area 810 is used to display the details of the test selected by the user in the area 800. The area 810 includes the following fields: "series ID", "definition", and "image". In this example, since any test (corresponding to one of rows) is not selected by the user in the area 800, nothing is displayed in the area 810.

The user selects one of the tests to be interpreted from among the tests displayed in the area 800. Upon detecting selection of a test by the input control unit 103, the communication control unit 107 sends, to the medical information management system 200, a request for displaying all the series included in the selected test ID, as illustrated in FIG. 17 (S540).

When the communication control unit 206 of the medical information management system 200 receives the display request, the patient information management unit 202 refers to the medical image database 2000 illustrated in FIG. 13 and acquires all the slice images for all the series included in the test ID specified by the display request. Thereafter, the patient information management unit 202 sends the slice images to the information terminal 100 via the communication control unit 206 (S550). For example, in the example illustrated in FIG. 13, if the test having a test ID of "13227989" is selected by the user, all the slice images contained in the series having series IDs "CT149123" and "CT149124" are sent in step S550.

After the communication control unit 107 of the information terminal 100 acquires the images of all the series, the display control unit 104 displays, in the area 810, a series list that includes information regarding all the series contained in the specified test ID in the form of a list (S560).

In such a case, the series list of the series corresponding to the test selected in the area 800 is displayed in the area 810 of the test list displayed on the display 101*a*, and nothing is displayed on the display 101*b*.

FIG. 19 illustrates the screen of the test list after the test is selected. In the area 800 illustrated in FIG. 19, the background of the selected row is highlighted. In the example illustrated in FIG. 19, the test for "Taro Pana" in the second row is selected in the area 800. Accordingly, in the area 810, "series ID", "definition", and "image" for the selected test are displayed. Note that the series ID associated with the selected test ID in the medical image database 2000 is displayed in the series ID field, and the thumbnail image of a slice image that represents the displayed series ID is displayed in the image field. At that time, an image located at a predetermined slice position is selected as the slice image that represents the series ID. The predetermined slice position may be a slice position at the top position or at the middle position. The "Definition" field indicates the image capturing condition and the reconfiguration condition for the corresponding series. Although not illustrated, the definition is registered in the medical image database 2000 illustrated in FIG. 13 in association with, for example, the series ID.

Figure 20:
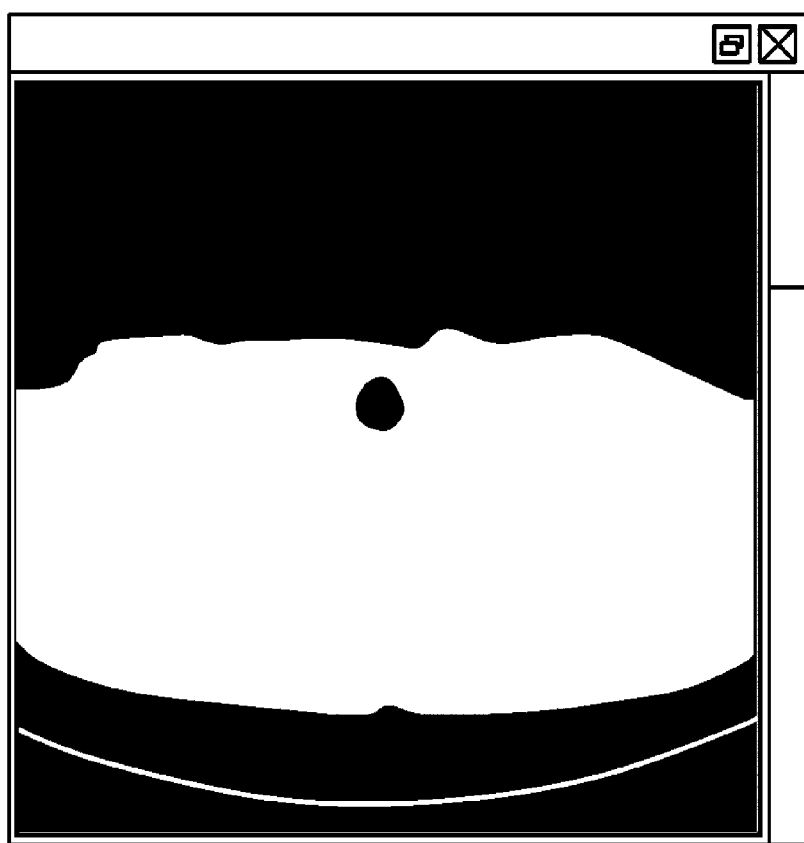
FIG. 20 illustrates a slice image displayed in a medical image viewer when a user selects a series.

After the series to be interpreted is selected by the user in the area 810 and the input control unit 103 detects the selection, the display control unit 104 displays, on the display 101, the slice image at the top of the selected series, as illustrated in FIG. 20 (S570). FIG. 20 illustrates a slice image displayed on the display 101*a* when the user selects the series. The slice image illustrated in FIG. 20 is a first slice image obtained in chest CT imaging. In the example illustrated in FIG. 20, the slice image at the shoulder position slightly closer to the head from the apex area of the lung is displayed.

Note that the slice image representing the series is selected by a physician who interprets the medical images. Accordingly, if the physician has not interpreted the medical images, the first slice image, for example, is displayed on the display 101*a* as a default slice image. In addition, since the physician has not yet set up a region of interest in the slice image illustrated in FIG. 20, a region of interest is not displayed.

In addition, the display control unit 104 displays all the slice images of the selected series on the display 101*a* so that the previous series or the next series can be loaded. Note that nothing is displayed on the display 101*b*. For example, the input control unit 103 detects a slice feed operation performed by the user in which the user places the mouse pointer on the display 101*a* at a desired position and moves a mouse wheel. Then, the display control unit 104 changes the slice image displayed on the display 101*a* to a slice image located at another slice position in accordance with the amount of mouse wheel scrolling. The user performs a slice feed operation and makes a diagnosis via the medical image. At that time, if it is difficult for the user to makes a diagnosis via the medical image, the user starts the similar case search application.

At that time, the user may start the similar case search application by inputting a predetermined short-cut key into the keyboard of the operation unit 102 or displaying the menu of the medical image viewer using a right click of the mouse and selecting "similar case search". Upon detecting the instruction to start the similar case search application, the control of the information terminal 100 is transferred to the ROI management unit 105 and, thus, the information terminal 100 enters a ready mode for receiving an input of a region of interest (ROI).

The user sets a region of interest (ROI) over the lesion in the slice image displayed on the display 101*a* (S580) using the operation unit 102. At that time, as illustrated in FIG. 16, the user left click the mouse and inputs the coordinates of the upper left vertex of the region of interest, for example. Subsequently, the user drags the mouse diagonally toward the lower right corner while holding the left click button. Thereafter, the user releases the mouse button. In this manner, the user can input the coordinates of the lower right vertex of the region of interest.

FIG. 5 illustrates an example of the slice image screen after the region of interest is set over the lesion. One or more regions of interest can be set. In the series to be interpreted, if the number of lesion areas which the user is interested in is one, one region of interest can be set. In contrast, if the number of lesion areas which the user is interested in is two, two regions of interest can be set.

As an example in which the user wants to set two regions of interest, there may be two different lesions, as illustrated in FIG. 5. For example, the user sets ROI_A for a cavitary disease and sets ROI_B for a granular shadow. In this manner, a past similar case that has two types of lesion similar to the lesions can be searched for. Note that to set a plurality of ROIs, the slice image for which the ROIs are to be set is not necessarily the same slice image. For example, ROIs may be set in a plurality of slice images of the same series.

When the input control unit 103 detects the operation to set a region of interest, the ROI management unit 105 receives the coordinate data of the upper left vertex and the lower right vertex of the region of interest from the input control unit 103 and generates the region-of-interest information including the received coordinate data. Thereafter, the ROI management unit 105 sends the region-of-interest information to the communication control unit 107 (S590).

At the same time, the ROI management unit 105 sends the slice image of the case to be diagnosed to the communication control unit 107 (S600). In such a case, among the slice images of all the series received by the information terminal 100 from the medical information management system 200, the slice image for which the user sets a region of interest in the series selected by the user is sent in step S550. If the user sets regions of interest in a plurality of the slice images, the plurality of slice images are sent.

Subsequently, the communication control unit 107 receives the region-of-interest information sent from the ROI management unit 105 and sends the region-of-interest information to the communication control unit 305 of the case search system 300 (S601).

At the same time, the communication control unit 107 receives the slice image sent from the ROI management unit 105 and sends the slice image to the communication control unit 305 of the case search system 300 (S602).

Note that in steps S600 and S601, the slice image is sent. However, only the slice ID of the slice image may be sent. In such a case, upon receiving the slice ID, the case search system 300 can acquire the slice image from the medical information management system 200 by using the slice ID.

The process performed after the case search system 300 performs a similar case search until the information terminal 100 display the result of the similar case search as an initial screen is described below.

Figure 21:
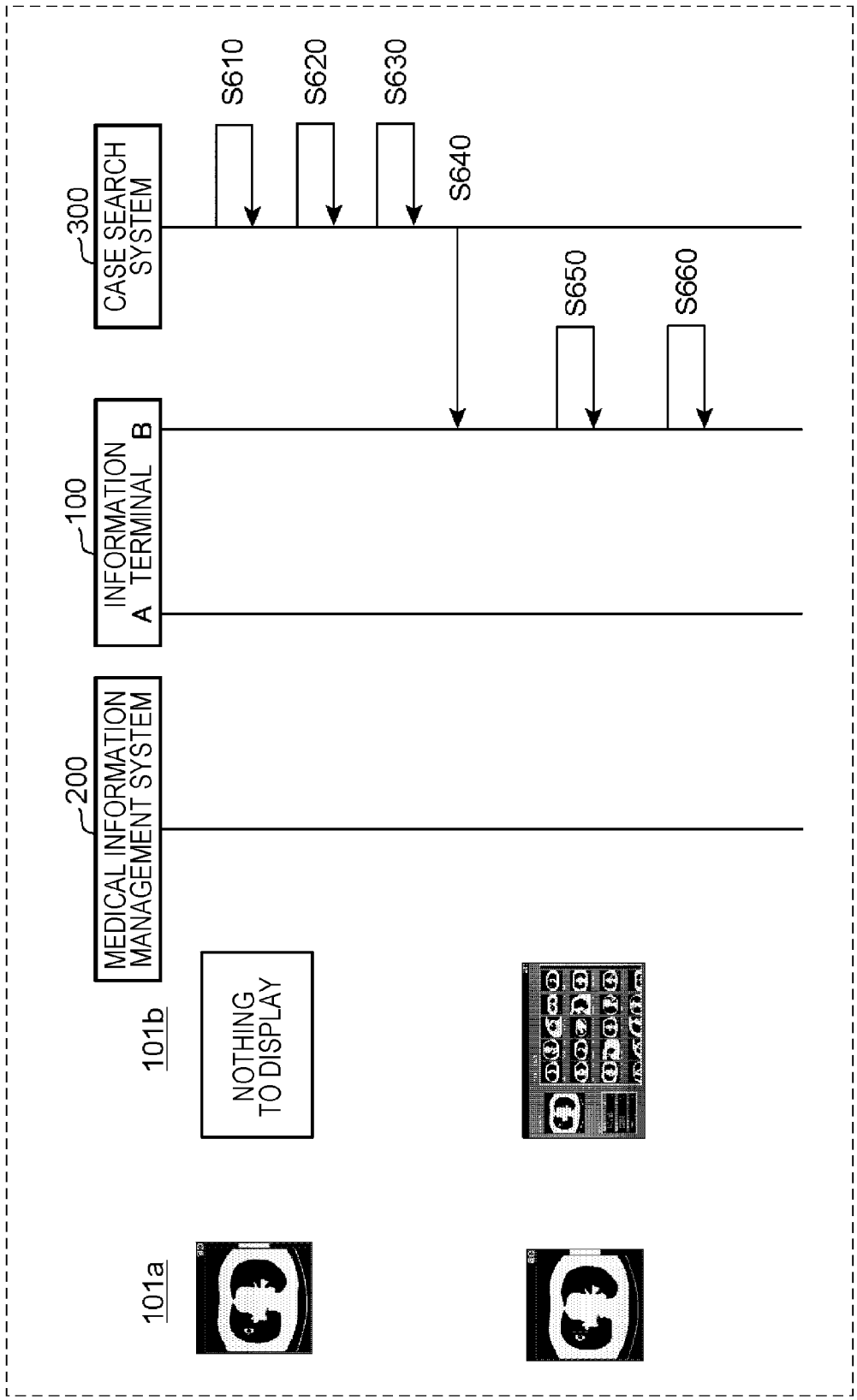
FIG. 21 is a sequence diagram illustrating the processes performed after the case search system receives a similar case search request until the case search system returns the result of the similar case search to the information terminal.

FIG. 21 is a sequence diagram illustrating the processes performed after the case search system 300 receives a similar case search request until the case search system 300 returns the result of the similar case search to the information terminal 100.

The image feature extraction unit 302 of the case search system 300 extracts predetermined multi-order image features for each of the set regions of interest (hereinafter referred to as an "image feature set") (S610).

Examples of the image feature set to be employed include an image feature set regarding the shape of an organ or a lesional tissue in the medical image and an image feature set regarding the luminance distribution. For example, a 490-order dimensional image feature set can be employed as described in the following non-patent literature: NEMOTO, SHIMIZU, HAGIHARA, KOBATAKE, and NAWANO, "Improvement of Tumor Detection Performance in Mammograms by Feature Selection from a Large Number of Features and Proposal of Fast Feature Selection Method", The Institute of Electronics, Information and Communication Engineers Journal Vol. J88-D-II, No. 2, pp. 416-426, February 2005. According to the present exemplary embodiment, for example, the image feature set described in the non-patent literature is employed. However, this image feature set is only illustrative. Another image feature set may be employed. According to the present exemplary embodiment, if two regions of interest are set, the image feature set is extracted from each of the regions of interest.

The similar case search unit 303 compares the image feature set extracted by the image feature extraction unit 302 with the image feature set of each of the similar cases accumulated in the similar case data accumulation unit 301 (S620). At that time, the similar case search unit 303 compares the two image feature sets with each other by calculating the distance between the image feature set extracted from the search query image and the image feature data 4900 (the image feature set) registered in the similar case data 4000 (refer to FIG. 15) accumulated in the similar case data accumulation unit 301 for each of the similar cases.

A search method employed when the number of regions of interest, that is, the number of image feature sets in the search query image differs from that in a similar case is described below.

Figure 22:
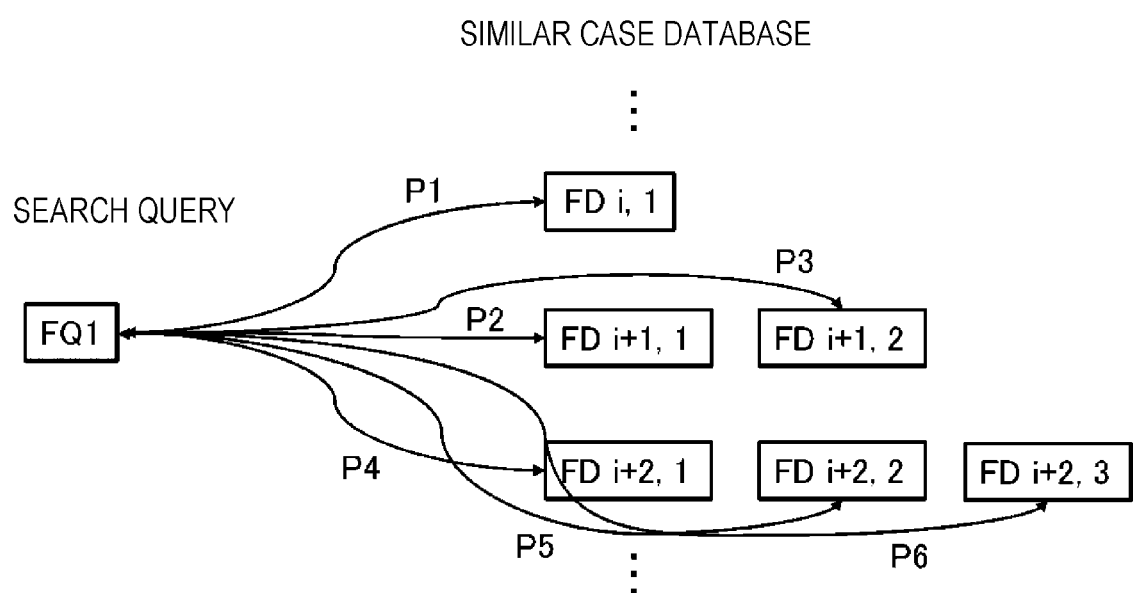
FIG. 22 illustrates a method for comparing image feature sets with each other employed when the number of regions of interest (the number of image feature sets) in the search query image is equal to 1.

FIG. 22 illustrates a method for comparing the image feature sets with each other employed when the number of regions of interest (the number of image feature sets) of the search query image is equal to 1. In the example illustrated in FIG. 22, a method for comparing one image feature set (FQ1) of the search query image with the image feature sets of three similar cases having similar case IDs of i+1, and i+2 is illustrated. In the example illustrated in FIG. 22, the similar case having a similar case ID of i has one image feature set. The similar case having a similar case ID of i+1 has two image feature sets. The similar case having a similar case ID of i+2 has three image feature sets.

To compare the search query image with the similar case having a similar case ID of i, the similar case search unit 303 calculates Euclidean distance, that is, calculates the distance once (P1), since each of the two images has one image feature set. To compare the search query image with the similar case having a similar case ID of i+1, the similar case search unit 303 calculates the distance twice (P2, P3), since the number of image feature sets of the similar case having a similar case ID of i+1 is 2. That is, the similar case search unit 303 calculates the distance between the image feature set of the search query image and each of the two image feature sets of the similar case having a similar case ID of i+1. Thereafter, the similar case search unit 303 selects a smaller one of the two calculated distances as the distance between the search query image and the similar case having a similar case ID of i+1.

Similarly, to compare the search query image with the similar case having a similar case ID of i+2, the similar case search unit 303 calculates the distance three time (P4, P5, P6), since the number of image feature sets of the similar case having a similar case ID of i +2 is 3. That is, the similar case search unit 303 calculates the distance between the image feature set of the search query image and each of the three image feature sets of the similar case having a similar case ID of i+2.

Thereafter, the similar case search unit 303 selects the smallest one of the three calculated distances as the distance between the search query image and the similar case having a similar case ID of i+2.

A search method for comparing a search query image having two image feature sets with each of the similar cases having similar case IDs of i, i+1, and i+2 is described below. Note that as illustrated in FIG. 22, the similar cases having similar case IDs of i, i+1, and i+2 have one image feature set, two image feature sets, and three image feature sets, respectively.

If the search query image has two image feature sets, the similar case to be searched for is limited to the similar cases each having two or more image feature sets. Accordingly, the similar case having a similar case ID of i is excluded from the search, and the similar cases having similar case IDs of i+1 and i+2 are targets of the search.

FIG. 23 illustrates a method for comparing the image feature sets when each of the number of regions of interest (the number of image feature sets) of the search query image and the number of regions of interest (the number of image feature sets) in the similar case to be compared is equal to 2.

Note that in FIG. 23, FQ1 and FQ2 represent the two image feature sets of the search query image.

In addition, in FIG. 23, let P1 be the distance between the image feature set FQ1 and a first image feature set (FDi+1, 1) of the similar case having a similar case ID of i+1. Let P3 be the distance between the image feature set FQ1 and a second image feature set (FDi+1, 2) of the similar case having a similar case ID of i+1. Let P4 be the distance between an image feature set FQ2 and the first image feature set (FDi+1, 1) of the similar case having a similar case ID of i+1. Let P2 be the distance between the image feature set FQ2 and the second image feature set (FDi+1, 2) of the similar case having a similar case ID of i+1.

Then, since each of the number of image feature sets of the search query image and the number of image feature sets of the similar case to be compared is equal to 2, the similar case search unit 303 calculates the distance 4 (=2×2) times (P1 to P4). At that time, the combinations of comparison of two image feature sets are the following two combinations: "P1 and P2" and "P3 and P4". Accordingly, the similar case search unit 303 selects a smaller one of the average of the distances "P1 and P2" and the average of the distances "P3 and P4" as the distance between the search query image and the case having a similar case ID of i+1.

FIG. 24 illustrates a method for comparing the image feature sets when the number of regions of interest (the number of image feature sets) of the search query image is equal to 2 and the number of regions of interest (the number of image feature sets) in the similar case to be compared is equal to 3. In the example illustrated in FIG. 24, since the number of regions of interest of the search query image is equal to 2 and the number of regions of interest of the similar case to be compared is equal to 3, the similar case search unit 303 calculates the distance 6 (=2×3) times (P1 to P6).

Note that in FIG. 24, FQ1 and FQ2 represent the two image feature sets of the search query image.

In addition, in FIG. 24, let P1 be the distance between the image feature set FQ1 and a first image feature set (FDi+2, 1) of the similar case having a similar case ID of i+2. Let P2 be the distance between the image feature set FQ1 and a second image feature set (FDi+2, 2) of the similar case having a similar case ID of i+2. Let P3 be the distance between the image feature set FQ1 and a third image feature set (FDi+2, 3) of the similar case having a similar case ID of i+2. In addition, let P4 be the distance between the image feature set FQ2 and a first image feature set (FDi+2, 1) of the similar case having a similar case ID of i+2. Let P5 be the distance between the image feature set FQ2 and the second image feature set (FDi+2, 2) of the similar case having a similar case ID of i+2. Let P6 be the distance between the image feature set FQ2 and a third image feature set (FDi+2, 3) of the similar case having a similar case ID of i+2.

At that time, the combinations of comparison of the two image feature sets are the following six combinations: "P1 and P5", "P1 and P6", "P2 and P4", "P2 and P6", "P3 and P4", and "P3 and P5". Accordingly, the similar case search unit 303 selects the smallest one of the averages of the distances of the six combinations as the distance between the search query image and the case having a similar case ID of i+2.

In this manner, the distance between the search query image and the similar case having different numbers of image feature sets (i.e., different numbers of regions of interest) can be calculated.

Referring back to FIG. 21, the similar case search unit 303 sorts the similar cases having distances that are less than or equal to a predetermined threshold value in order of ascending distance and selects the similar cases as the similar cases to be sent (S630). Subsequently, the communication control unit 305 sends, to the information terminal 100, the similar case ID 4100, the thumbnail image data 4300, the definitive diagnosis count 4400, the disease ID 4500, and the distance calculated by the similar case search unit 303 of each of the similar cases selected to be sent among the similar case data 4000 accumulated in the similar case data accumulation unit 301 (S640).

Subsequently, a process to generate the initial basic screen K2 that displays the similar case search result (refer to FIG. 6) is performed (S650).

Figure 25:
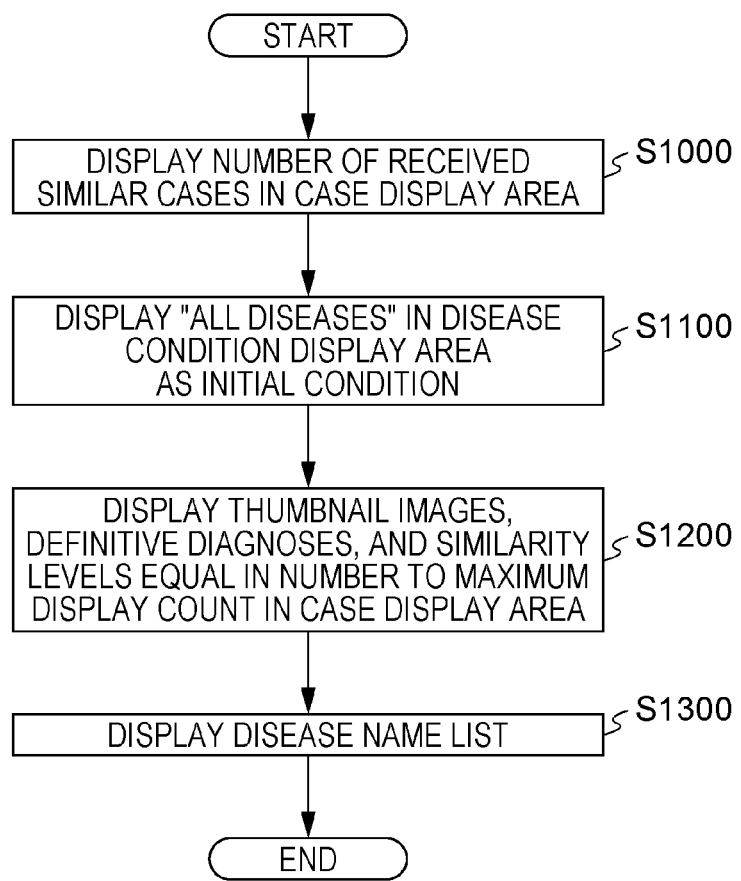
FIG. 25 is a flowchart illustrating a detailed process performed to generate an initial basic screen in step S650 of FIG. 21.

FIG. 25 is a flowchart illustrating a detailed process performed to generate the initial basic screen K2 in step S650 of FIG. 21.

In step S1000, the display control unit 104 counts the number of the similar cases received in step S640 of FIG. 21 and displays the count value in the case count display area 714 first.

Subsequently, in step S1100, the display control unit 104 displays "All Diseases" in the disease condition display area 715. This is because a narrowed search using a disease name has not been conducted by the user in the initial basic screen K2.

Subsequently, in step S1200, the display control unit 104 displays, in the case display area 710, the thumbnail images of the similar cases equal in number to the number of the similar cases each having a displayable thumbnail image among the similar cases received in step S640 illustrated in FIG. 21. In addition, the display control unit 104 displays the definitive diagnosis and the similarity in association with each of the thumbnail images.

In the example illustrated in FIG. 6, the highest number of the similar cases that can be displayed in the case display area 710 is 15 (20 if the similar cases that allow the upper half of the image to be displayed are included). The highest number is predetermined. In addition, a configuration in which the user can change the highest number may employed. If the number of the similar cases received in step S640 illustrated in FIG. 21 is greater than the highest value, the display control unit 104 displays the scroll bar 713 that extends vertically at the right end of the case display area 710. In this manner, the user can move the scroll bar 713 and view the thumbnail images of the similar cases that are hidden in the initial basic screen K2.

Subsequently, in step S1300, the display control unit 104 generates the disease name list information 6000 (refer to FIGS. 27, 28, and 29) and displays the disease name list display area 730. The disease name list information 6000 is in the form of a table containing the number of cases and at least one similar case ID for each of the disease IDs for all the similar cases received in step S640 illustrated in FIG. 21. The disease name list display area 730 allows the user to view the definitively diagnosed disease name and the number of cases on the basis of the disease name list information 6000.

Figure 26:
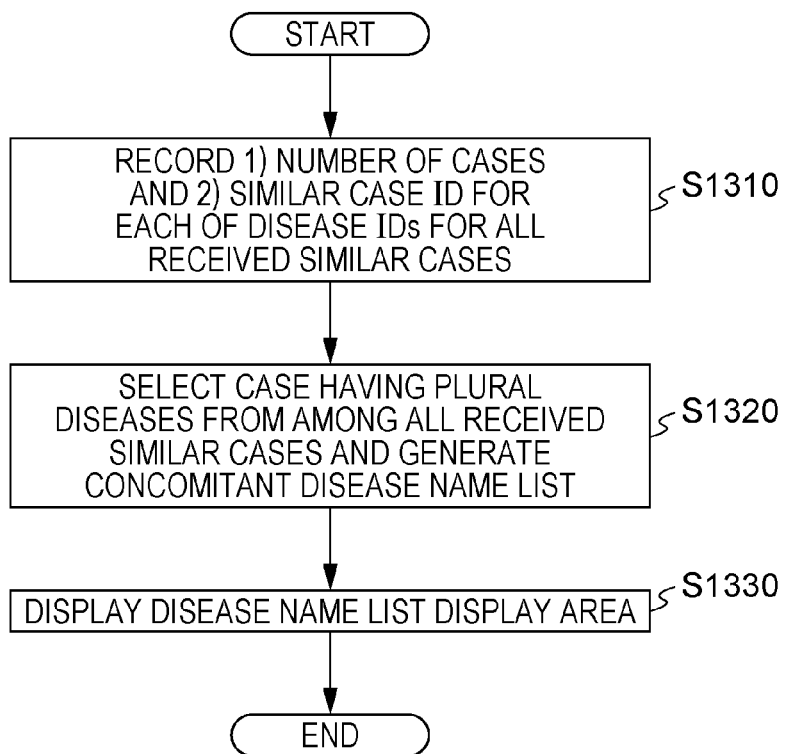
FIG. 26 is a flowchart of a detailed process performed in step S1300 illustrated in FIG. 25.

The process performed in step S1300 is described in detail below with reference to a flowchart illustrated in FIG. 26.

In step S1310, the display control unit 104 records, in the disease name list information 6000, the number of cases and the similar case ID for each of the disease IDs 4500 for all the similar cases received in step S640 illustrated in FIG. 21.

Let NC be the number of the similar cases received in step S640. Then, some similar case data 4000 may include a plurality of definitive diagnoses (a plurality of disease IDs). In this example, the display control unit 104 simply counts the frequency of appearance of the disease ID instead of counting the number of the similar cases. Accordingly, the total number of cases in the disease name list information 6000 may exceed NC.

FIGS. 27, 28, and 29 illustrate examples of the disease name list information 6000. As illustrated in FIGS. 27, 28, and 29, the disease name list information 6000 has three patterns. First disease name list information 6000 illustrated in FIG. 27 includes small classification disease names sorted in the order of descending case numbers. Accordingly, in the disease name list information 6000 illustrated in FIG. 27, the number of cases counted for each of the small category disease names is registered in the "Number of cases" column.

More specifically, the disease name list information 6000 illustrated in FIG. 27 includes "disease ID", " large category disease name", "small category disease name", "number of cases", and "similar case ID" fields. The "disease ID" is the same as the disease ID 4500 illustrated in FIG. 15. The "large category disease name" field has a large category disease name corresponding to the disease ID registered therein. The "small category disease name" field has the small category disease name corresponding to the disease ID registered therein. The "similar case" field has the similar case ID of at least one similar case having a corresponding disease ID registered therein. The similar case ID is the same as the similar case ID 4100 illustrated in FIG. 15.

For example, the disease ID "DIS002_001" has a large category disease name of neoplastic "002" and a small category disease name of lung cancer "001". Accordingly, the " large category disease name" field has " neoplastic" registered therein, and the "small category disease name" field has "lung cancer" registered therein. In addition, since the number of cases of lung cancer, which is the small category disease name for the disease ID "DIS002_001", is equal to 10, the "number of cases" field has "10" registered therein. Furthermore, the similar case IDs of ten similar cases each having the disease ID "DIS002_001" (SIM1592, SIM2205, SIM8137, . . . ) are registered in the "similar case ID" field.

The second disease name list information 6000 illustrated in FIG. 28 is obtained by sorting the large category disease names in the order of descending number of cases.

Accordingly, the "number of cases" field of the disease name list information 6000 illustrated in FIG. 28 has the number of cases counted for the large category disease registered therein. More specifically, the disease name list information 6000 illustrated in FIG. 28 includes "disease ID", "large category disease name", "number of cases", and "similar case ID" fields. Unlike the disease name list information 6000 illustrated in FIG. 27, the "small category disease name" field is removed, since the number of cases in the disease name list information 6000 illustrated in FIG. 28 is counted for a large category disease name.

For example, the disease ID "DIS011" has a large category disease name of mycosis "011". Accordingly, "mycosis" is registered in the "large category disease name" field. In addition, since the number of cases for mycosis, which is the large category disease name of "DIS011", is equal to 14, "14" is registered in the "number of cases" field. Furthermore, the similar case IDs of 14 similar cases (SIM2205, SIM4172, SIM6089, . . . ) each having a disease ID of "DIS011" are registered in the "similar case ID" field.

The third disease name list information 6000 illustrated in FIG. 29 is obtained by sorting the large category names received in step S640 in the order of descending number of cases and further sorting the small category disease names in the order of descending number of cases. More specifically, the disease name list information 6000 illustrated in FIG. 29 includes "disease ID", "large category disease name", "small category disease name", "number of cases" and similar case ID fields. In the example in FIG. 29, the number of cases of mycosis "011" is equal to 14, which includes 8 "aspergillosis" cases and 6 "cryptococcosis" cases. Accordingly, the disease name list information 6000 illustrated in FIG. 29 has a row of a disease ID of "DIS011" indicating a large category disease name and a row of a disease ID of "DIS011_002" and a row of a disease ID of "DIS011_003" each indicating a small category disease name.

In addition, in the row of a disease ID of "DIS011", "mycosis" is registered in the "large category disease name" field. In addition, "-" indicating a blank is registered in the "small category disease name", and "14" is registered in the "number of cases" field. Furthermore, in the row of a disease ID of "DIS011_002", "mycosis" is registered in the "large category disease name" field, "aspergillosis" is registered in the "small category disease name" field, and "8" is registered in the "number of cases" field. Still furthermore, in the row of a disease ID of "DIS011_003", "mycosis" is registered in the "large category disease name" field, "cryptococcosis" is registered in the "small category disease name" field, and "6" is registered in the "number of cases" field.

Each disease name list information 6000 illustrated in FIGS. 27, 28, and 29 has the "disease ID", "number of cases", and "similar case ID" fields. Note that in FIGS. 27, 28, and 29, the "large category disease name" and "small category disease name" fields are provided for convenience of description and, thus, may be removed. This is because if the disease classification system 5000 (refer to FIG. 36) stored in the disease classification system definition unit 304 is used, the display control unit 104 can uniquely identify the large category disease name and the small category disease name by using the disease ID.

Referring back to FIG. 26, in step S1320, the display control unit 104 selects the similar cases each having a plurality of disease IDs from among all the similar cases received in step S640 illustrated in FIG. 21. Thereafter, the display control unit 104 generates concomitant disease name list information 6500 that records "disease ID" indicating the name of a concomitant disease, "number of cases", and "similar case ID" (refer to FIG. 30). FIG. 30 illustrates an example of the concomitant disease name list information 6500.

To facilitate search for a concomitant disease ID using the disease ID, the concomitant disease name list information 6500 records the "concomitant disease ID", "number of cases", and "similar case ID" for each of the disease IDs in association with one another. The "disease ID" is the same as the disease ID 4500 illustrated in FIG. 15. The "concomitant disease ID" is the "disease ID" of a disease concomitant with a disease indicated by a corresponding "disease ID". The "number of cases" is the number of the similar cases in which the disease indicated by the "disease ID" and the disease indicated by the "concomitant disease ID" occur concurrently. The "similar case ID" represents the similar case ID of a similar case in which the disease indicated by the "disease ID" and the disease indicated by the "concomitant disease ID" occur concurrently.

In the concomitant disease name list information 6500, the "number of cases" is counted for each of the "disease ID". Accordingly, in the concomitant disease name list information 6500, a disease name A of a disease concomitant with a disease having a disease name B and the disease name B are double counted in the "number of cases". Some of the similar cases have three or more definitive diagnoses and, thus, have three or more disease IDs. However, according to the present exemplary embodiment, only a relationship between two disease names is discussed. For example, suppose that some similar case has definitive diagnoses of three disease names A, B, and C. In such a case, the similar cases are divided into the following six patterns: A-B, A-C, B-A, B-C, C-A, and C-B, and are registered in the concomitant disease name list information 6500. Note that the generated disease name list information 6000 and concomitant disease name list information 6500 are managed by the disease name list management unit 106.

In the example illustrated in FIG. 15, "DIS012_007" and "DIS015_019" are registered as the disease IDs 4500. Accordingly, a row corresponding to "DIS012_007" and a row corresponding to "DIS015_019" are registered in the concomitant disease name list information 6500. Thereafter, "DIS015_019" is registered in the concomitant disease ID field of the row having a disease ID of "DIS012_007" as the concomitant disease ID, and "DIS012_007" is registered in the concomitant disease ID field of the row having a disease ID of "DIS015_019".

Referring back to FIG. 26, in step S1330, the display control unit 104 generates the disease name list display area 730 using the disease name list information 6000 generated in this manner and displays the disease name list display area 730 on the display 101.

FIGS. 31, 32, and 33 illustrate a first display example, a second display example, and a third display example of the disease name list display area 730, respectively. Note that the disease name list display area 730 illustrated in each of FIGS. 31, 32, and 33 is an example of a standalone disease name list.

As illustrated in FIG. 31, in the first display example, as the similar cases obtained as a result of the similar case search, the small category disease names are listed in association with the numbers of cases from the top in the order of descending numbers of cases and are displayed. To display the list, the disease name list information 6000 illustrated in FIG. 27 is used.

More specifically, in the disease name list information 6000 illustrated in FIG. 27, the small category disease names starting from "lung cancer" to "bronchiectasis" are displayed in the order of descending number of cases. Accordingly, in the disease name list display area 730 illustrated in FIG. 31, the small category disease names starting from "lung cancer" to "bronchiectasis" are sequentially displayed in the 1st row to the 10th row in the order of descending number of cases. In this manner, the user can easily recognize the small category disease names each serving as the candidate of a search query image arranged in the order of descending number of cases.

As illustrated in FIG. 32, in the second display example, as the similar cases obtained as a result of the similar case search, the large category disease names are listed in association with the number of the cases from the top in the order of descending number of cases and are displayed. To display the list, the disease name list information 6000 illustrated in FIG. 28 is used.

More specifically, in the disease name list information 6000 illustrated in FIG. 28, the large category disease names starting from "mycosis" to "the others" are sorted and listed in the order of descending number of cases. Accordingly, in the disease name list display area 730 illustrated in FIG. 32, the large category disease names starting from "mycosis" to "the others" are sequentially displayed in the 1st to 5th rows. In this manner, the user can easily recognize the large category disease names each serving as the candidate of a search query image arranged in the order of descending number of cases.

As illustrated in FIG. 33, in the third display example, as the similar cases obtained as a result of the similar case search, the large category disease names are listed in association with the number of the cases from the top in the order of descending number of cases and are displayed. In addition, the small category disease names contained in each of the large category disease names are displayed in association with the number of cases in the order of descending number of cases. In this manner, in the third display example, the definitively diagnosed disease names are displayed in a hierarchical structure of the large category disease names and the small category disease names. To display the list, the disease name list information 6000 illustrated in FIG. 29 is used.

More specifically, in the disease name list information 6000 illustrated in FIG. 29, the large category disease names "mycosis", "neoplastic", "nonneoplastic", and "mycobacteriosis" are sorted and listed in this order. Accordingly, in the disease name list display area 730 illustrated in FIG. 33, the list of large category items 7301 including "mycosis", "neoplastic", "nonneoplastic", and "mycobacteriosis" is displayed in this order. In addition, in the disease name list information 6000 illustrated in FIG. 29, for example, "aspergillosis" and "cryptococcosis", which are the small category disease names of "mycosis", are sorted and listed in this order. Accordingly, in the third display example, the list of small category items 7302 including "aspergillosis" and "cryptococcosis", which are the small category disease names of "mycosis", is displayed in this order. In this manner, the user can easily recognize the large category disease names and the small category disease names each serving as the candidate of a search query image arranged in the order of descending number of cases.

Through the above-described process, the initial basic screen K2 that displays the similar case search result (refer to FIG. 6) is generated. Referring back to FIG. 21, if the input control unit 103 detects a user's operation on the disease name list display area 730 of the basic screen K2, the display control unit 104 performs a process corresponding to the detected operation (S660).

Note that even for the disease name list display area 730 that displays the large category disease names illustrated in FIG. 32, the display control unit 104 may display the small category disease names in accordance with user's operation. In such a case, the display control unit 104 can acquire the disease name list information 6000 illustrated in FIG. 29 and extract only the large category disease names from the disease name list information 6000. Thereafter, the display control unit 104 can display, in the disease name list display area 730 illustrated in FIG. 32, the extracted large category disease names.

Figure 34:
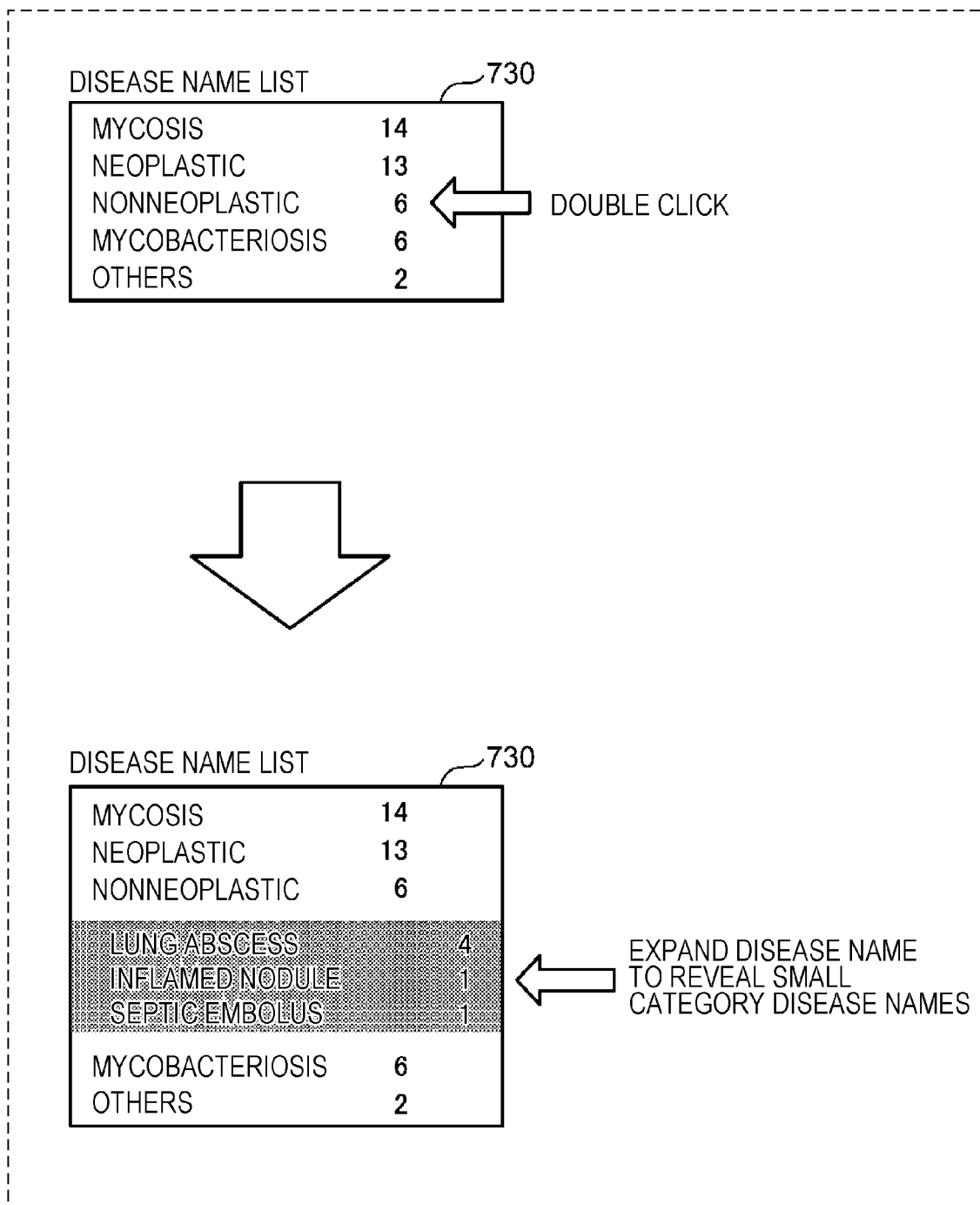
FIG. 34 illustrates transition through screens of the disease name list display area.

FIG. 34 illustrates transition of screens of the disease name list display area 730 illustrated in FIG. 32. As indicated by the upper section of FIG. 34, if the input control unit 103 detects that one of the listed and displayed large category disease names is selected by user's operation, the display control unit 104 displays the small category disease names that belongs to the selected large category disease name in association with the number of cases in the order of descending number of cases, as indicated in the lower section of FIG. 34. At that time, by, for example, clicking or double clicking the desired one of the large category disease names listed and displayed in the disease name list display area 730, the user can select the one of the large category disease names. In the example illustrated in FIG. 34, since "nonneoplastic" is double clicked, the list of the small category disease names for nonneoplastic is displayed.

If the area in the lower section of FIG. 34 that displays the list of the small category disease names is clicked or double clicked by the user, the display control unit 104 can delete all the small category disease names displayed in the area.

The process performed by the information terminal 100 when user's operation on the disease name list display area 730 is input (a concomitant disease name listing process) is described below with reference to a flowchart illustrated in FIG. 35. For ease of description, description of a process to expand a large category disease name to reveal the small category disease names illustrated in FIG. 34 is not provided. Note that the process described below is applied to each of the disease name list display area 730 for the small category disease names (FIG. 31), the disease name list display area 730 for the large category disease names (FIG. 32), and the disease name list display area 730 for the large category disease names and the small category disease names (FIG. 33) in the same manner.

In step S3100, the input control unit 103 determines whether a search using two or more regions of interest is started. If the answer is No, that is, a search using only one region of interest is started, the processing proceeds to step S3200. However, if the answer is Yes, the processing proceeds to step S3300.

In step S3200, the input control unit 103 determines whether the mouse is clicked in the disease name list display area 730. If the answer is No, the processing returns to step S3200. However, if the answer is Yes, the processing proceeds to step S3210, where the input control unit 103 acquires the disease ID of the clicked disease name. For example, if "mycosis", which is one of the large category disease names, is clicked, the input control unit 103 detects that "mycosis" is clicked from the coordinates of the clicked point. Thereafter, the input control unit 103 refers to the disease classification system 5000 and acquires the disease ID "DIS011". For example, if "metastatic lung cancer", which is one of the small category disease names, is clicked, the input control unit 103 detects that "metastatic lung cancer" is clicked from the coordinates of the clicked point. Thereafter, the input control unit 103 refers to the disease classification system 5000 and acquires the disease ID "DIS002_004".

Subsequently, in step S3220, the display control unit 104 narrows down the search of the similar cases displayed in the case display area 710 within the similar cases corresponding to the disease ID acquired in step S3210. Thereafter, the display control unit 104 displays, in the case display area 710, similar cases that are the narrowed down results of the search and completes the processing. For example, if "mycosis", which is one of the large category disease names, is clicked, the display control unit 104 narrows down a search of the similar cases included in the disease name list information 6000 illustrated in FIGS. 29 to 14 similar cases (the similar case ID=SIM2205, SIM4172, SIM6089, . . . ) corresponding to mycosis (the disease ID=DIS011). Thereafter, the display control unit 104 displays, in the case display area 710, the similar cases that are the narrowed down result of the search (refer to FIG. 9).

For example, "metastatic lung cancer", which is one of the small category disease names, is clicked, the display control unit 104 narrows down a search of the similar cases contained in the disease name list information 6000 illustrated in FIG. 29 and obtains 3 similar cases (the similar case ID =SIM0157, . . . ) corresponding to metastatic lung cancer (the disease ID=DIS002_004). Thereafter, the display control unit 104 displays, in the case display area 710, the similar cases that are the results of the narrow down search (refer to FIG. 10).

In step S3300, the input control unit 103 determines whether the mouse is moved into the disease name list display area 730). If mouseover is performed in the disease name list display area 730 (YES in step S3300), the processing proceeds to step S3400. However, if mouseover is not performed in the disease name list display area 730 (NO in step S3300), the processing returns to step S3300. As used herein, the term "mouseover" refers to, for example, placing the mouse in the disease name list display area 730 at some position.

In step S3400, the input control unit 103 acquires the disease ID of a disease name located at the position of mouseover event. At that time, let x denote the acquired disease ID.

In step S3500, the display control unit 104 refers to the concomitant disease name list information 6500 and determines whether the concomitant disease ID associated with the disease ID (x) acquired in step S3400 is present. If the concomitant disease ID is not present (NO in step S3500), the processing returns to step S3300. However, if the concomitant disease ID is present (YES in step S3500), the processing proceeds to step S3600.

In step S3600, the display control unit 104 acquires, from the concomitant disease name list information 6500, the concomitant disease ID and the number of cases associated with the disease ID (x) and displays the disease name indicated by the acquired concomitant disease ID and the number of cases in the disease name list display area 730.

Figure 37:
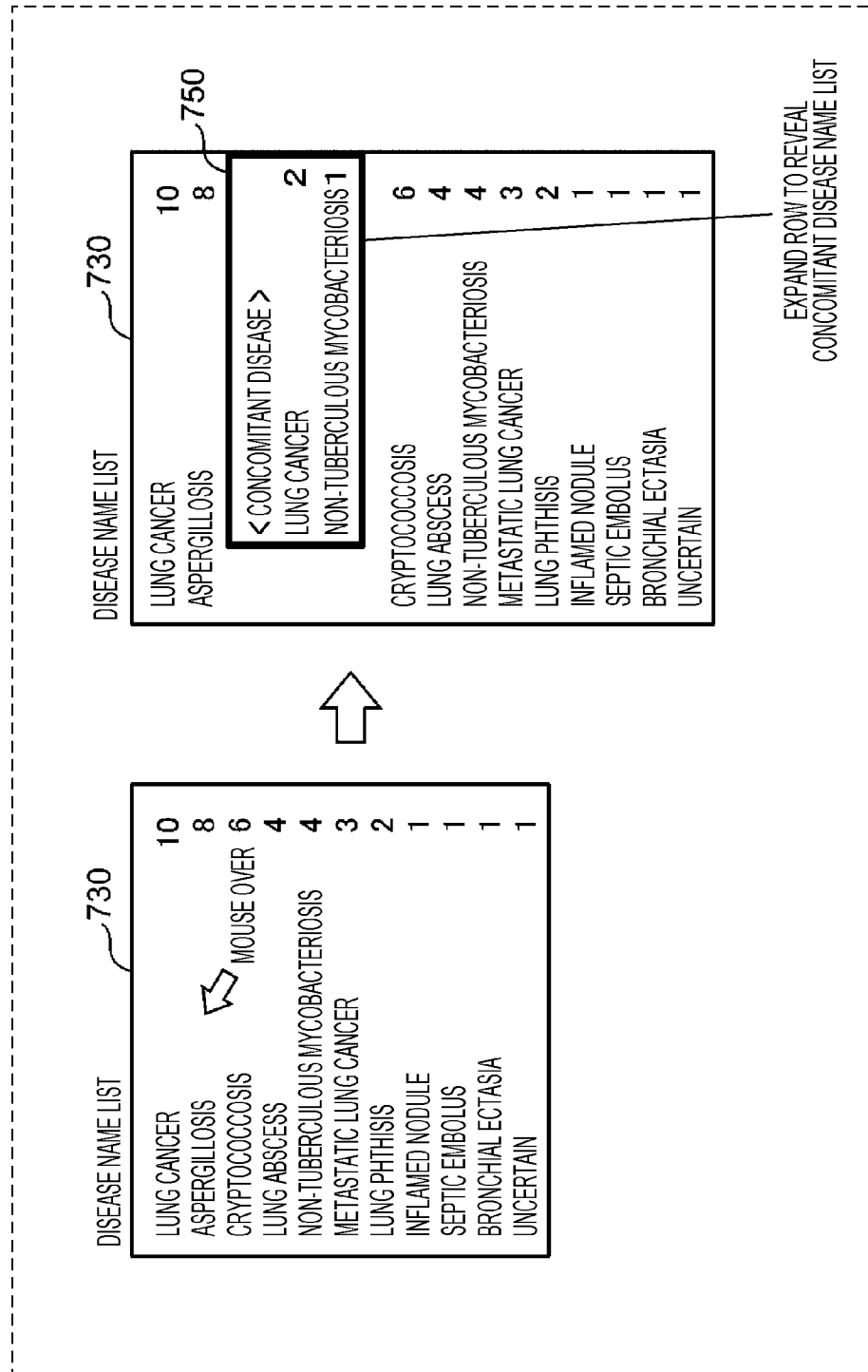
FIG. 37 illustrates a first example of a concomitant disease name list.

For example, as illustrated in FIG. 31, suppose that mouse is moved over "aspergillosis" when the disease name list display area 730 displays the small category disease names. In such a case, the display control unit 104 determines that the mouse is moved over "aspergillosis" from the point of the mouseover event. Thus, the display control unit 104 refers to the concomitant disease name list information 6500 and acquires the concomitant disease IDs (DIS002_001, DIS003_002) corresponding to aspergillosis (DIS011_002) and the number of cases (3=2+1). Thereafter, the display control unit 104 refers to the disease classification system 5000 and acquires the small category disease names corresponding to the acquired concomitant disease IDs. In this example, " lung cancer" and "non-tuberculous mycobacteriosis" are acquired as small category disease names, and "two cases" and "one case" are obtained for "lung cancer" and the "non-tuberculous mycobacteriosis", respectively, as the number of cases. Subsequently, as illustrated in FIG. 37, the display control unit 104 inserts a concomitant disease name list 750 that displays a list of the concomitant diseases of "aspergillosis" immediately below "aspergillosis" on which mouseover occurred. Thus, the concomitant disease name list 750 is displayed. FIG. 37 illustrates a first example of the concomitant disease name list 750. The concomitant disease name list 750 is an example of a combination list of a concomitant disease name. In the example of the concomitant disease name list 750 illustrated in FIG. 37, lung cancer and nontuberculous mycobacteria are displayed together with the numbers of cases of "2" and "1", respectively, under the caption "<Concomitant Disease>". In addition, since the number of cases for "lung cancer" is greater than that for "nontuberculous mycobacteria", "lung cancer" is displayed first and "nontuberculous mycobacteria" is displayed next in the concomitant disease name list 750.

Figure 38:
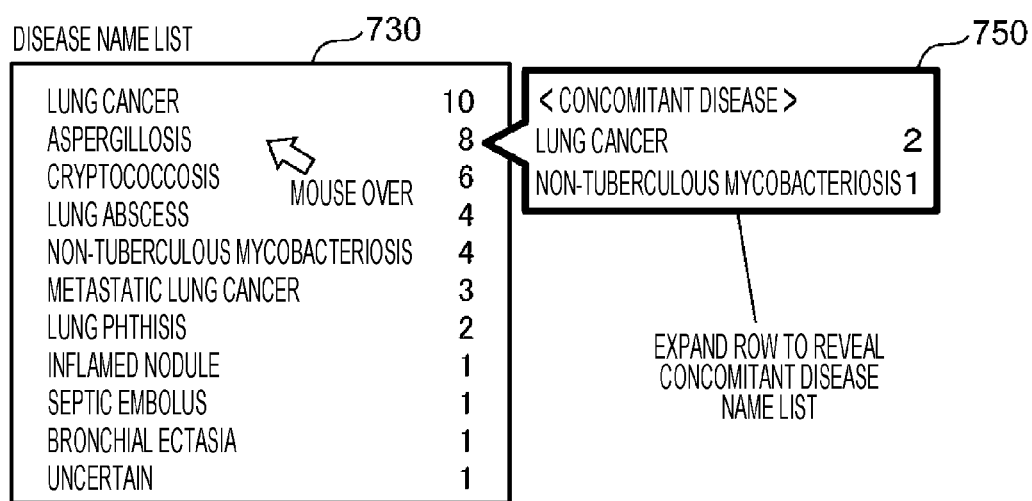
FIG. 38 illustrates a second example of the concomitant disease name list.

FIG. 38 illustrates the second example of the concomitant disease name list 750. In the example illustrated in FIG. 38, the concomitant disease name list 750 is not inserted into the disease name list display area 730, but is displayed in a pop-up window. In the example illustrated in FIG. 38, the concomitant disease name list 750 is displayed in a pop-up window that pops up at the display region of "aspergillosis".

Figure 39:
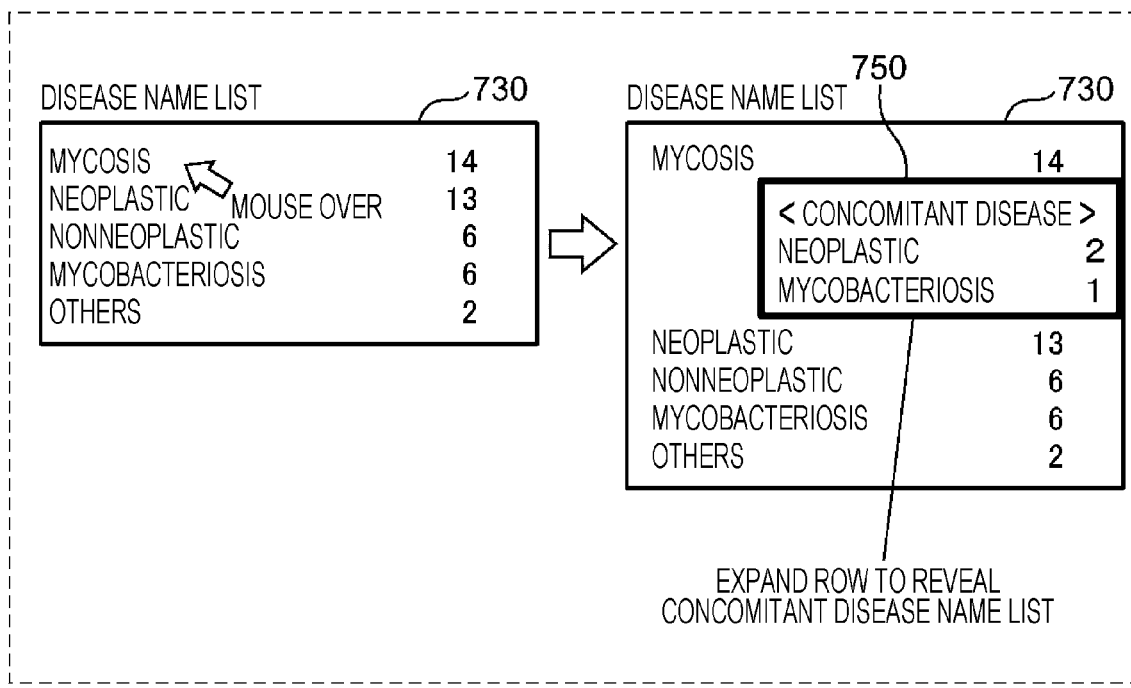
FIG. 39 illustrates a third example of the concomitant disease name list.
Figure 40:
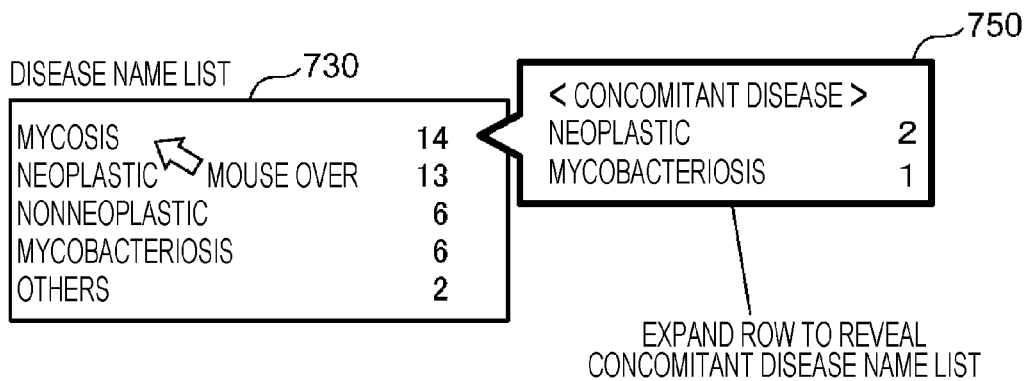
FIG. 40 illustrates a fourth example of the concomitant disease name list.

If, as illustrated in FIG. 32, the disease name list display area 730 is displayed using the large category disease names, the concomitant disease name list 750 that, as illustrated in FIGS. 39 and 40, displays the list of the concomitant diseases using the large category disease names can be employed. FIG. 39 illustrates a third example of the concomitant disease name list 750. FIG. 40 illustrates a fourth example of the concomitant disease name list 750.

In the example illustrated in FIG. 39, since the mouse is moved over "mycosis", the concomitant disease name list 750 is displayed immediately below "mycosis". In this example, the concomitant diseases of "mycosis" are "neoplastic" and "mycobacteriosis". Since the number of cases for "neoplastic" is greater than that for "mycobacteriosis", "neoplastic" is displayed first and "mycobacteriosis" is displayed next in the concomitant disease name list 750.

The concomitant disease name list 750 illustrated in FIG. 40 is obtained by displaying the third example of the concomitant disease name list 750 illustrated in FIG. 39 in a pop-up window.

Note that as illustrated in FIGS. 41 to 44, when as illustrated in FIG. 33, the disease name list display area 730 is displayed using the large category disease names and the small category disease names, the display control unit 104 may display the concomitant disease name list 750 that displays the list of concomitant diseases using the large category disease names if the mouse is moved over a large category disease name. In contrast, if the mouse is moved over a small category disease name, the concomitant disease name list 750 that displays the list of the concomitant diseases using the small category disease names may be displayed.

Figure 42:
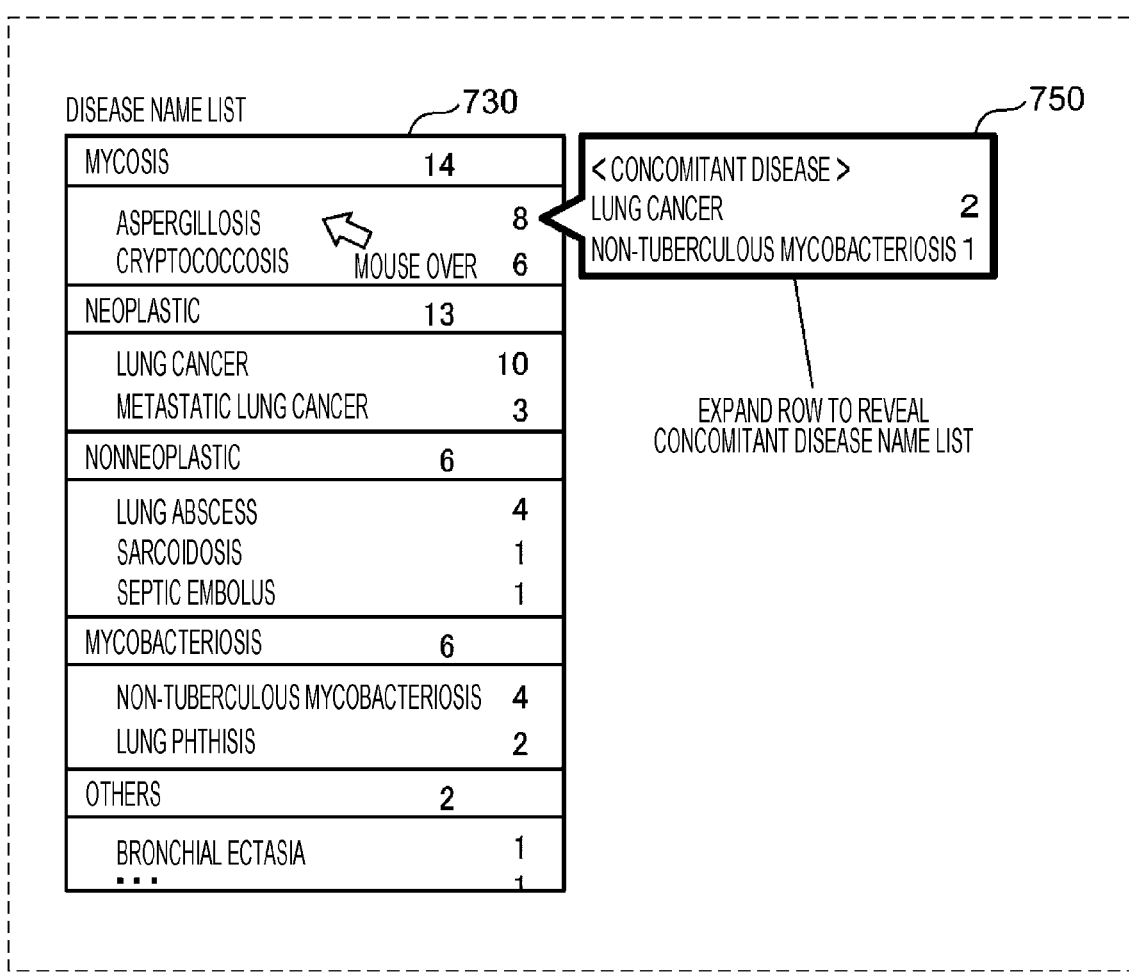
FIG. 42 illustrates a sixth example of the concomitant disease name list.
Figure 43:
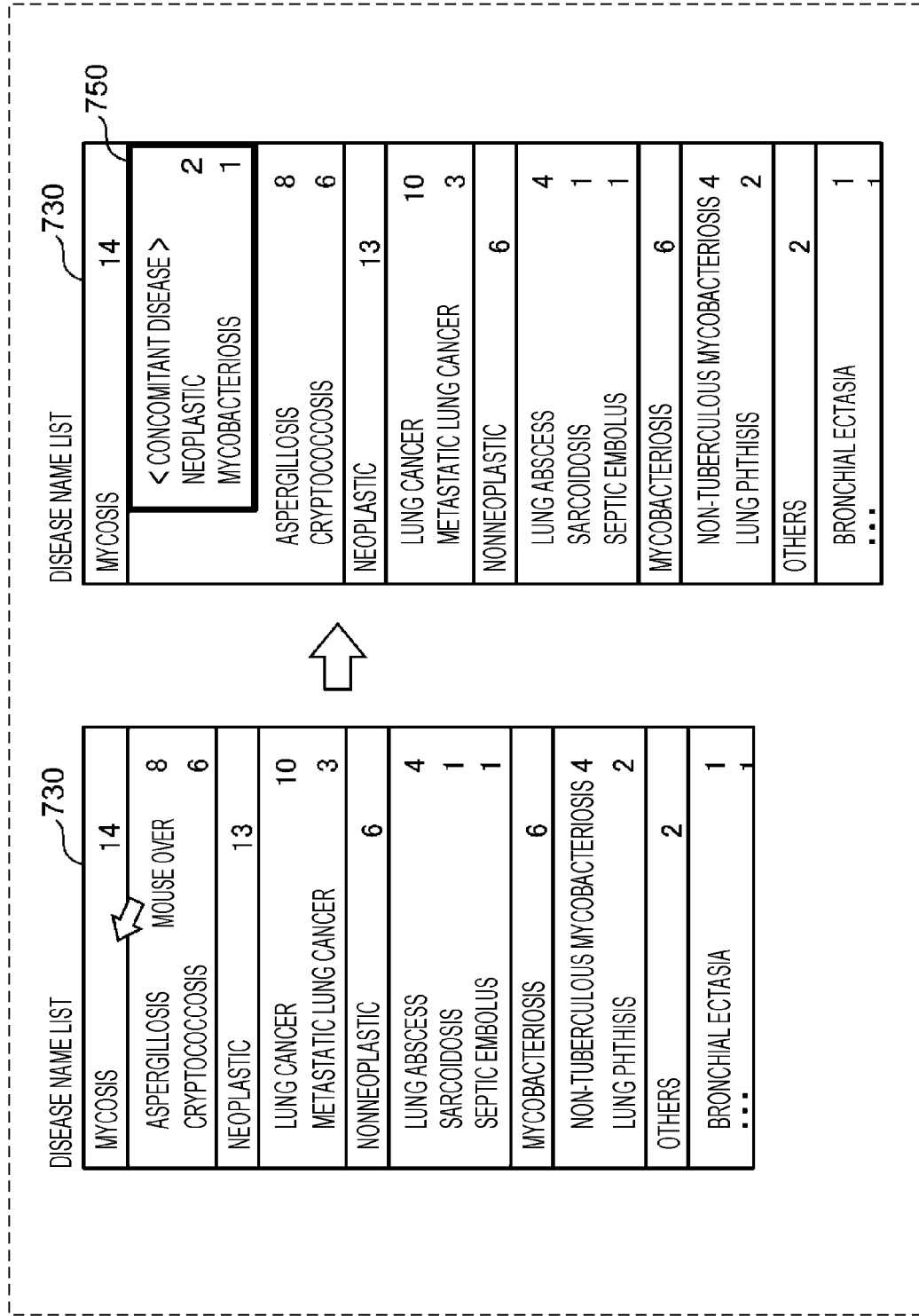
FIG. 43 illustrates a seventh example of the concomitant disease name list.
Figure 44:
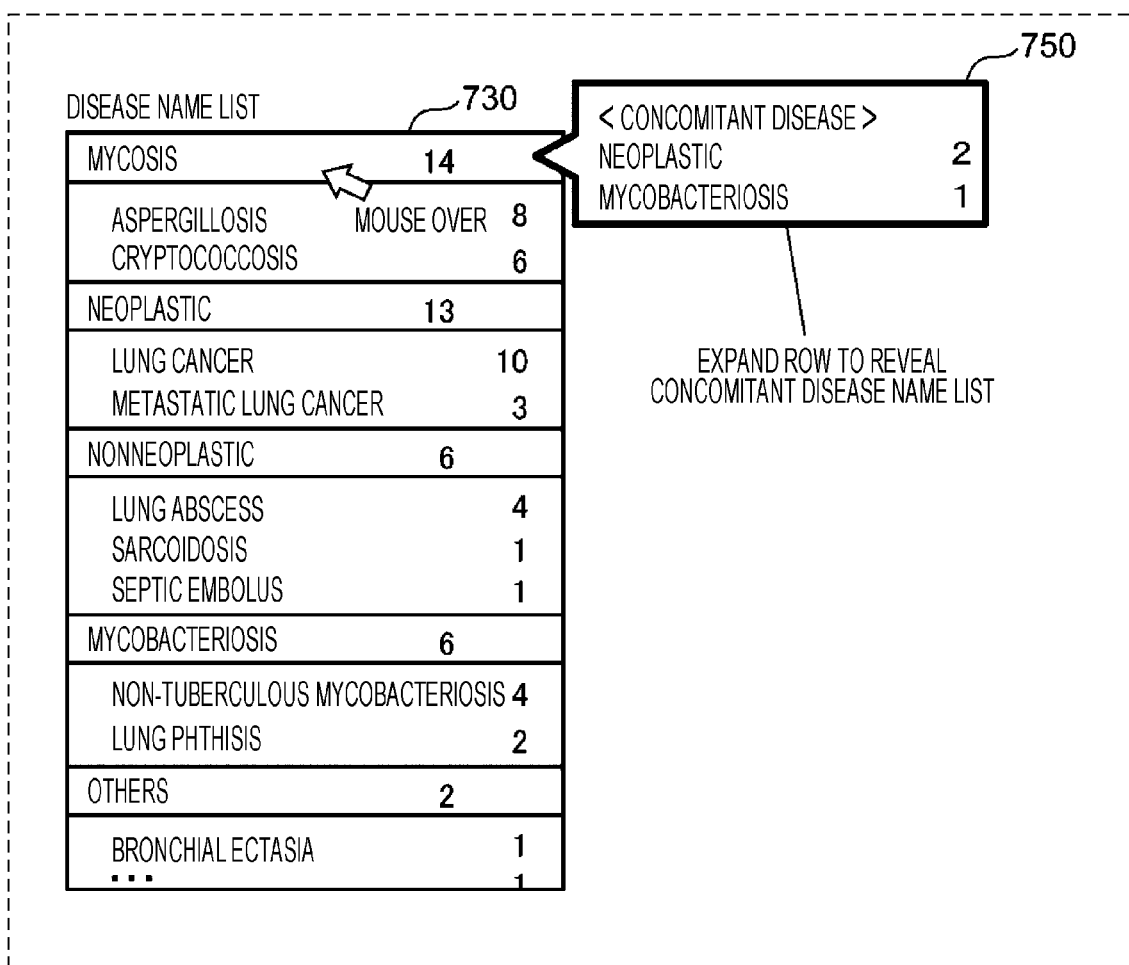
FIG. 44 illustrates an eighth example of the concomitant disease name list.

FIG. 41 illustrates a fifth example of the concomitant disease name list 750. FIG. 42 illustrates a sixth example of the concomitant disease name list 750. FIG. 43 illustrates a seventh example of the concomitant disease name list 750. FIG. 44 illustrates an eighth example of the concomitant disease name list 750.

In the left section of FIG. 41, the mouse is moved over "aspergillosis", which is a small category disease name, in the disease name list display area 730. Accordingly, in the right section of FIG. 41, the concomitant disease name list 750 that displays the list containing "lung cancer" and "nontuberculous mycobacteria", which are the concomitant diseases of "aspergillosis", is displayed immediately under "aspergillosis".

The concomitant disease name list 750 illustrated in FIG. 42 is obtained by displaying the fifth example of the concomitant disease name list 750 illustrated in FIG. 41 in a pop-up window.

In the left section of FIG. 43, the mouse is moved over "mycosis", which is a large category disease names, in the disease name list display area 730. Accordingly, in the right section of FIG. 43, the concomitant disease name list 750 that displays the list containing "neoplastic" and "mycobacteriosis", which are the concomitant diseases of "mycosis", is displayed immediately under "mycosis".

The concomitant disease name list 750 illustrated in FIG. 44 is obtained by displaying the seventh example of the concomitant disease name list 750 illustrated in FIG. 43 in a pop-up window.

Note that in the concomitant disease name lists 750 illustrated in FIGS. 37 to 44, each of the concomitant diseases is displayed together with the number of cases. However, for a disease name having no concomitant disease, a text "alone" may be appended to the disease name, and the number of cases may be displayed. For example, in the example illustrated in FIG. 37, the row "aspergillosis alone 5" may be additionally displayed. In this manner, the user can clearly understand that among a total of 8 cases related to aspergillosis, 2 cases include the concomitant disease "lung cancer", 1 case includes the concomitant disease "nontuberculous mycobacteria", and 5 cases include aspergillosis that occurs alone.

Note that in step S3300, the concomitant disease name list 750 is displayed when a mouseover event is triggered. However, the mouseover event is only illustrative. For example, the concomitant disease name list 750 may be displayed when a click, double click, left-click, or right click event is triggered. Alternatively, after a click, double click, left-click, or right click event is triggered, a menu list for selecting whether the concomitant disease name list 750 is displayed may be displayed. If display of the concomitant disease name list 750 is selected in the menu list, the concomitant disease name list 750 may be displayed. In either case, the concomitant disease name list 750 can be displayed when an operation that differs from the operation of FIG. 34 to expand a large category disease name to reveal the small category disease names is performed.

Referring back to FIG. 35, in step S3700, the input control unit 103 waits until a mouse click on the area of the concomitant disease name list 750 is detected. If a mouse click is not detected (NO in step S3700), step S3700 is repeated. However, if a mouse click is detected (YES in step S3700), the processing proceeds to step S3800, where the display control unit 104 acquires a concomitant disease ID corresponding to the concomitant disease name on which the mouse is clicked. Let Y denote the acquired disease ID.

Figure 45:
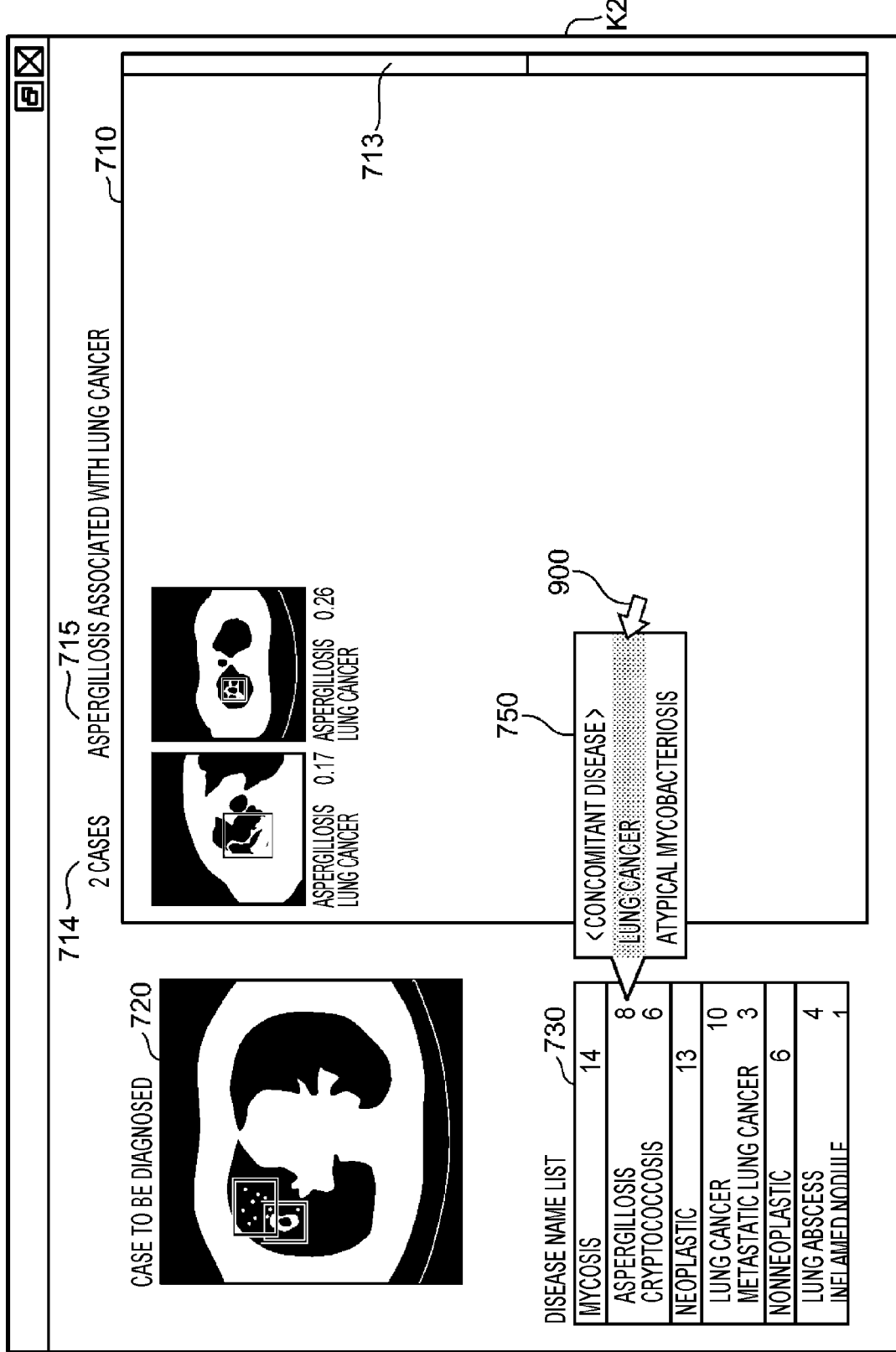
FIG. 45 illustrates an example of a narrowed search of similar cases conducted by selecting a disease in the concomitant disease name list.

Subsequently, in step S3900, the display control unit 104 refers to the row of the concomitant disease name list information 6500 having the disease ID=X and the concomitant disease ID=Y and acquires the similar case IDs equal in number to the number in the "number of cases" field. For example, in FIG. 30, if the disease ID=DIS011_002 (aspergillosis) and the concomitant disease ID=DIS002_001 (lung cancer) are acquired, the number in the "number of cases" field is equal to "2". Accordingly, the display control unit 104 acquires two similar case IDs (SIM2205, SIM8137). Thereafter, the display control unit 104 narrows down a search of the similar cases displayed in the case display area 710 within the similar cases corresponding to the acquired similar case ID. FIG. 45 illustrates an example of the above-described process.

In the example illustrated in FIG. 45, the results of the search for similar cases related to aspergillosis are narrowed down to the similar cases having a concomitant disease of "lung cancer". Accordingly, "2 cases" is displayed in the case count display area 714 as the number of cases, and "aspergillosis associated with lung cancer" is displayed in the disease condition display area 715. Note that this text is only illustrative. For example, the text "aspergillosis AND lung cancer" may be displayed in the disease condition display area 715.

Figure 46:
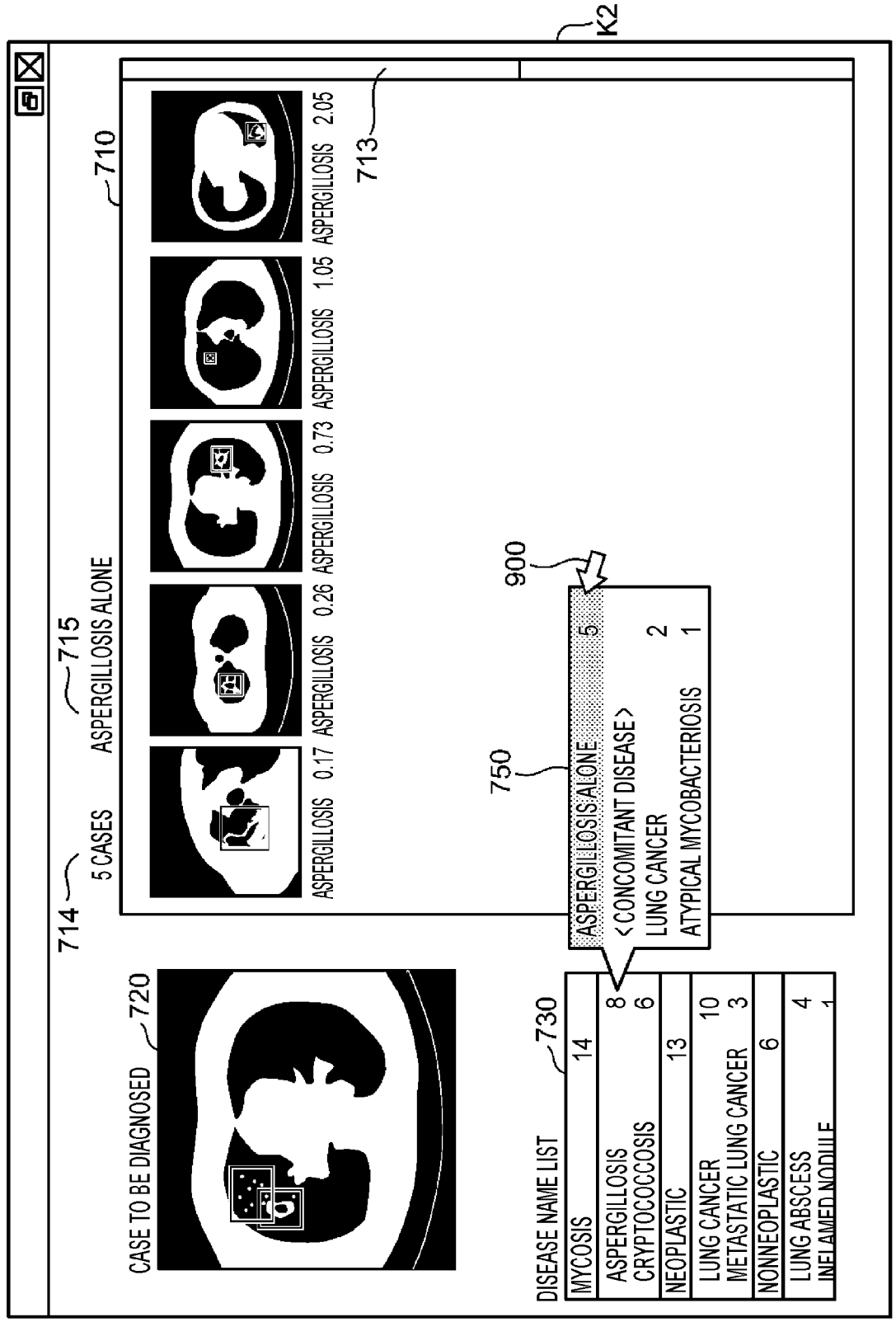
FIG. 46 illustrates an example of a narrowed search of similar cases conducted by selecting a disease in the concomitant disease name list.

Note that if the concomitant disease name list 750 is configured to have the row "aspergillosis alone", the display control unit 104 can display, in the case display area 710, only the similar cases in which aspergillosis occurs alone, as illustrated in FIG. 46.

As described above, according to the present exemplary embodiment, since the concomitant disease name list 750 is displayed, the user can easily diagnose whether the search query image is associated with a plurality of diseases. More specifically, the number of cases is displayed in the concomitant disease name list 750. Accordingly, by referencing the frequency of the case, the user can determine what diseases each of the similar cases of the search query image has.

In addition, as illustrated in FIG. 45, by selecting the concomitant disease (lung cancer) displayed in the concomitant disease name list 750, similar cases in which the disease from which the concomitant disease name list 750 is popped up (i.e., aspergillosis) and the selected concomitant disease occur are displayed in the case display area 710. Thus, the user can easily determine whether the search query image indicates that the disease from which the concomitant disease name list 750 is popped up and the selected concomitant disease occur at the same time.

Note that a physician wants to examine the possibility of the occurrence of a plurality of diseases without setting a plurality of regions of interest, a manual start mode of the concomitant disease name list 750 may be provided to display the concomitant disease name list 750. Modification of First Exemplary Embodiment A modification of the first exemplary embodiment is described below. In the modification, the elements and processes that are not described are the same as those of the first exemplary embodiment, unless expressly specified otherwise.

Figure 47:
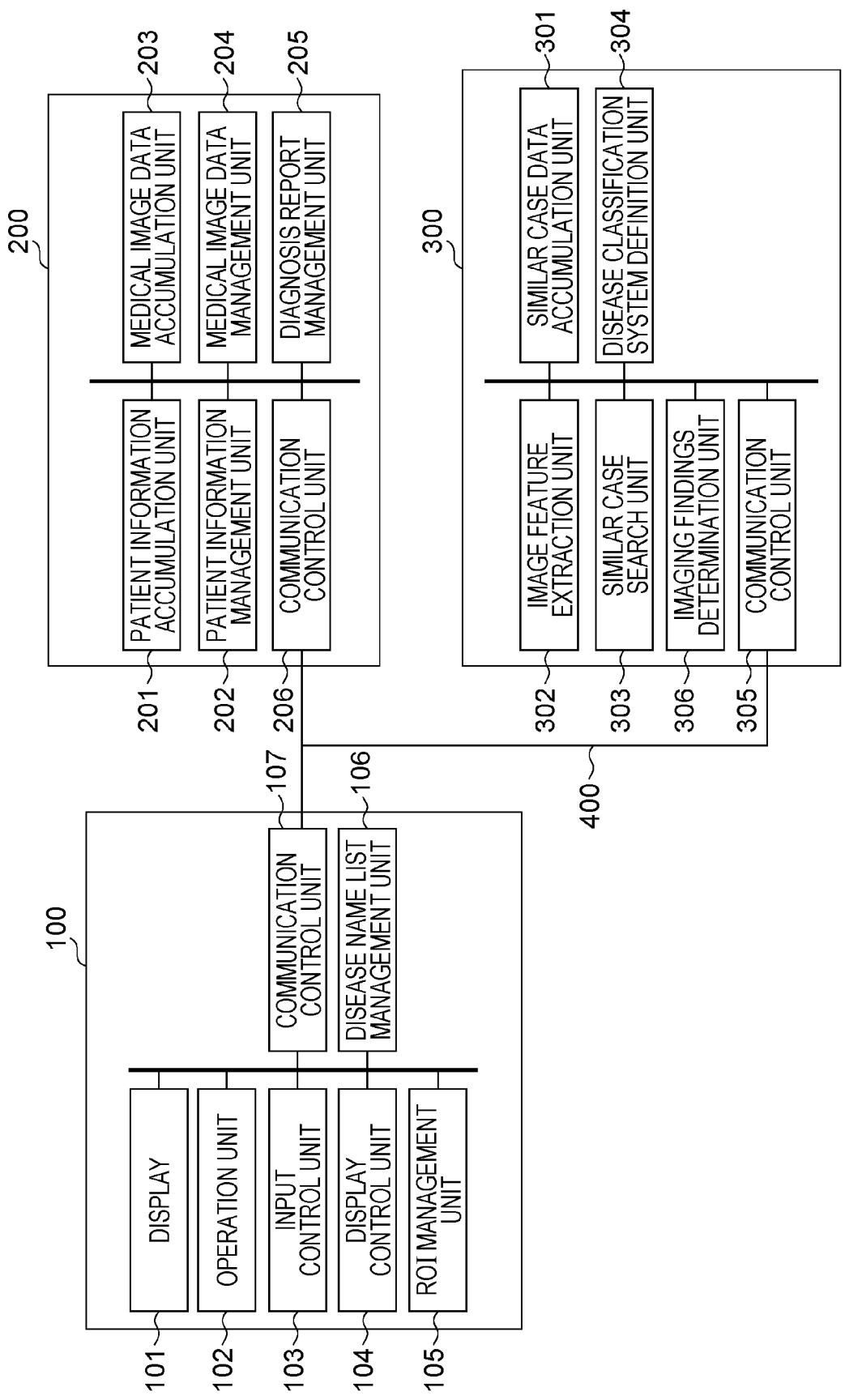
FIG. 47 is a block diagram illustrating the configurations of an information terminal, a medical information management system, and a case search system according to a modification of the first exemplary embodiment.

FIG. 47 is a block diagram illustrating the configurations of an information terminal 100, a medical information management system 200, and a case search system 300 according to the modification of the present exemplary embodiment. Unlike the first exemplary embodiment, according to the modification, the case search system 300 includes an imaging findings determination unit 306. The imaging findings determination unit 306 determines whether a plurality of (different) imaging findings are contained in a plurality of regions of interest set by the information terminal 100.

Figure 48:
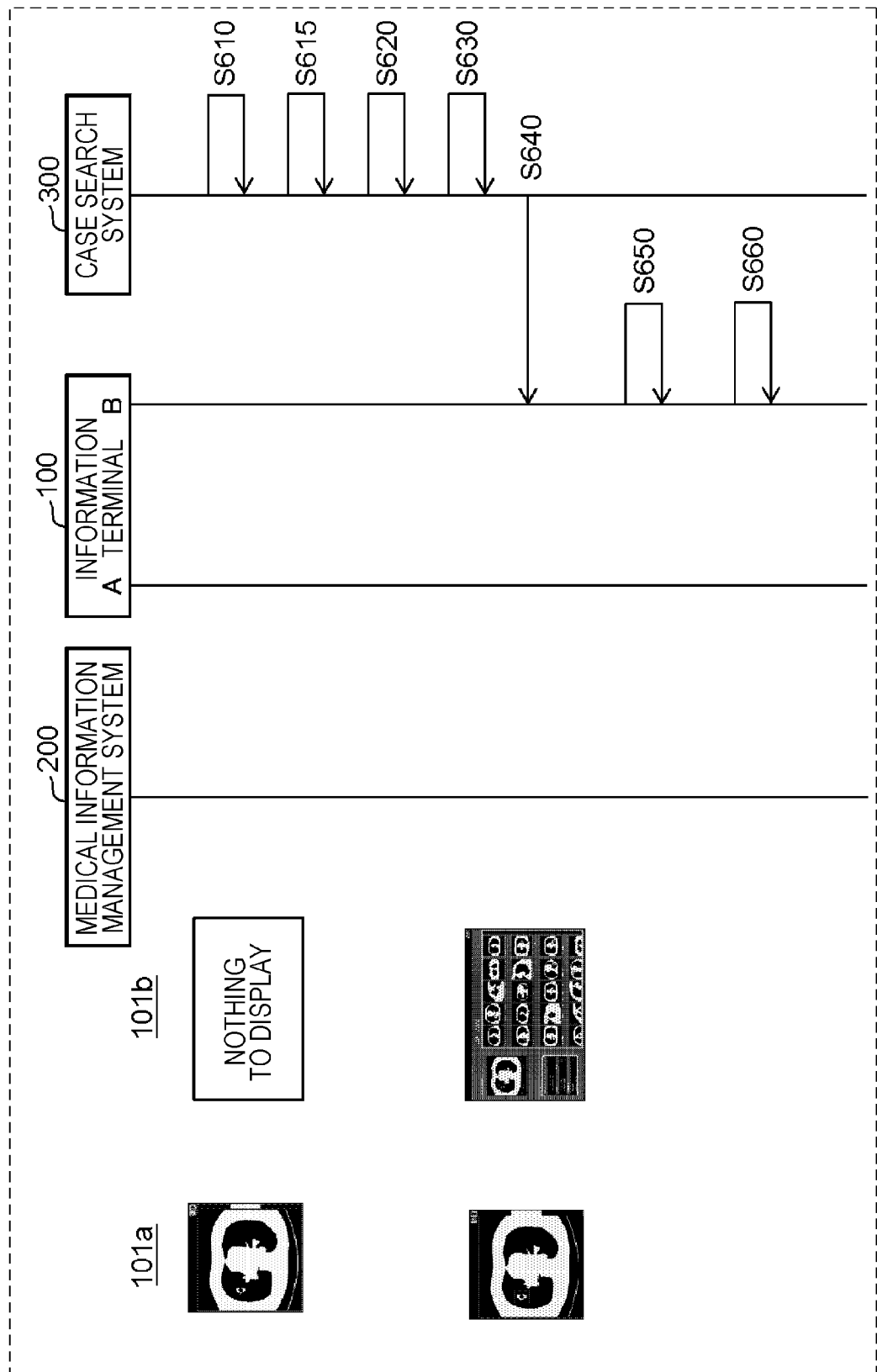
FIG. 48 is a sequence diagram illustrating the processes performed after the case search system receives a request for a similar case search until the result of the similar case search is returned to the information terminal according to the modification of the first exemplary embodiment.

FIG. 48 is a sequence diagram illustrating the processes performed after the case search system 300 receives a request for a similar case search until the result of the similar case search is returned to the information terminal 100. Note that the sequence diagram in the first stage illustrated in FIG. 48 is the same as that of FIG. 17 of the first exemplary embodiment. In step S610 of FIG. 48, the image feature extraction unit 302 of the case search system 300 extracts an image feature set from one or more pieces of the region-of-interest information and the slice images sent in step S601 for each of the regions of interest.

In step S615, if a plurality of regions of interest are set by the information terminal 100, the imaging findings determination unit 306 determines whether different imaging findings are contained.

Figure 49:
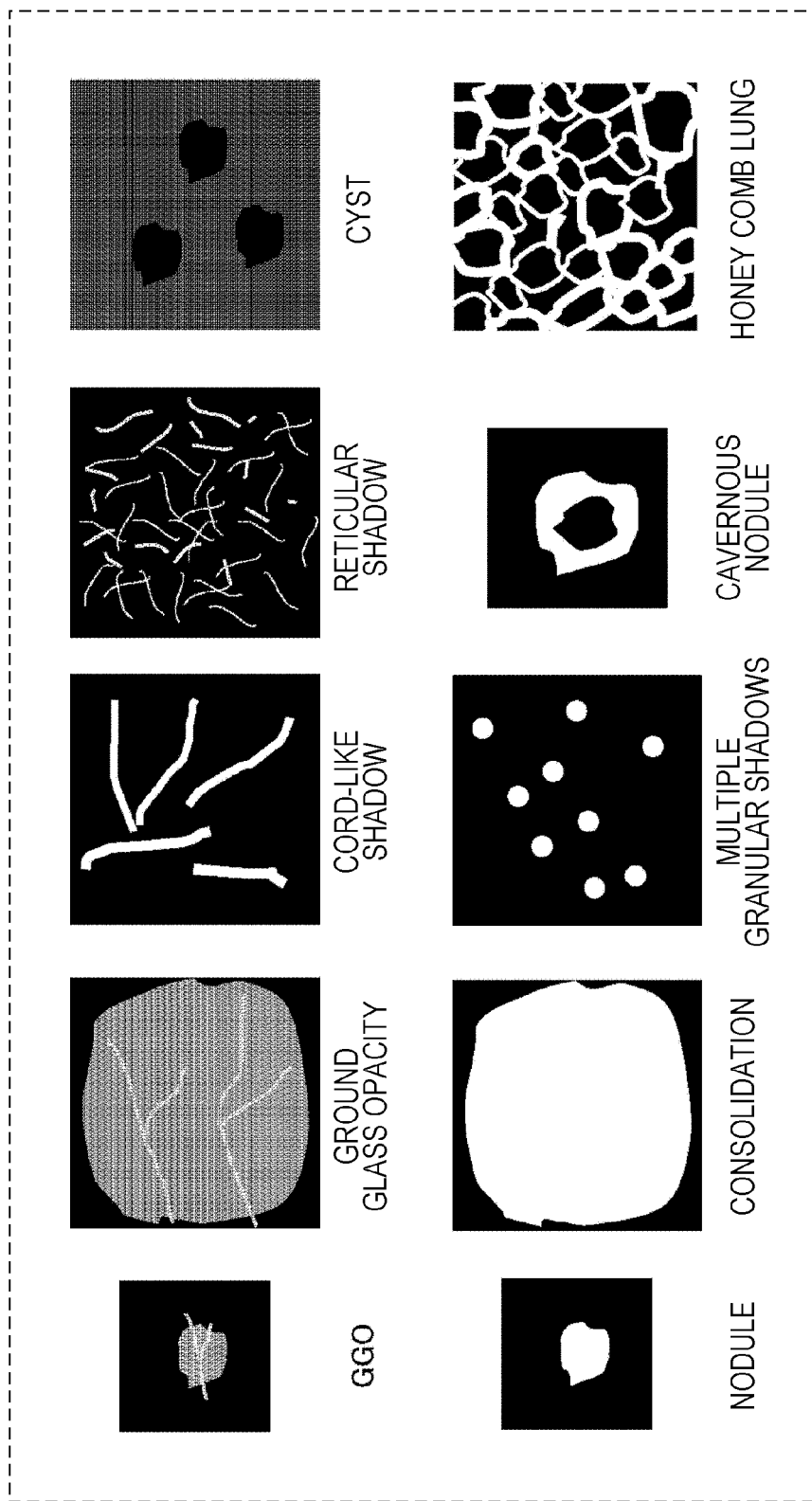
FIG. 49 illustrates predetermined and pre-classified imaging findings.

The imaging findings determination unit 306 includes a classifier for classifying the image feature sets each corresponding to one of the regions of interest into a plurality of number of imaging findings. For example, as illustrated in FIG. 49, the imaging findings determination unit 306 extracts image feature sets from several hundreds to several thousands of images collected in advance for each of 10 imaging findings predetermined by the radiologist. Thereafter, the imaging findings determination unit 306 generates the classifier through learning using the extracted image feature sets. In the example illustrated in FIG. 49, 10 imaging findings, that is, "GGO", "ground glass opacities", "cord-like shadows", "reticular shadows", "cyst", "nodule", "consolidation", "multiple granular shadows", "cavernous nodule", and "honey comb lung" are employed. However, these imaging findings are only examples.

For example, a support vector machine (SVM), logistic regression, or artificial neural networks (ANN) can be used as the classifier. Note that the imaging findings need not be the same as those in FIG. 49. Another classification method and another number of categories may be employed if the number is in the range from several to several tens.

Referring back to FIG. 48, in step S615, the imaging findings determination unit 306 inputs the image feature set extracted in step S610 for each of the regions of interest set by the user in the information terminal 100 and determines how many types of imaging findings are present. For example, as illustrated in FIG. 5, suppose that two regions of interest ROI_A and ROI_B are set. In such a case, the image feature set of the region of interest ROI_A is identified as "cavernous nodule" illustrated in FIG. 49, and the image feature set of the region of interest ROI_B is identified as "multiple granular shadows" illustrated in FIG. 49. Consequently, the number of the results of determination in step S615 is two.

Figure 50:
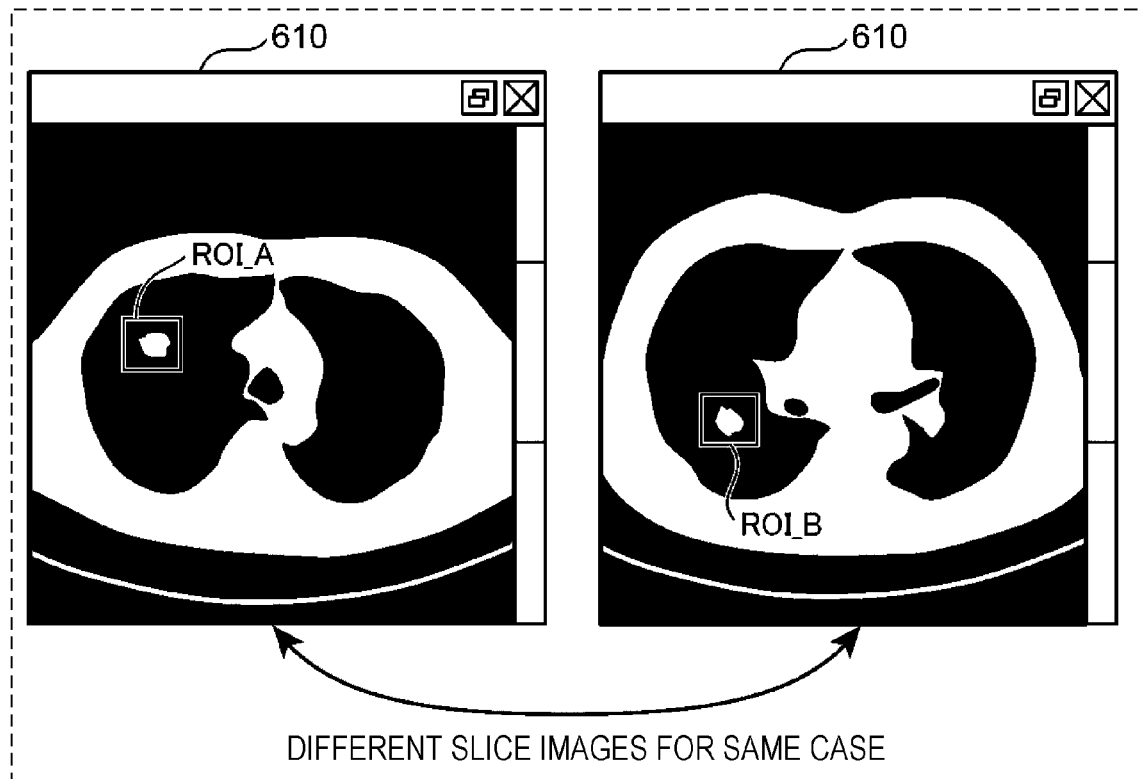
FIG. 50 illustrates an example of setting of a region of interest according to the modification of the first exemplary embodiment.

For example, suppose that two regions of interest ROI_A and ROI_B are set, as illustrated in FIG. 50. In such a case, the image feature sets of the two regions of interest ROI_A and ROI_B are identified as "nodule" illustrated in FIG. 49. Consequently, the number of the results of determination in step S615 is one.

As illustrated in FIG. 50, a region of interest may be set for a lesion of each of two slice images in the same series. In such a case, if the number of the results of determination made in step S615 is one, the imaging findings determination unit 306 determines that different imaging findings are not included in the plurality of regions of interest set in the information terminal 100. However, if the number of the results of determination made in step S615 is two, the imaging findings determination unit 306 determines that different imaging findings are included in the plurality of regions of interest set in the information terminal 100. Even when three or more regions of interest are set, the imaging findings determination unit 306 performs a process that is the same as the above-described process to determine whether different imaging findings are included in the regions of interest.

Note that another type of classifier may be employed if the classifier can identify the input image feature set as a predetermined imaging finding.

Figure 51:
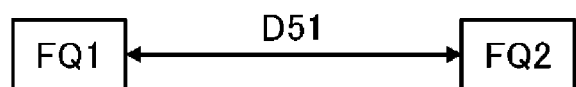
FIG. 51 illustrates comparison of a plurality of image feature sets extracted from a search query image according to the modification of the first exemplary embodiment.

Alternatively, the classifier may be removed from the imaging findings determination unit 306. For example, the imaging findings determination unit 306 may determine whether different imaging findings are included in the regions of interest by comparing a plurality of image feature sets extracted in step S610 with each other. For example, suppose that two regions of interest are set, and let FQ1 and FQ2 denote the image feature sets extracted from the two regions of interest. Then, as illustrated in FIG. 51, the imaging findings determination unit 306 calculates a distance D51 between the image feature set FQ1 and the image feature set FQ2. Thereafter, if the distance D51 is less than a predetermined threshold value, the imaging findings determination unit 306 can determine that different imaging findings are not included in the plurality of regions of interest set in the information terminal 100. However, if the distance D51 is greater than or equal to the predetermined threshold value, the imaging findings determination unit 306 can determine that different imaging findings are included in the plurality of regions of interest set in the information terminal 100.

Figure 52:
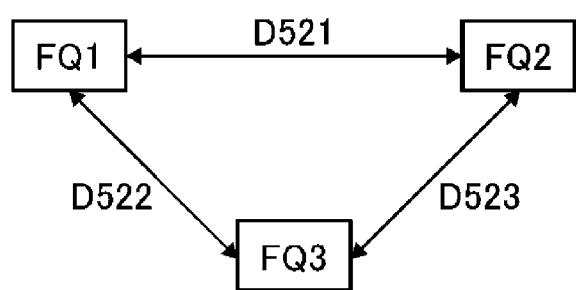
FIG. 52 illustrates comparison of a plurality of image feature sets extracted from a search query image according to the modification of the first exemplary embodiment.

If three regions of interest are set, the imaging findings determination unit 306 calculates a distance D521 between the image feature sets FQ1 and FQ2, a distance D522 between the image feature sets FQ1 and FQ3, and a distance D523 between the image feature sets FQ2 and FQ3, as illustrated in FIG. 52. If all the distances D521, D522, and D523 are less than a predetermined threshold value, the imaging findings determination unit 306 can determine that different imaging findings are not included in the regions of interest set in the information terminal 100. However, if at least one of the distances D521, D522, and D523 is greater than or equal to the predetermined threshold value, the imaging findings determination unit 306 can determine that different imaging findings are included in the regions of interest set in the information terminal 100. Note that even when four or more regions of interest are set, the imaging findings determination unit 306 can perform a process that is the same as the above-described process to determine whether different imaging findings are included in the regions of interest.

Referring back to FIG. 48, the processes performed in steps S620 to S650 are the same as the processes performed in steps S620 to S650 illustrated in FIG. 21, respectively.

Figure 53:
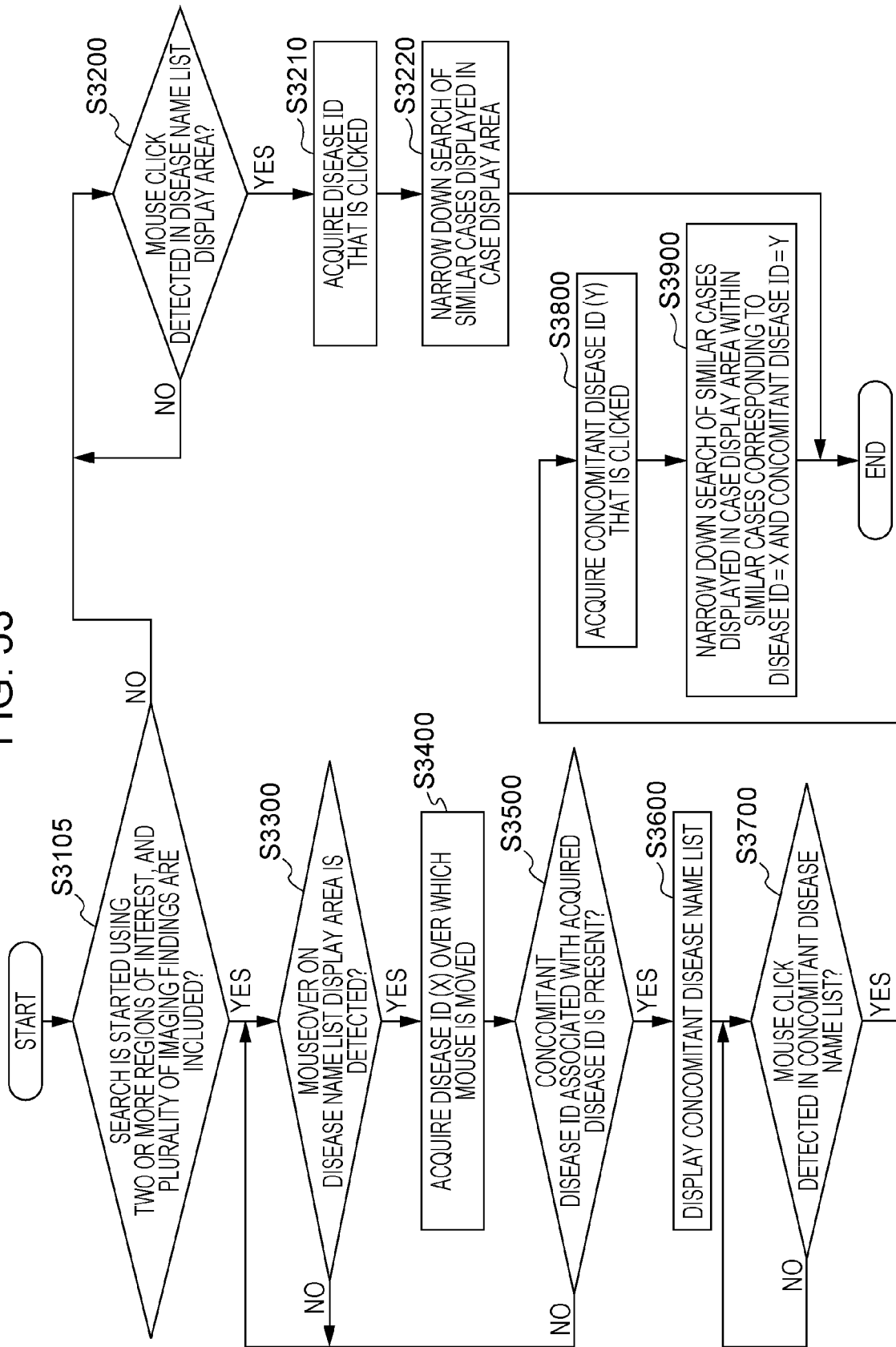
FIG. 53 is a flowchart of a concomitant disease name listing process according to the modification of the first exemplary embodiment.

Subsequently, if the input control unit 103 detects user's operation performed on the disease name list display area 730 of the basic screen K2, the display control unit 104 and the imaging findings determination unit 306 perform a process corresponding to the detected operation (S660). The process performed by the information terminal 100 when the operation on the disease name list display area 730 is input (the concomitant disease name listing process) is described below with reference to a flowchart illustrated in FIG. 53.

In step S3105, the input control unit 103 and the imaging findings determination unit 306 determine whether search is started using two or more regions of interest and whether a plurality of imaging findings are included in the two or more regions of interest. If the answer is No, that is, if the search is started using one region of interest, the processing proceeds to step S3200. However, the answer is Yes, the processing proceeds to step S3300. Note that the determination as to whether search is started using two or more regions of interest is the same as the determination made in step S3100 according to the first exemplary embodiment. To determine whether a plurality of imaging findings are included in the two or more regions of interest, the result obtained in step S615 illustrated in FIG. 48 is used.

Figure 35:
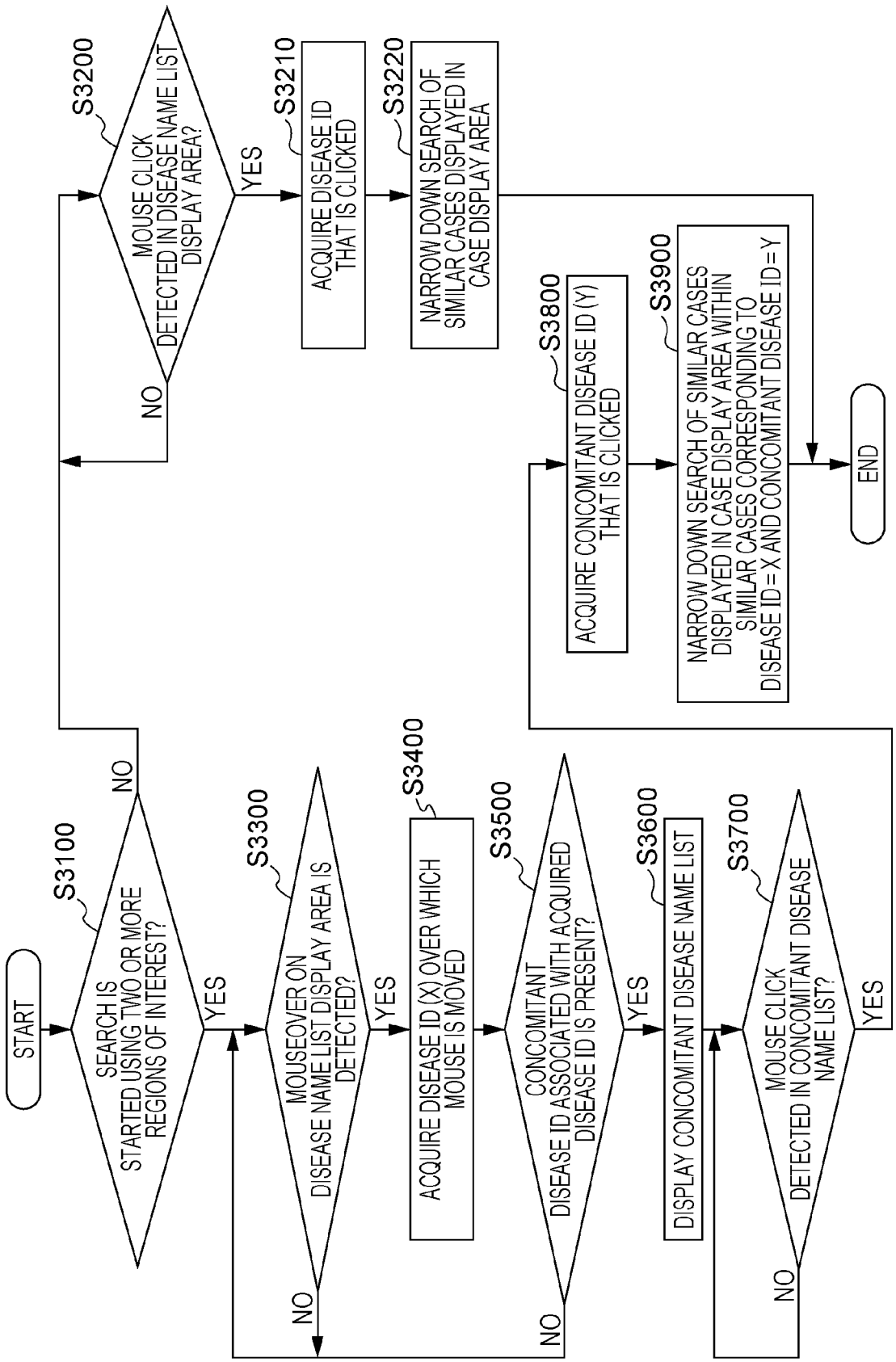
FIG. 35 is a flowchart of a concomitant disease name listing process.

The processes performed in the subsequent steps are the same as the processes performed in the first exemplary embodiment (refer to FIG. 35).

Like the first exemplary embodiment, according to the modification of the first exemplary embodiment, the concomitant disease name list 750 is displayed. Accordingly, the user can easily diagnose whether a plurality of diseases occur in the case to be diagnosed. In addition, according to the modification of the first exemplary embodiment, search is started using a plurality of regions of interest. In addition, the concomitant disease name list 750 is displayed when a plurality of imaging findings are included in the plurality of regions of interest. That is, only when a plurality of diseases are highly likely to occur at the same time, the concomitant disease name list 750 is displayed. Accordingly, when a plurality of diseases are less likely to occur at the same time, the physician can focus on diagnosis of a single disease.

The reason why the concomitant disease name list 750 is displayed when a plurality of imaging findings are included in a plurality of regions of interest is as follows.

That is, a plurality of regions of interest are set in the following cases: case 1 and case 2.

(Case 1) As illustrated in FIG. 5, since different lesions are present in the search query image, a region of interest is set for each of the lesions.

(Case 2) As illustrated in FIG. 50, the same lesion is present in different slice images. In such a case, it is desirable that the settings of the region of interest include the information indicating multiple lesions. However, a region of interest is not allowed to be set on a multi-slice image basis. Thus, a region of interest is set for each of different slice images.

In the case of the same lesion appearing in different slice images of the case to be diagnosed, it is highly likely that the patient has not a plurality of diseases but one disease. Thus, according to the modification of the first exemplary embodiment, the condition "a plurality of imaging findings are included in a plurality of regions of interest" is provided to display the concomitant disease name list 750.

Second Exemplary Embodiment

The second exemplary embodiment is described below. In the second exemplary embodiment, the elements and processes that are not described are the same as those of the first exemplary embodiment, unless expressly specified otherwise.

According to the second exemplary embodiment, the processes performed after the information terminal 100 receives a case to be diagnosed from the medical information management system 200 and sends a request for a similar case search to the case search system 300 until the case search system 300 receives the request for a similar case search is described with reference to FIG. 17. Note that FIG. 17 is the same as that described in the first exemplary embodiment.

Figure 54:
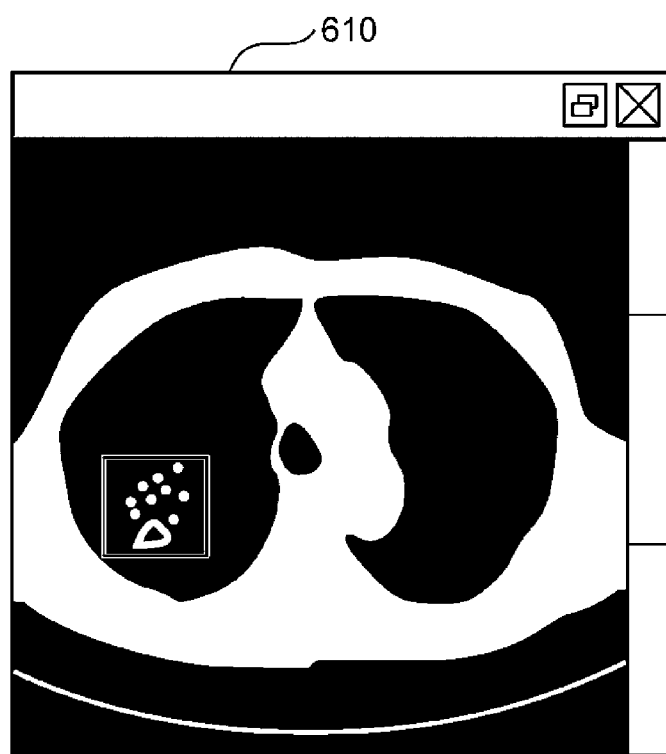
FIG. 54 illustrates an example of setting of a region of interest according to a second exemplary embodiment.

According to the second exemplary embodiment, as illustrated in FIG. 54, a region of interest (ROI) set in step S580 includes two types of lesion. In the example illustrated in FIG. 54, a lesion having a cavernous nodule and a lesion having multiple granular shadows are illustrated as the two types of lesion.

Figure 55:
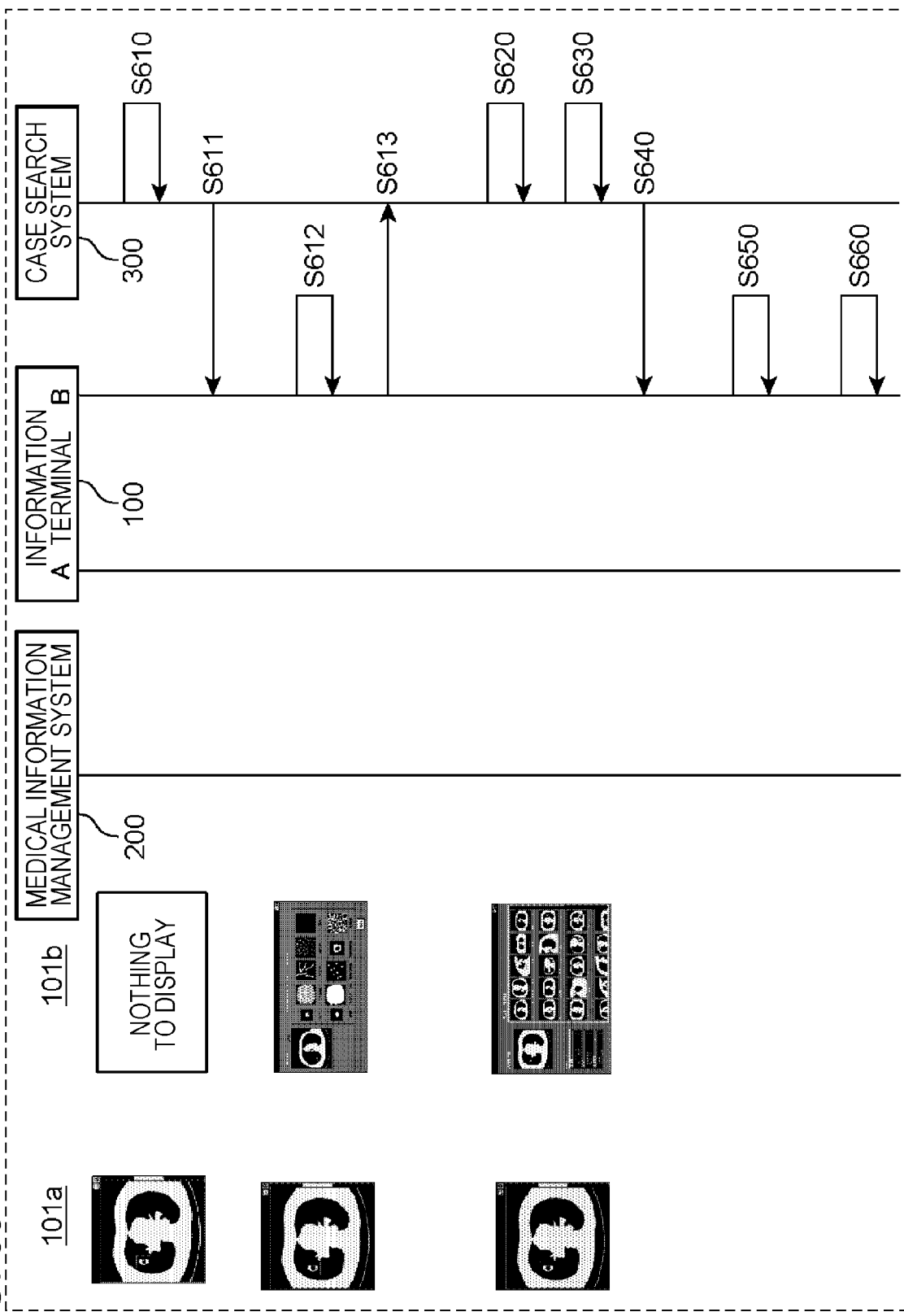
FIG. 55 is a sequence diagram illustrating the processes performed after a case search system receives a request for a similar case search until the case search system returns the result of the similar case search to an information terminal according to the second exemplary embodiment.

FIG. 55 is a sequence diagram illustrating the processes performed after the case search system 300 receives a request for a similar case search until the case search system 300 returns the result of the similar case search to the information terminal 100 according to the second exemplary embodiment. Unlike the first exemplary embodiment, according to the second exemplary embodiment, the processes in steps S611, S612, and S613 are added between the process to extract the image feature (S610) and the process to search for a similar case (S620). In addition, the process to search for a similar case (S620) and the process to detect user's operation performed on the disease name list display area 730 (S660) slightly differ from those of the first exemplary embodiment in relation to the input imaging findings. A process unique to the present exemplary embodiment in FIG. 55 is described below.

In step S610, the image feature extraction unit 302 of the case search system 300 extracts multi-dimensional image features from the set region of interest (an image feature set).

Subsequently, in step S611, the communication control unit 305 of the case search system 300 sends, to the information terminal 100, an instruction to input an imaging finding used for a similar case search. The way to use the imaging findings in the similar case search is described below.

Figure 56:
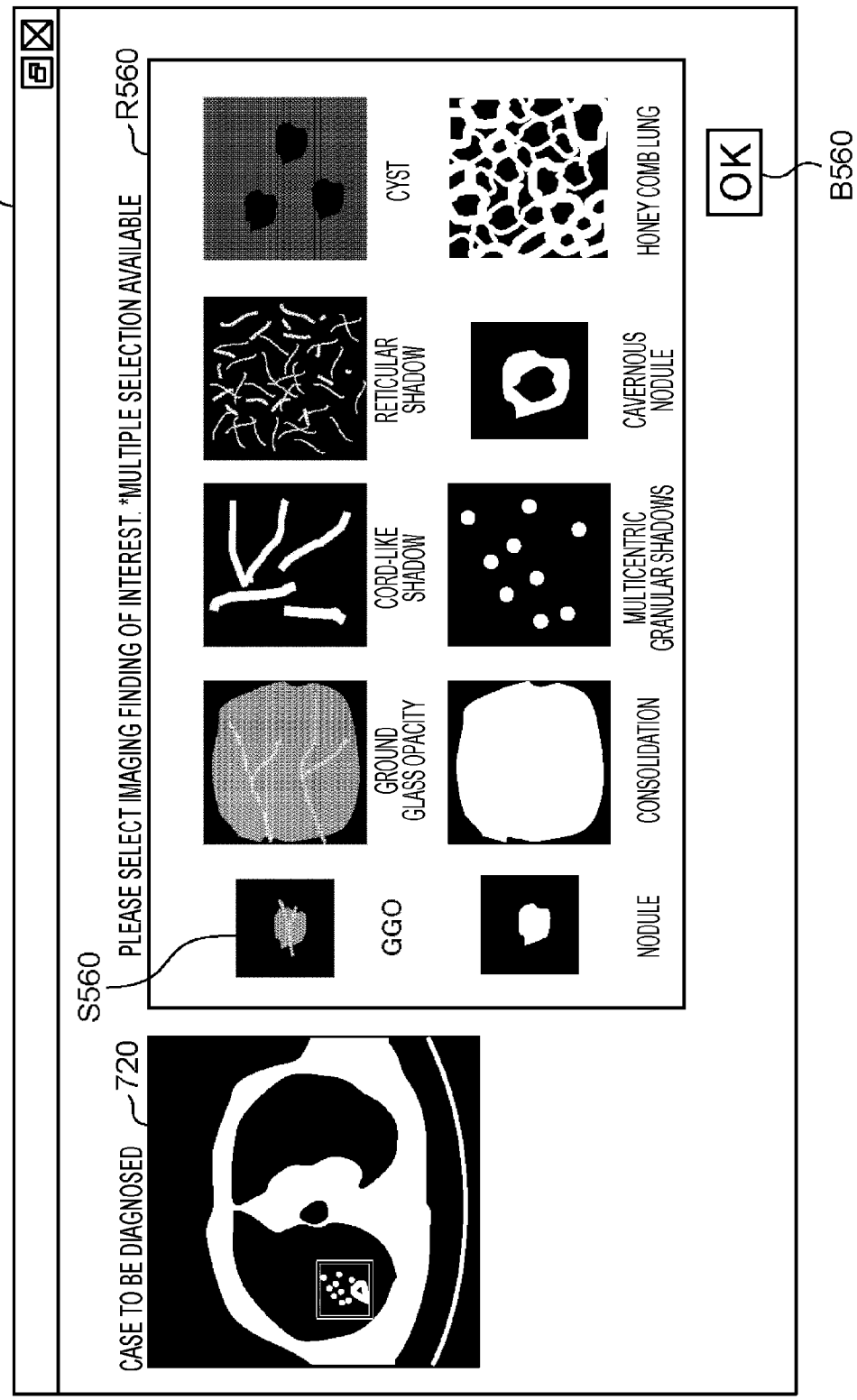
FIG. 56 illustrates an example of an input screen for prompting a user to input imaging findings according to the second exemplary embodiment.

In step S612, the information terminal 100 generates an input screen for prompting the user to input an imaging finding. FIG. 56 illustrates an example of an input screen G560 for prompting the user to input an imaging finding. In FIG. 56, ten predetermined imaging findings are presented to the user to prompt the user to select the desired imaging finding.

More specifically, the input screen G560 includes the diagnosis target image display area 720 and a selection area R560.

The selection area R560 presents thumbnail images S560 each corresponding to one of the plurality of imaging findings. In the example illustrated in FIG. 56, the selection area R560 presents 10 thumbnail images S560 arranged in 2 rows and 5 columns. However, this is only an example.

Figure 57:
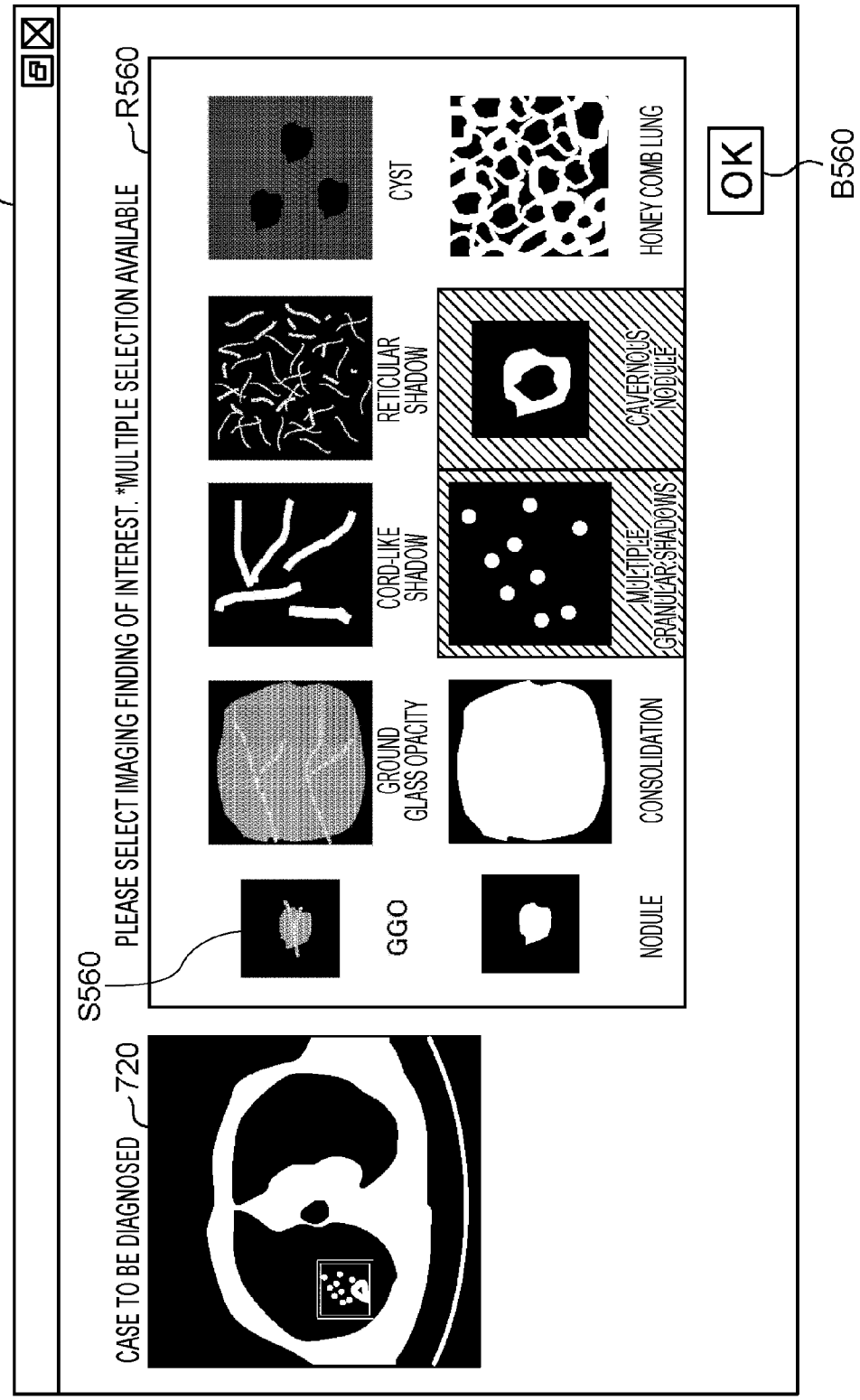
FIG. 57 illustrates an example of the input screen for prompting a user to input imaging findings according to the second exemplary embodiment.

Selection of one of the imaging findings is performed by clicking one of the thumbnail images S560 corresponding to the imaging findings. In addition, in the selection area R560, a plurality of the thumbnail images S560 can be selected at the same time. For example, in the selection area R560, each of the thumbnail images S560 can be toggle switched between a selected mode and an unselected mode. In FIG. 57, the input screen G560 in which two imaging findings are in the selected mode is illustrated.

In the example of FIG. 57, two imaging findings "multiple granular shadows" and "cavernous nodule" are in the selected mode. Note that to select an imaging finding, a text area in which the name of the imaging finding is displayed or an area in the vicinity of the text area may be clicked in addition to clicking the area of the thumbnail image S560.

By selecting at least one of the thumbnail images S560, the user selects at least one imaging finding. Thereafter, if the input control unit 103 detects user's operation to select an "OK" button B560 located at lower right of the screen illustrated in FIG. 57, the communication control unit 107 of the information terminal 100 sends information indicating the selected imaging finding to the case search system 300 (S613).

Figure 58:
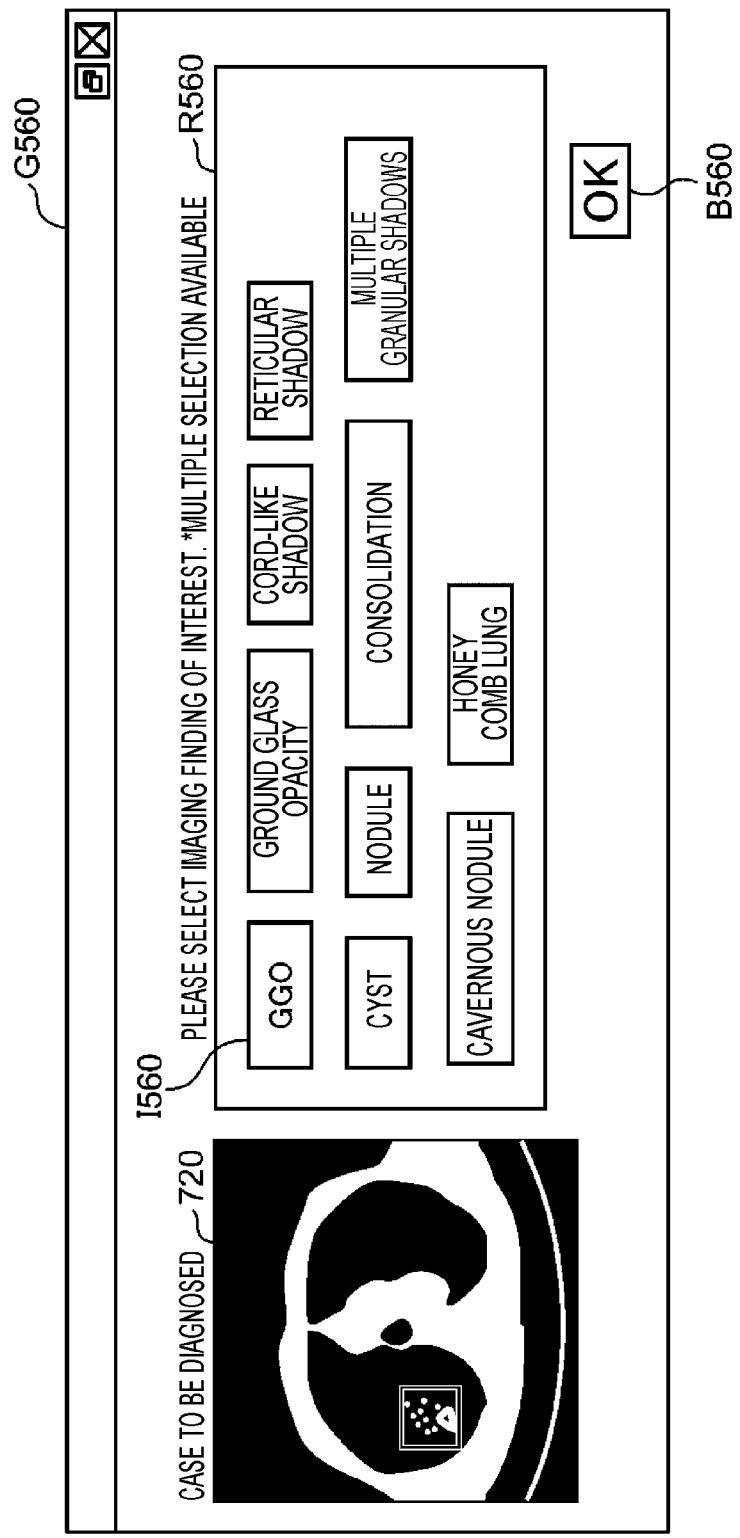
FIG. 58 illustrates an example of the input screen for prompting a user to input imaging findings according to the second exemplary embodiment.
Figure 59:
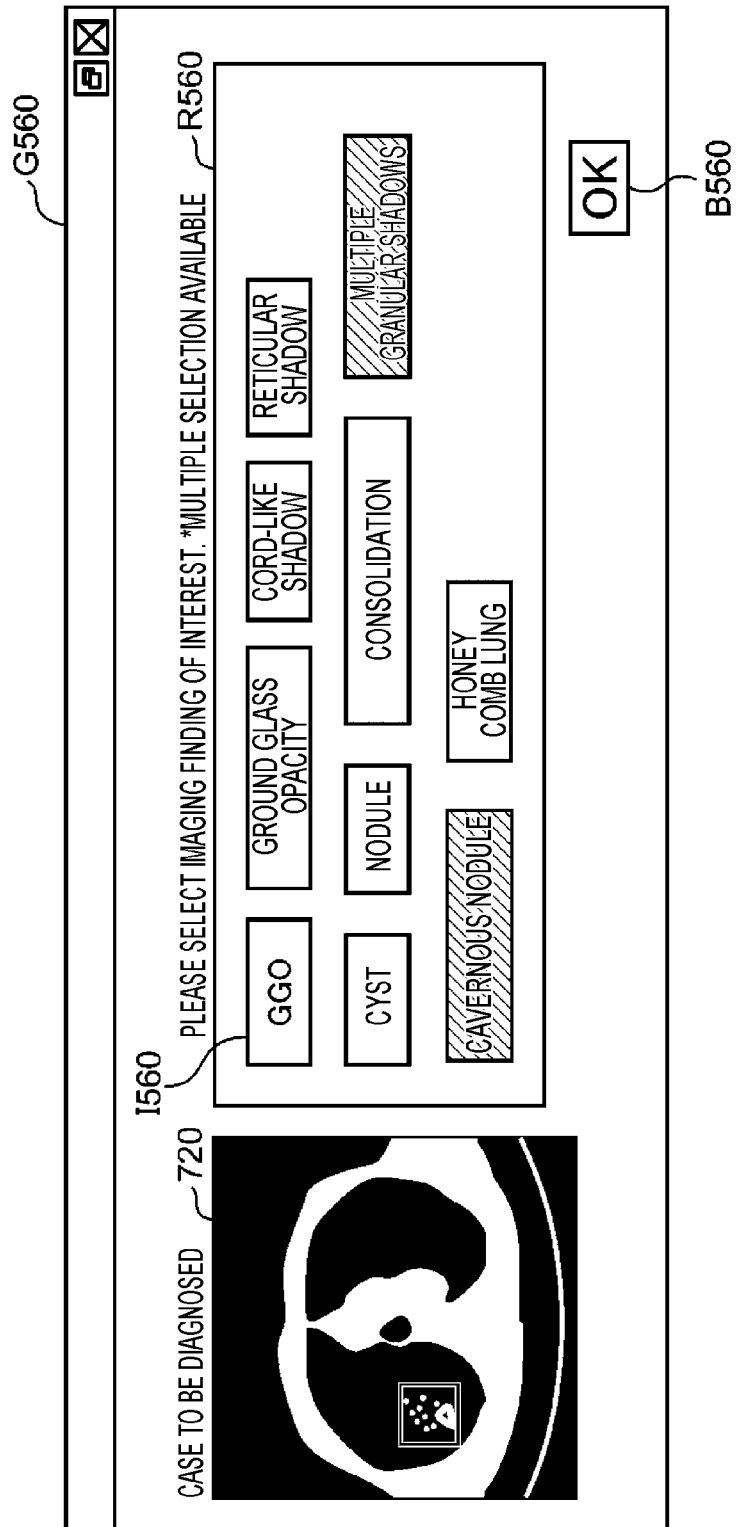
FIG. 59 illustrates an example of the input screen for prompting a user to input imaging findings according to the second exemplary embodiment.

Note that the input screen G560 generated in step S612 is not limited to the input screen G560 illustrated in FIG. 57. FIG. 58 illustrates another example of the input screen G560. For example, in the input screen G560 illustrated in FIG. 58, text icons I560 are used instead of the thumbnail images S560. FIG. 59 illustrates the input screen G560 in which two text icons I560 are in the selected mode. In the input screen G560 illustrated in FIG. 59, the rectangular icons I560 each having the text indicating the name of one of imaging findings therein are arranged in the selection area R560. Like the input screen G560 illustrated in FIG. 56, the user can select an imaging finding by clicking the text icon I560.

Figure 60:
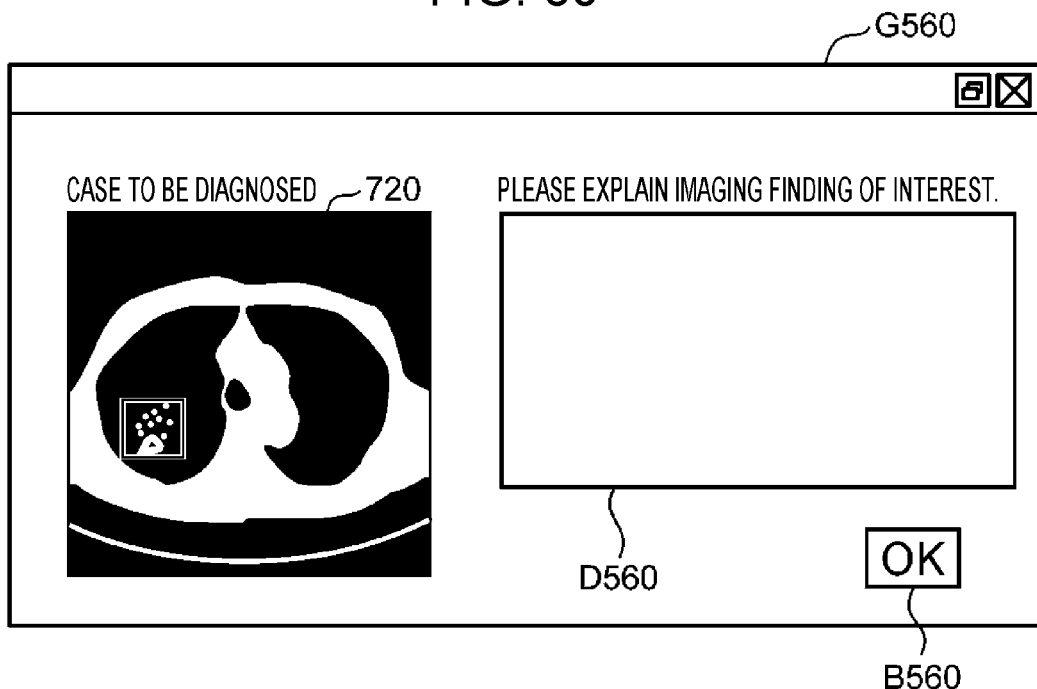
FIG. 60 illustrates an example of the input screen for prompting a user to input imaging findings according to the second exemplary embodiment.

FIG. 60 illustrates another example of the input screen G560. In the input screen G560 illustrated in FIG. 60, an input text area D560 that allows the user to write a description regarding the imaging finding to be interest thereinto is provided in the diagnosis target image display area 720.

Figure 61:
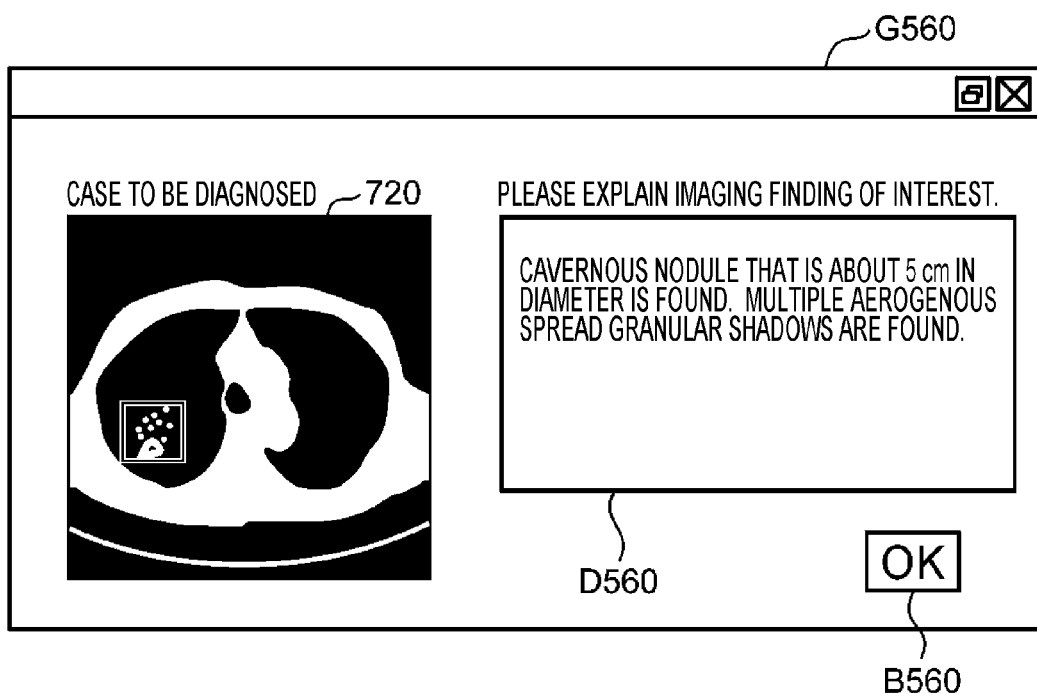
FIG. 61 illustrates an example of the input screen for prompting a user to input imaging findings according to the second exemplary embodiment.

FIG. 60 illustrates the input screen G560 having the input text area D560 containing a description written thereinto. The user can write a description regarding the imaging finding into the input text area D560 by operating the operation unit 102. When the input screen G560 including the input text area D560 is employed, the similar case search unit 303 performs natural language analysis in step S620 and extracts at least one word corresponding to the imaging finding from the text input to the input text area D560. Thereafter, the similar case search unit 303 determines which one of a predetermined number of the imaging findings (e.g., 10 imaging findings illustrated in FIG. 49) the extracted word correspond to. The determination can be made by associating the at least one extracted word with a predetermined imaging finding using a preprovided synonym dictionary. For example, in the example illustrated in FIG. 61, as the words associated with the imaging findings, the words "cavernous nodule" and "granular shadows" are extracted from the text input to the input text area D560. Thereafter, the extracted "cavernous nodule" is associated with "cavernous nodule", and the extracted "granular shadow" is associated with "multiple granular shadows". In this case, the similar case search unit 303 determines that the imaging findings of "cavernous nodule" and "multiple granular shadows" are selected.

The process of the similar case search performed in step S620 illustrated in FIG. 55 is described below.

The similar case search unit 303 employs a method for searching a similar case by using, for example, the imaging finding input for search and increasing the weight of a focused dimension among the multi-dimensional image feature sets extracted from the region of interest.

In this example, a focused dimension is predetermined for each of the predetermined number of the imaging findings (10 imaging findings illustrated in FIG. 49 in this example). As a focused dimension, the dimension that well presents the feature of the imaging finding can be employed. The similar case search unit 303 increases the weight of the predetermined focused dimension for the imaging finding specified in search and performs a search process. In this manner, the similar case search unit 303 can perform the search process appropriate in accordance with the imaging finding specified by the user. More specifically, the method described in PCT/JP2011/006161 can be employed as the search method.

Alternatively, as illustrated in FIG. 62, another search process in which an image finding ID 4950 is included in each of the pieces of region-of-interest information in the similar case data 4000 may be employed. FIG. 62 illustrates another example of the similar case data 4000.

Unlike the similar case data 4000 illustrated in FIG. 15, the similar case data 4000 illustrated in FIG. 62 further includes the image finding ID 4950.

As the image finding ID 4950, an identifier for identifying an imaging finding in the categories the same as those of the imaging finding input for searching (S612) can be employed. For example, the image finding IDs 4950 of CAT3 and CAT7 are associated with the region of interest having a region-of-interest ID =SIM523_0 of two regions of interest included in the similar case data 4000 illustrated in FIG. 62, and the image finding ID 4950 of CAT3 is associated with the region of interest having a region-of-interest ID=SIM523_1 of the two regions of interest included in the similar case data 4000.

At that time, suppose that the image finding ID 4950 of the imaging finding input for search is CAT3. In such a case, the similar case search unit 303 searches for the regions of interest of an imaging finding ID=SIM5232_0 and the regions of interest of an imaging finding ID=SIM5232_1. Alternatively, suppose that the image finding ID 4950 of the imaging finding input for search is CAT7. In such a case, the similar case search unit 303 searches for similar cases having a region of interest of an imaging finding ID=SIM5232_. Still alternatively, suppose that the image finding IDs 4950 of the imaging findings input for search are CAT3 and CAT7. In such a case, the similar case search unit 303 searches for the regions of interest of an imaging finding ID=SIM5232_0. Thereafter, the similar case search unit 303 selects, as a similar case for the search query image, the similar case having a distance between the image feature set of the region of interest to be searched and the image feature set of the region of interest of the search query image that is less than or equal to the threshold value.

Figure 63:
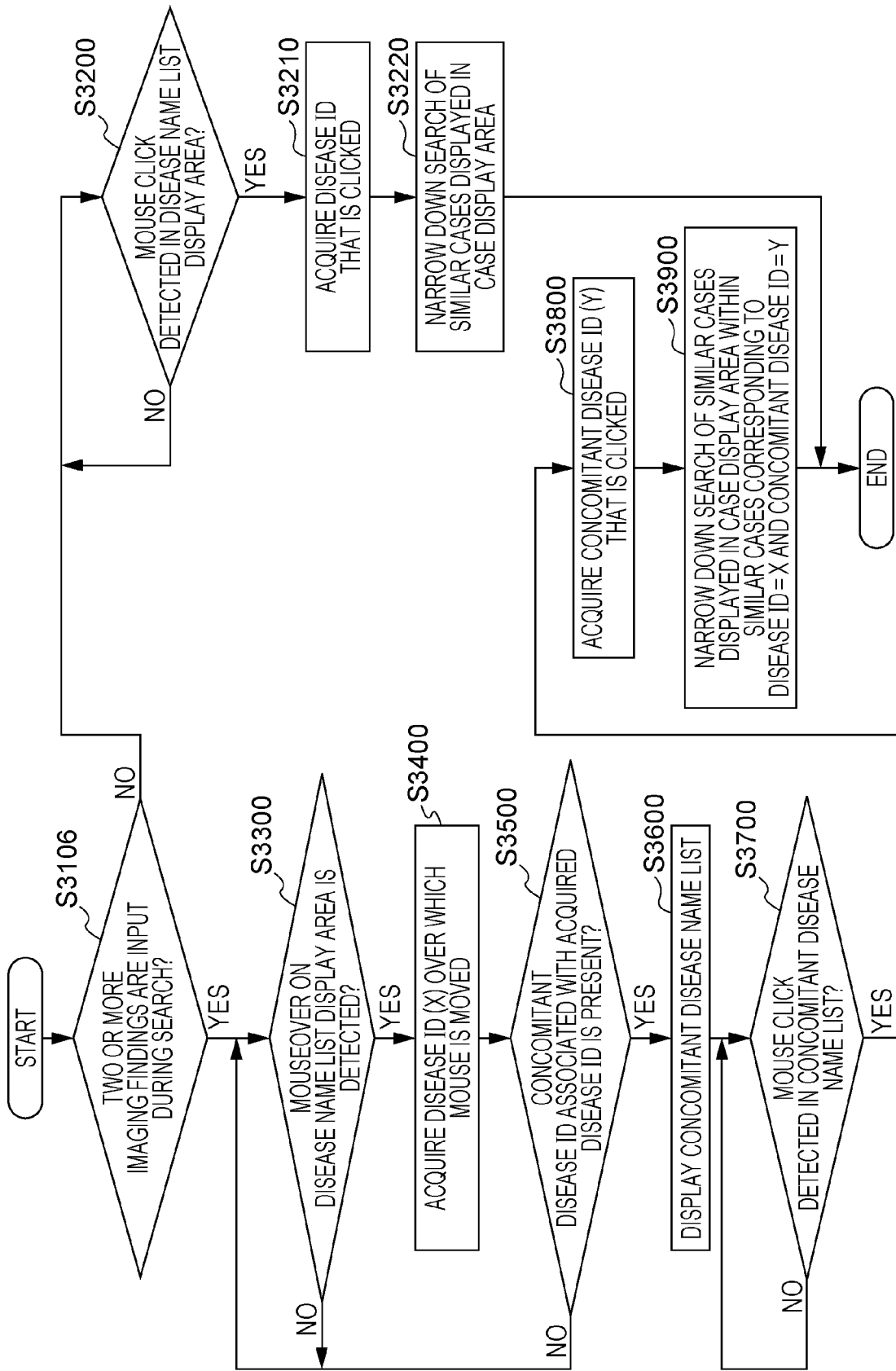
FIG. 63 is a flowchart of a concomitant disease name listing process according to the second exemplary embodiment.

The process performed in step S660 of FIG. 55 by the information terminal 100 when the disease name list display area 730 is manipulated (i.e., the concomitant disease name listing process) is described with reference to a flowchart illustrated in FIG. 63. The flowchart illustrated in FIG. 63 differs from the flowchart of the first exemplary embodiment illustrated in FIG. 35 in that step S3100 is replaced with step S3106. If in step S3106, "two or more imaging findings are input when search is started (S612 of FIG. 55)" (YES in step S3106), the processing proceeds to step S3300. However, if "two or more imaging findings are not input when search is started (S612 of FIG. 55)" (NO in step S3106), the processing proceeds to step S3200. The other processes are the same as those of the first exemplary embodiment (refer to FIG. 35).

Like the first exemplary embodiment, according to the second exemplary embodiment, the concomitant disease name list 750 is displayed. Accordingly, the user can easily diagnose whether a plurality of diseases occur in the case to be diagnosed. In addition, according to the second exemplary embodiment, if two or more imaging findings are input when search is started (S612 of FIG. 55), the concomitant disease name list 750 is displayed. That is, only when a plurality of diseases are highly likely to occur at the same time, the concomitant disease name list 750 is displayed. Accordingly, when a plurality of diseases are less likely to occur at the same time, a physician can focus on diagnosis of a single disease.

Third Exemplary Embodiment

The third exemplary embodiment is described below. In the third exemplary embodiment, the elements and processes that are not described are the same as those of the first exemplary embodiment, unless expressly specified otherwise.

Figure 64:
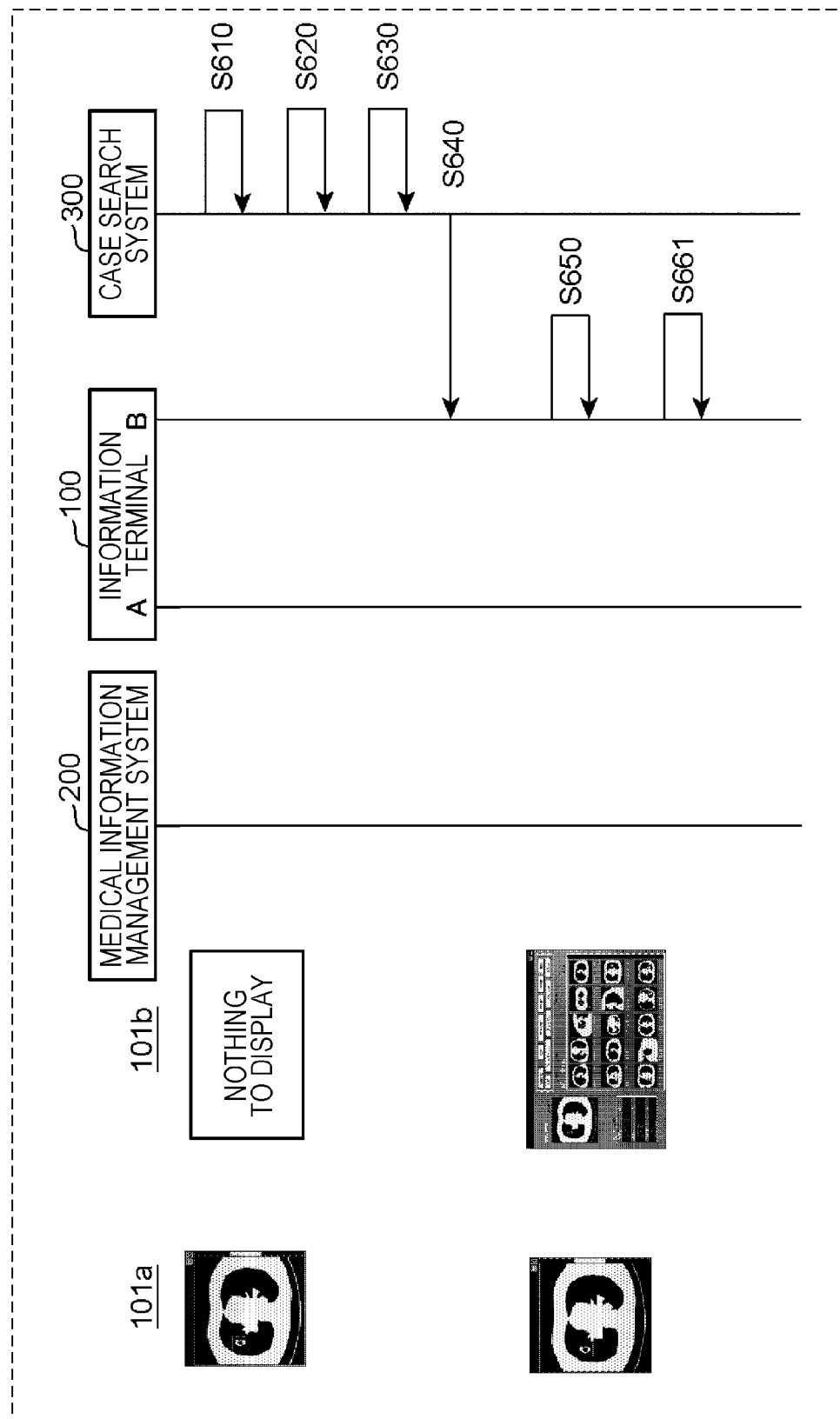
FIG. 64 is a sequence diagram illustrating the processes performed after a case search system receives a request for a similar case search until the case search system returns the result of the similar case search to an information terminal according to a third exemplary embodiment.

FIG. 64 is a sequence diagram illustrating the processes performed after the case search system 300 receives a request for a similar case search until the case search system 300 returns the result of the similar case search to the information terminal 100 according to the third exemplary embodiment. The third exemplary embodiment differs from the first exemplary embodiment in terms of the processes performed in steps S650 and S661.

Figure 65:
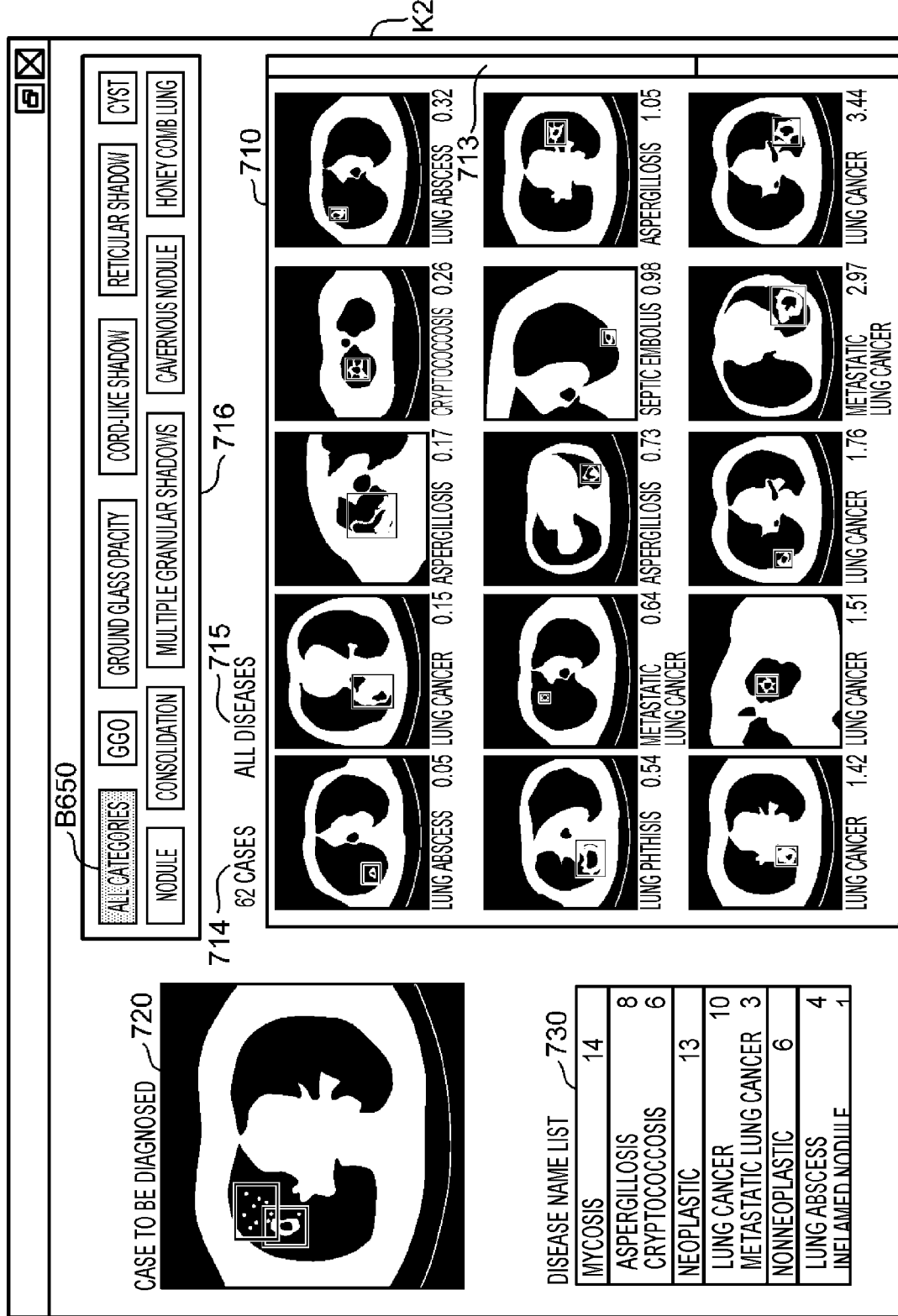
FIG. 65 illustrates an example of a basic screen displayed on a display immediately after a similar case search application is started in the information terminal according to the third exemplary embodiment.

FIG. 65 illustrates an example of a basic screen K2 displayed on the display 101b immediately after the similar case search application is started in the information terminal 100 according to the third exemplary embodiment. Unlike the basic screen K2 of the first exemplary embodiment, the basic screen K2 of the third exemplary embodiment includes an imaging findings narrowed search area 716 (an example of a third display area) in the upper section of the screen. The imaging findings narrowed search area 716 includes a plurality of imaging finding selection buttons B650. The imaging finding selection buttons B650 are used to narrow down a search of the similar cases to be displayed in the case display area 710. Note that the types of displayed imaging finding selection button B650 are predetermined. According to the present exemplary embodiment, ten imaging finding selection buttons B650 each corresponding to one of the ten imaging findings illustrated in FIG. 49 are provided in the imaging findings narrowed search area 716. In the example illustrated in FIG. 65, in addition to the ten imaging finding selection buttons B650 each corresponding to one of the ten imaging findings, an imaging finding selection button B650 having a text "all categories" thereon is provided in the imaging findings narrowed search area 716. The imaging finding selection button B650 having a text "all categories" thereon is used not to select any one of the imaging findings.

Immediately after the basic screen K2 is generated, the imaging finding selection button B650 having a text "all categories" thereon is enabled. This helps the user to understand that all the imaging findings are displayed before the user selects the imaging finding selection button B650. That is, immediately after the basic screen K2 is generated, all the similar cases of the search query image are displayed in the case display area 710.

In step S661 illustrated in FIG. 64, the input control unit 103 detects user's operation performed on the imaging finding selection button B650 or the disease name list display area 730.

Like the first exemplary embodiment, the similar cases accumulated in the similar case data 4000 are displayed in the case display area 710 in descending order of the distance measured from the image feature set extracted from the region of interest of the search query image. At that time, the user further inputs the imaging finding or the disease name to be focused and, thus, narrowed search can be performed to narrow down a number of the similar cases displayed in the case display area 710. In the example illustrated in FIG. 66, among the imaging finding selection buttons B650, the "multiple granular shadows" button and the "cavernous nodule" button are selected. Accordingly, the display control unit 104 narrows down the search of the similar cases displayed in the case display area 710 to the similar cases related to the imaging findings "multiple granular shadows" and "cavernous nodule" and displays the similar cases.

According to the present exemplary embodiment, to perform this process, the similar case data 4000 of the second exemplary embodiment illustrated in FIG. 62 is employed as the similar case data 4000. The similar case data 4000 illustrated in FIG. 62 has the image finding ID 4950 for each of the regions of interest. The ID used to identify an imaging finding in the categories that are the same as those of the imaging finding input for the search (S612) can be employed as the image finding ID 4950. If the input control unit 103 detects user's operation to select the imaging finding selection button B650, the display control unit 104 performs a process to narrow down the search of the similar cases displayed in the case display area 710 to the similar cases each having an image finding ID 4950 corresponding to the selected one of the imaging finding selection buttons B650. At that time, the display control unit 104 updates the information displayed in the case count display area 714 and the disease name list display area 730 in accordance with the result of the narrowed search.

Figure 66:
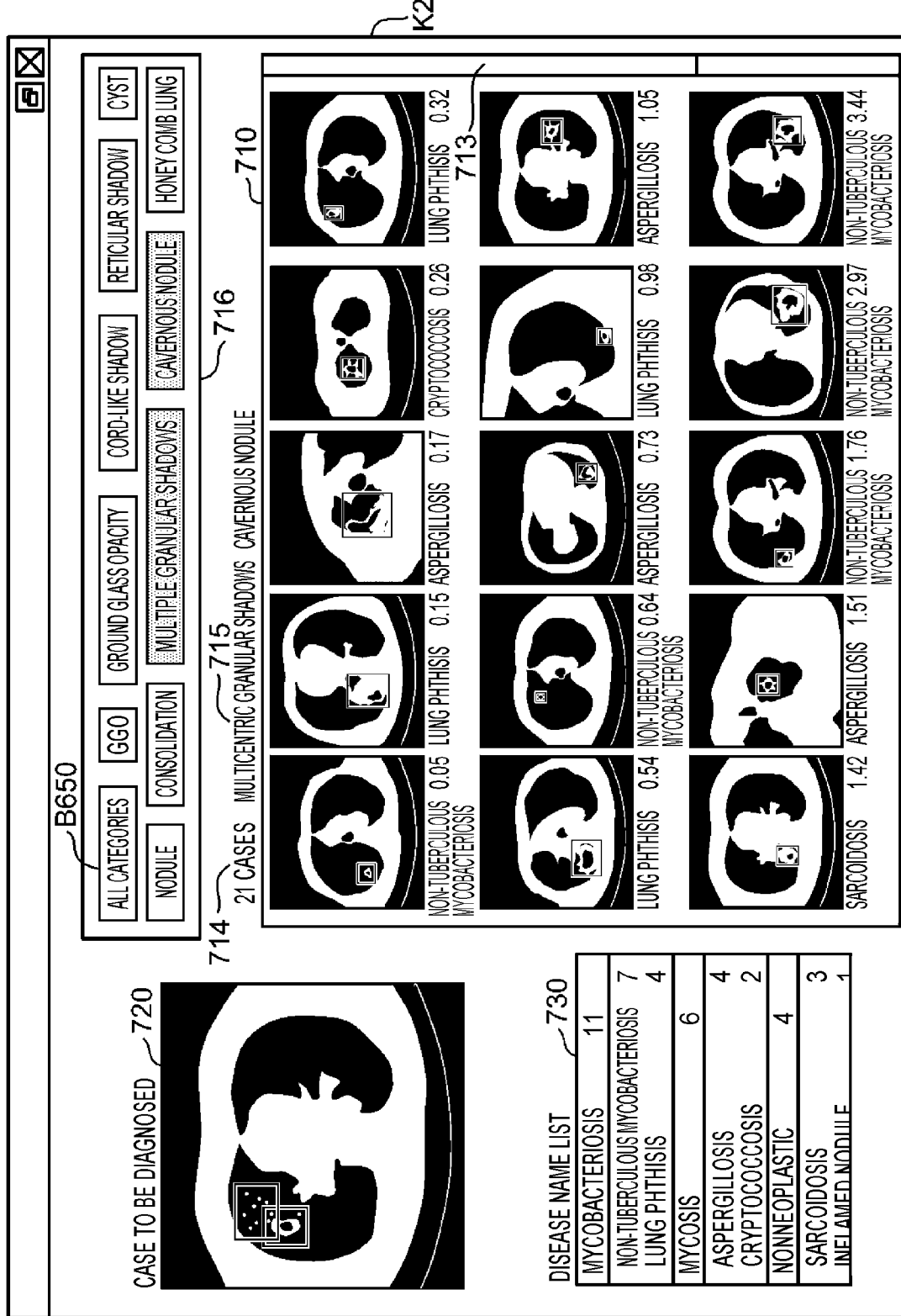
FIG. 66 illustrates an example of a basic screen displayed when an operation to narrow down the imaging findings is input therein in the information terminal according to the third exemplary embodiment.

In the example illustrated in FIG. 66, since the number of cases of "multiple granular shadows" and "cavernous nodule" is equal to 21, "21 cases" is displayed in the case count display area 714. In addition, in the example illustrated in FIG. 66, since "multiple granular shadows" and "cavernous nodule" are selected, "Multiple granular shadows Cavernous nodule" is displayed in the disease condition display area 715. Furthermore, in the example illustrated in FIG. 66, among the similar cases having imaging findings of multiple granular shadows and cavernous nodule, the number of similar cases of mycobacteriosis (a large category disease name) is equal to 11, the number of similar cases of mycosis (a large category disease name) is equal to 6, and the number of similar cases of nonneoplastic (a large category disease name) is equal to 4. Accordingly, the information in the disease name list display area 730 is updated so as to correspond to the numbers. In addition, the small category disease names are updated in accordance with the result of the narrowed search.

While the above example has been described with reference to use of the image finding ID 4950 given to the similar case data 4000 when the search of the similar cases displayed in the case display area 710 is narrowed down, this search technique is only an example. As described in the second exemplary embodiment, the search technique of increasing the weight of the focused dimension of the image feature set may be employed. More specifically, the display control unit 104 can increase the weight of a predetermined dimension for the selected imaging finding and calculate the distance between the image feature set of the search query image and the image feature set of each of the similar cases displayed in the case display area 710. Thereafter, the display control unit 104 can display, in the case display area 710, the similar cases each having a distance less than or equal to a predetermined threshold value.

Figure 67:
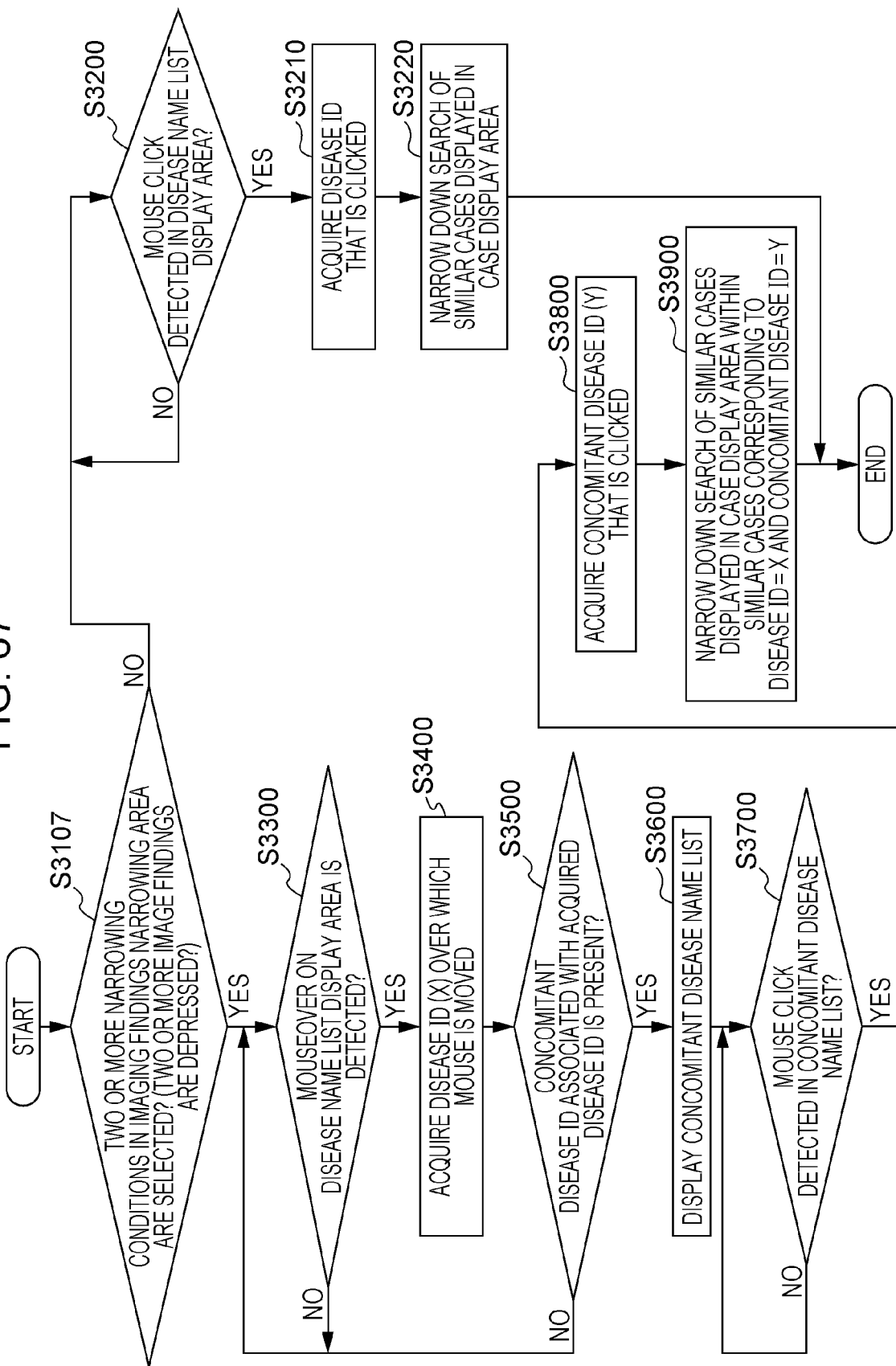
FIG. 67 is a flowchart of a concomitant disease name listing process according to the third exemplary embodiment.

An operation performed on the disease name list display area 730 is described below. The process performed by the information terminal 100 when user's operation on the disease name list display area 730 is input in step S661 of FIG. 64 (the concomitant disease name listing process) is described below with reference to a flowchart illustrated in FIG. 67. Unlike the first exemplary embodiment, according to the third exemplary embodiment, step S3107 is provided instead of step S3100. If in step S3107, "two or more narrowing conditions in the imaging findings narrowed search area 716 are selected (two or more imaging findings are depressed)" (YES in step S3107), the processing proceeds to step S3300. However, if "two or more narrowing conditions in the imaging findings narrowed search area 716 are not selected (two or more imaging findings are not depressed)" (NO in step S3107), the processing proceeds to step S3200. The other processes are the same as those of the first exemplary embodiment (refer to FIG. 35).

Like the first exemplary embodiment, according to the third exemplary embodiment, the concomitant disease name list 750 is displayed. Accordingly, the user can easily diagnose whether a plurality of diseases occur in the case to be diagnosed. In addition, according to the third exemplary embodiment, if two or more imaging findings are input when search is started (S661 of FIG. 64), the concomitant disease name list 750 is displayed. That is, only when a plurality of diseases are highly likely to occur at the same time, the concomitant disease name list 750 is displayed. Accordingly, when a plurality of diseases are less likely to occur at the same time, the physician can focus on diagnosis of a single disease.

Fourth Exemplary Embodiment

Figure 68:
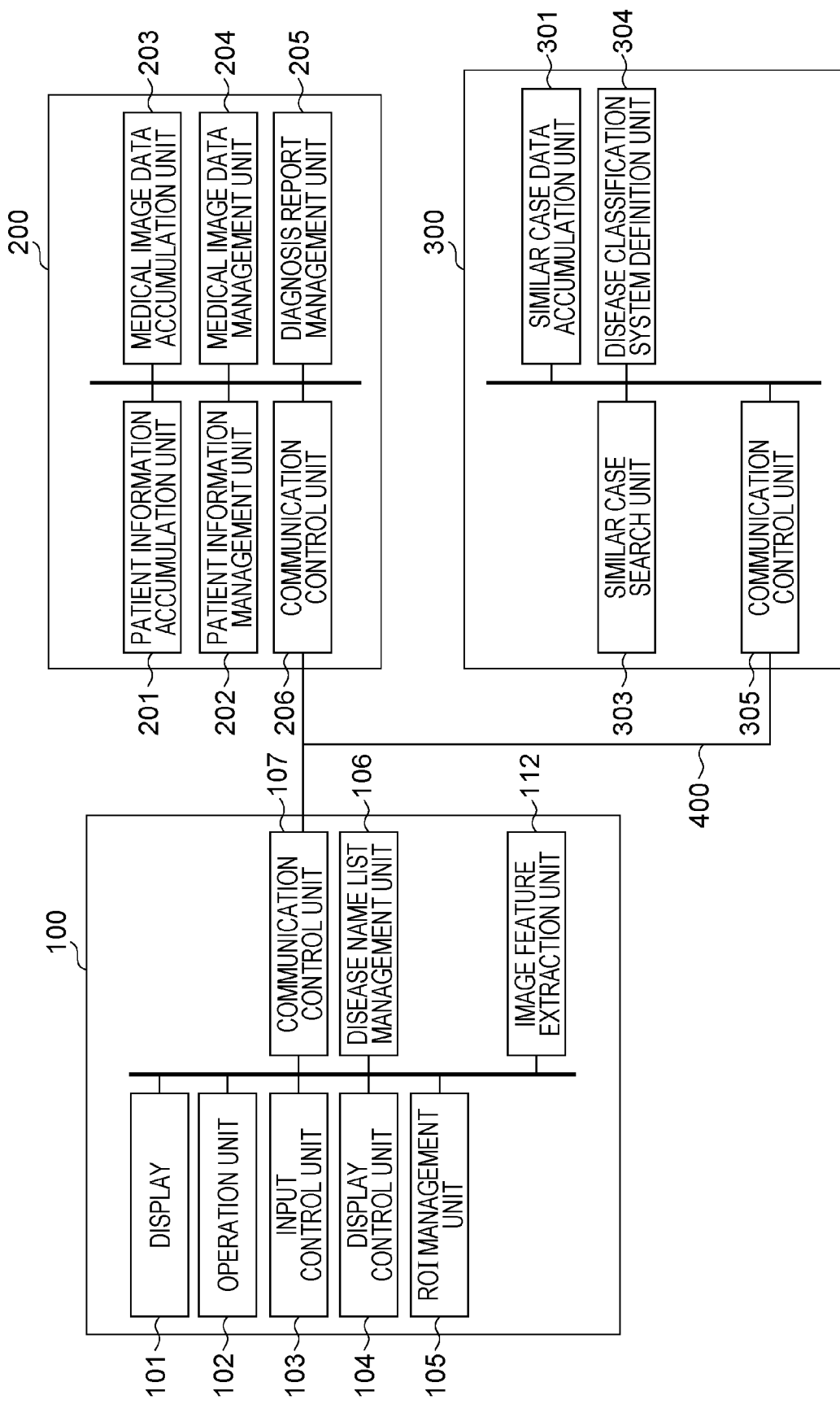
FIG. 68 is a block diagram of an information terminal, a medical information management system, and a case search system according to a fourth exemplary embodiment.

The fourth exemplary embodiment is characterized in that the information terminal 100 extracts the image feature. FIG. 68 is a block diagram of an information terminal 100, a medical information management system 200, and a case search system 300 according to the fourth exemplary embodiment.

Unlike FIG. 2, the information terminal 100 further includes an image feature extraction unit 112, and the image feature extraction unit 302 is removed from the case search system 300.

Figure 69:
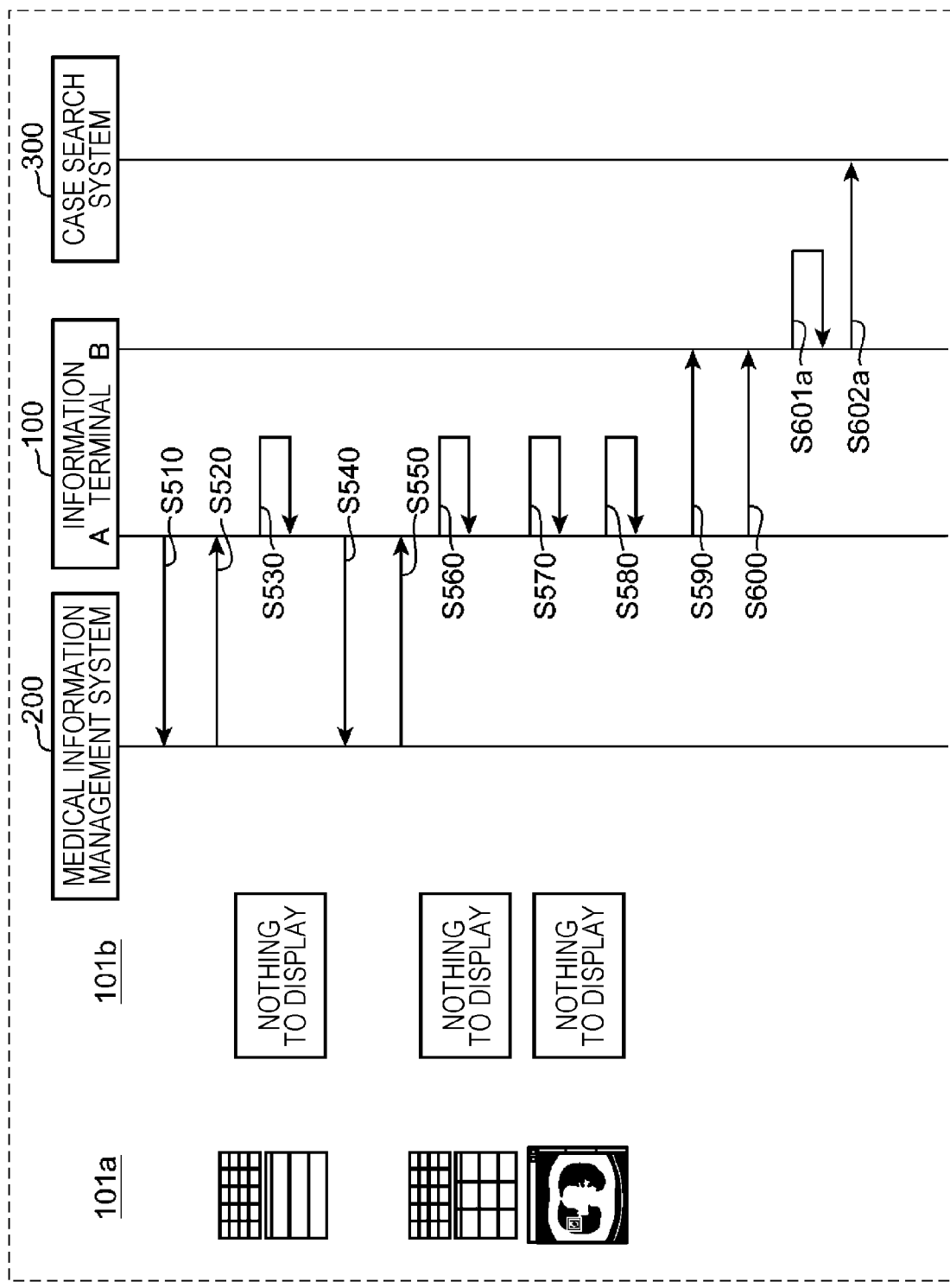
FIG. 69 is a sequence diagram illustrating the processes performed after the information terminal receives a case to be diagnosed from a medical information management system until a case search system receives a request for a similar case search according to the fourth exemplary embodiment.

FIG. 69 is a sequence diagram illustrating the processes performed after the information terminal 100 receives a case to be diagnosed from the medical information management system 200 until the case search system 300 receives a request for a similar case search.

Unlike FIG. 17, after the ROI management unit 105 sends the slice images of the case to be diagnosed to the communication control unit 107 (S600), the image feature is extracted by the information terminal 100 (S601a), and the extracted image features are sent to the case search system 300 together with the slice images (S602a). The process to extract the image feature (S601a) is the same as that performed in the case search system 300.

FIG. 70 is a sequence diagram illustrating a process performed after the case search system 300 receives a request for a similar case search until the case search system 300 returns the result of the similar case search to the information terminal 100. Unlike FIG. 21, FIG. 70 does not include a process to extract the image feature (S610), since the image feature is extracted by the information terminal 100.

The present disclosure is applicable to a similar case search system that presents similar cases referenced in diagnosis of a medical image to be interpreted and an interpretation training apparatus for radiologist interns.

What is claimed is:

1. A method for an information terminal including a computer, the method comprising:

detecting, using the computer, designation information indicating a plurality of interested areas in a medical image to be interpreted;

after detecting the designation information indicating the plurality of interested areas, (i) receiving, using the computer, first information indicating a plurality of disease names including a first disease name and a second disease name and (ii) receiving, using the computer, a first set of similar medical images each having a predetermined similarity to the medical image to be interpreted;

after receiving the first information and the first set of similar medical images, (i) displaying, using the computer, the first set of similar medical images in a first area of a display and (ii) displaying, using the computer, a first list of disease names in a second area of the display, wherein the first list of disease names includes the first disease name and the second disease name, wherein the first set of similar medical images includes a first similar medical image and a second similar medical image, and wherein the second similar medical image corresponds to the first disease name and the second disease name;

after displaying the first list of disease names, receiving, using the computer, a selection of the second disease name included in the first list of disease names;

after receiving the selection of the second disease name, displaying, using the computer, a second list of one or more disease names, wherein the second list of one or more disease names includes a third disease name, and wherein the second list of one or more disease names is simultaneously displayed on the display with the first list of disease names;

after displaying the second list of one or more disease names, receiving, using the computer, a selection of the third disease name included in the second list of one or more disease names; and after receiving the selection of the third disease name, displaying, using the computer, a second set of similar medical images in the first area without displaying the first set of similar medical images in the first area, wherein the second set of similar medical images corresponds to the second disease name and the third disease name, and wherein the first set of similar medical images includes the second set of similar medical images.

2. A method for an information terminal including a computer, the method comprising:

detecting, using the computer, first designation information indicating a plurality of interested areas in a medical image to be interpreted;

detecting, using the computer, second designation information indicating at least one imaging finding selected from a plurality of imaging findings, the second designation information being received after display of the plurality imaging findings and a plurality of images corresponding one-to-one relationship with the plurality of imaging findings;

after detecting the first designation information and the second designation information, (i) receiving, using the computer, first information indicating a plurality of disease names including a first disease name and a second disease name and (ii) receiving, using the computer, a first set of similar medical images, the first information and the first set of similar medical images being received based on the first designation information and the second designation information;

after receiving the first information and the first set of similar medical images, (i) displaying, using the computer, the first set of similar medical images in a first area of a display and (ii) displaying, using the computer, a first list of disease names in a second area of the display, wherein the first list of disease names includes the first disease name and the second disease name, wherein the first set of similar medical images includes a first similar medical image and a second similar medical image, and wherein the second similar medical image corresponds to the first disease name and the second disease name;

after displaying the first list of disease names, receiving, using the computer, a selection of the second disease name included in the first list of disease names;

after receiving the selection of the second disease name, displaying, using the computer, a second list of one or more disease names, wherein the second list of one or more disease names includes a third disease name, and wherein the second list of one or more disease names is simultaneously displayed on the display with the first list of disease names;

after displaying the second list of one or more disease names, receiving, using the computer, a selection of the third disease name included in the second list of one or more disease names; and after receiving the selection of the third disease name, displaying, using the computer, a second set of similar medical images in the first area without displaying the first set of similar medical images in the first area, wherein the second set of similar medical images corresponds to the second disease name and the third disease name, and wherein the first set of similar medical images includes the second set of similar medical images.

3. A non-transitory computer-readable recording medium storing therein a control program, which when executed, causes an information terminal including a computer to perform a process comprising:

detecting, using the computer, designation information indicating a plurality of interested areas in a medical image to be interpreted;

after detecting the designation information indicating the plurality of interested areas, (i) receiving, using the computer, first information indicating a plurality of disease names including a first disease name and a second disease name and (ii) receiving, using the computer, a first set of similar medical images each having a predetermined similarity to the medical image to be interpreted;

after receiving the first information and the first set of similar medical images, (i) displaying, using the computer, the first set of similar medical images in a first area of a display and (ii) displaying, using the computer, a first list of disease names in a second area of the display, wherein the first list of disease names includes the first disease name and the second disease name, wherein the first set of similar medical images includes a first similar medical image and a second similar medical image, and wherein the second similar medical image corresponds to the first disease name and the second disease name;

after displaying the first list of disease names, receiving, using the computer, a selection of the second disease name included in the first list of disease names;

after receiving the selection of the second disease name, displaying, using the computer, a second list of one or more disease names, wherein the second list of one or more disease names includes a third disease name, and wherein the second list of one or more disease names is simultaneously displayed on the display with the first list of disease names;

after displaying the second list of one or more disease names, receiving, using the computer, a selection of the third disease name included in the second list of one or more disease names; and after receiving the selection of the third disease name, displaying, using the computer, a second set of similar medical images in the first area without displaying the first set of similar medical images in the first area, wherein the second set of similar medical images corresponds to the second disease name and the third disease name, and wherein the first set of similar medical images includes the second set of similar medical images.

4. A non-transitory computer-readable recording medium storing therein a control program, which when executed, causes an information terminal including a computer to perform a process comprising:

detecting, using the computer, first designation information indicating a plurality of interested areas in a medical image to be interpreted;

detecting, using the computer, second designation information indicating at least one imaging finding selected from a plurality of imaging findings, the second designation information being received after display of the plurality imaging findings and a plurality of images corresponding one-to-one relationship with the plurality of imaging findings;

after detecting the first designation information and the second designation information, (i) receiving, using the computer, first information indicating a plurality of disease names including a first disease name and a second disease name and (ii) receiving, using the computer, a first set of similar medical images, the first information and the first set of similar medical images being received based on the first designation information and the second designation information;

after receiving the first information and the first set of similar medical images, (i) displaying, using the computer, the first set of similar medical images in a first area of a display and (ii) displaying, using the computer, a first list of disease names in a second area of the display, wherein the first list of disease names includes the first disease name and the second disease name, wherein the first set of similar medical images includes a first similar medical image and a second similar medical image, and wherein the second similar medical image corresponds to the first disease name and the second disease name;

after displaying the first list of disease names, receiving, using the computer, a selection of the second disease name included in the first list of disease names;

after receiving the selection of the second disease name, displaying, using the computer, a second list of one or more disease names, wherein the second list of one or more disease names includes a third disease name, and wherein the second list of one or more disease names is simultaneously displayed on the display with the first list of disease names;

after displaying the second list of one or more disease names, receiving, using the computer, a selection of the third disease name included in the second list of one or more disease names; and after receiving the selection of the third disease name, displaying, using the computer, a second set of similar medical images in the first area without displaying the first set of similar medical images in the first area, wherein the second set of similar medical images corresponds to the second disease name and the third disease name, and wherein the first set of similar medical images includes the second set of similar medical images.

5. The method according to claim 2, wherein the plurality of imaging findings include consolidation.

6. The non-transitory computer-readable recording medium according to claim 4, wherein the plurality of imaging findings include consolidation.

* * * * *